(12) United States Patent
Zhi et al.

(10) Patent No.: US 10,111,859 B2
(45) Date of Patent: Oct. 30, 2018

(54) METHODS AND COMPOSITIONS ASSOCIATED WITH THE GRANULOCYTE COLONY-STIMULATING FACTOR RECEPTOR

(71) Applicant: Ligand Pharmaceuticals, Inc., San Diego, CA (US)

(72) Inventors: Lin Zhi, San Diego, CA (US); Andrew R. Hudson, San Diego, CA (US); Keith Marschke, San Diego, CA (US); Virginia H. Grant, San Diego, CA (US); Steven L. Roach, San Deigo, CA (US); Yixing Shen, Encinitas, CA (US); Jason C. Pickens, San Diego, CA (US); Bijan Pedram, San Diego, CA (US); Cornelius Arjan van Oeveren, San Diego, CA (US); Lino J. Valdez, San Diego, CA (US)

(73) Assignee: LIGAND PHARMACEUTICALS, INC., San Diego, CA (US)

( * ) Notice: Subject to any disclaimer, the term of this patent is extended or adjusted under 35 U.S.C. 154(b) by 0 days.

(21) Appl. No.: 15/247,164

(22) Filed: Aug. 25, 2016

(65) Prior Publication Data
US 2016/0374989 A1 Dec. 29, 2016

Related U.S. Application Data

(63) Continuation of application No. 14/357,551, filed as application No. PCT/US2012/064706 on Nov. 12, 2012, now Pat. No. 9,492,430.

(60) Provisional application No. 61/561,510, filed on Nov. 18, 2011, provisional application No. 61/559,660, filed on Nov. 14, 2011.

(51) Int. Cl.

| | | |
|---|---|---|
| A61K 31/404 | (2006.01) | |
| C07D 401/12 | (2006.01) | |
| C07D 403/12 | (2006.01) | |
| C07D 231/46 | (2006.01) | |
| C07D 405/06 | (2006.01) | |
| C07D 209/34 | (2006.01) | |
| A61K 31/41 | (2006.01) | |
| A61K 31/4152 | (2006.01) | |
| A61K 31/4155 | (2006.01) | |
| A61K 31/454 | (2006.01) | |
| A61K 45/06 | (2006.01) | |
| A61N 5/10 | (2006.01) | |
| C12Q 1/18 | (2006.01) | |
| C12Q 1/66 | (2006.01) | |
| C07D 231/52 | (2006.01) | |

(52) U.S. Cl.
CPC .......... *A61K 31/404* (2013.01); *A61K 31/41* (2013.01); *A61K 31/4152* (2013.01); *A61K 31/4155* (2013.01); *A61K 31/454* (2013.01); *A61K 45/06* (2013.01); *A61N 5/10* (2013.01); *C07D 209/34* (2013.01); *C07D 231/46* (2013.01); *C07D 231/52* (2013.01); *C07D 401/12* (2013.01); *C07D 403/12* (2013.01); *C07D 405/06* (2013.01); *C12Q 1/18* (2013.01); *C12Q 1/66* (2013.01)

(58) Field of Classification Search
CPC .......................... A61K 31/404; C07D 401/12
See application file for complete search history.

(56) References Cited

U.S. PATENT DOCUMENTS

| | | | |
|---|---|---|---|
| 6,737,434 B2 | 5/2004 | Tokizawa | |
| 7,026,334 B1 | 4/2006 | Takemoto | |
| 8,093,251 B2 | 1/2012 | Miyaji | |
| 2007/0129539 A1* | 6/2007 | Zhi | C07D 231/38 534/792 |
| 2008/0139621 A1* | 6/2008 | Spencer | C07D 231/46 514/326 |
| 2009/0198060 A1 | 8/2009 | Miyaji | |

FOREIGN PATENT DOCUMENTS

| | | |
|---|---|---|
| EP | 1 647 553 A1 | 4/2006 |
| EP | 1 655 291 A1 | 5/2006 |
| EP | 2 025 671 A1 | 2/2009 |
| JP | 2007-063443 | 3/2007 |
| WO | WO 2001/89457 | 11/2001 |
| WO | WO 2003/037905 A1 | 5/2003 |
| WO | WO 03/103686 A1 | 12/2003 |
| WO | WO 2004/033433 | 4/2004 |
| WO | WO 2004/096154 A2 | 11/2004 |
| WO | WO 2005/007651 | 1/2005 |
| WO | WO 2005/014561 | 2/2005 |
| WO | WO 2006/033005 | 3/2006 |
| WO | WO 2006/047344 | 5/2006 |
| WO | WO 2006/047344 A1 | 5/2006 |

(Continued)

OTHER PUBLICATIONS

Cecil Textbook of Medicine, 20th edition (1996), vol. 2, pp. 2050-2057.*

(Continued)

*Primary Examiner* — Shawquia Jackson
(74) *Attorney, Agent, or Firm* — Knobbe, Martens, Olson & Bear LLP

(57) ABSTRACT

Some embodiments include compositions and methods of using or identifying compounds that modulate the activity of the granulocyte colony-stimulating factor receptor (GCFR). Some embodiments include use of compounds to treat certain disorders, such as hematopoietic or neurological disorders.

8 Claims, 12 Drawing Sheets

Specification includes a Sequence Listing.

(56) References Cited

FOREIGN PATENT DOCUMENTS

| WO | WO 2007/004038 | 1/2007 |
|---|---|---|
| WO | WO 2007/004038 A1 | 1/2007 |
| WO | WO 2007/036769 | 4/2007 |
| WO | WO 2007/054783 | 5/2007 |
| WO | WO 2007/062078 | 5/2007 |
| WO | WO 2007/062078 A2 | 5/2007 |
| WO | WO 2007/106564 A2 | 9/2007 |
| WO | WO2009/086303 | 7/2009 |
| WO | WO 2009/103218 | 8/2009 |

OTHER PUBLICATIONS

Cecil Textbook of Medicine, 20th edition (1996), vol. 2, pp. 1992-1996.*
FDA mulls drug to slow late-stage Alzheimer's [online], [retrieved on Sep. 23, 2003]. Retrieved from the Internet, URL; http://www.cnn.com/2003/HEALTH/conditions/09/24/alzheimers.drug.ap/indexhtml>.*
Erickson-Miller, et al. Document No. 141:406144, retrieved from STN; Nov. 11, 2004.*
Amir, et al, Synthesis and antimicrobial activity of pyrazolinones and pyrazoles having benzothiazole moiety, Med. Chem. Res, vol. 21. No. 7, Apr. 10, 2011 (Apr. 10, 2011) pp. 1261-1270.
Bains, W., et al., Silicon chemistry as a novel source of chemical diversity in drug design, Curr. Opin. Drug Discov Devel. 6(4):526-43, 2003.
Database Reaxys [Online] Elsevier Information Systems GmbH, Frankfurt/Main (DE).
Doyle ML, et al., Selective binding and oligomerization of the murine GCSF receptor by a low molecular weight, nonpeptidyl ligand. JBC 278:9426-9434, 2003.
Duffy, KJ., et al., Hydrazinonaphthalene and azonaphthalene thrombopoietin mimics are nonpeptidyl promoters of megakaryocytopoiesis, J Med Chem. Oct. 25, 2001;44(22):3730-45.
Erickson-Miller C, et al., Species specificity and receptor domain interaction of small molecule TPO receptor agonists. ASH 2004 San Diego, poster, 2004.
International Search Report dated Feb. 14, 2013 received in International Application No. PCT/US2012/064706.
Komatsu N, et al, Establishment and characterization of a human leukemic cell line with megakaryocytic features: Dependency on granulocyte-macrophage colony-stimulating factor, interleukin 3, or erythropoietin for growth and survival. Cancer Res 51:341, 1991.
Kumar, P. et al, Design, synthesis and evaluation of 3-methylene-substituted indolinones as antimalarials. Eur J Med Chem. Mar. 2011;46(3):927-33.
Kusano K, et al. A potential therapeutic role for small nonpeptidyl compounds that mimic human GCSF. Blood 103:836-842, 2004.
Lu X, et al., Active conformation of the erythropoietin receptor: Random and cycteine-scanning mutagenesis of the extracellular juxtamembrane and transmembrane domains. JBC 281:7002-7011, 2006.
Monfardini, C. et al., Structure-based design of mimetics for granulocyte-macrophage colony stimulating factor (GM-CSF), Curr Pharm Des. 2002;8(24):2185-99.
Plo I, et al., An activating mutation in the CSF3R gene induces a hereditary chronic neutrophilia. JEM 206:1701-1707, 2009.
Tacke, et al., Sila-substitution—a useful strategy for drug design? Endeavour, New Series, 10:191-197, 1986.
Tamada T, et al., Homodimeric cross-over structure of the human GCSF receptor signaling complex. PNAS 103:3135-3140, 2006.
Tang, PC, et al., Novel indoline-1- or 3,4-dihydroquinoline-1(2H)-substituted carbothiohydrazides as TPO receptor agonists; Bioorg Med Chem Lett. Oct. 1, 2010;20(19):5670-2.
Tian S-S, et al., A small, nonpeptidyl mimics of granulocyte-colony-stimulating factor. Science 281:257-259, 1998.
Tian, SS. Et al, A small, nonpeptidyl mimic of granulocyte-colony-stimulating factor, Science. Jul. 10, 1998;281(5374):257-9.
Liu Guang-Fei et al., Synthesis and structure of the semicarbazone compounds containing pyrazole-ring, Huaxue Xuebao, 2004, 62(7), 697-702.
Toda, Nippon Kagaku Zasshi, (1960) 81:1292-12983.
Leovac, Vaukadin M., et al., Synthesis, Characterization and antitumor activity polymeric copper(II) complexes with semicarbazones of 3-methyl-5-oxo-1-phenyl-3-poyrazolin-4-carboxaldehyde and 5-oxo-3-phenyl-3-pyrazolin-4-carboxaldehyde, J Inorganic Biochem 105(11):1413-1421 (2011).
Registry(STN)[online], Published:Jul. 17, 2006, Searched:Nov. 9, 2017, CAS Reg. No. 893636-31-2, 893636-29-8, 893636-27-6, 893636-13-0, 893636-27-6.
Registry(STN)[online], Published:May 19, 2009, Searched:Oct. 22, 2017, CAS Reg. No. 1147372-72-2.
Registry(STN)[online], Published:Jul. 17, 2006, Searched:Oct. 22, 2017, CAS Reg. No. 893635-91-1.
Registry(STN)[online], Published:Mar. 21, 2010, Searched:Nov. 9, 2017, CAS Reg. No. 1212762-10-1.
Registry(STN)[online], Published:Apr. 13, 2004, Searched:Nov. 9, 2017, CAS Reg. No. 674803-24-8.
Registry(STN)[online], Published:Dec. 7, 2007, Searched:Oct. 22, 2017, CAS Reg. No. 957036-18-9.
Registry(STN)[online], Published:Feb. 18, 2003, Searched:Nov. 9, 2017, CAS Reg. No. 491581-93-2.
Registry(STN)[online], Published:May 31, 2001, Searched:Nov. 9, 2017, CAS Reg. No. 339095-43-1.
Registry(STN)[online], Published:Dec. 24, 2008, Searched:Nov. 19, 2017, CAS Reg. No. 1089343-26-9.
Registry(STN)[online], Published:Oct. 28, 2003, Searched:Nov. 9, 2017, CAS Reg. No. 609822-69-7.
Registry(STN)[online], Published:May 16, 2006, Searched:Nov. 9, 2017, CAS Reg. No. 884427-23-0, 884427-16-1, 884420-36-4, 884420-30-8.
Registry(STN)[online], Published:Jan. 15, 2002, Searched:Nov. 9, 2017, CAS Reg. No. 383167-65-5.
Registry(STN)[online], Published:Dec. 20, 2001, Searched:Nov. 9, 2017, CAS Reg. No. 377065-30-0.
Registry(STN)[online], Published:Jun. 4, 2008, Searched:Nov. 9, 2017, CAS Reg. No. 1025221-25-3.
Registry(STN)[online], Published:Dec. 4, 2007, Searched:Nov. 9, 2017, CAS Reg. No. 956686-60-5.
Registry(STN)[online], Published:May 16, 2006, Searched:Nov. 9, 2017, CAS Reg. No. 884446-24-6, 884446-16-6, 884438-96-4, 884438-59-9, 884417-80-5.
Registry(STN)[online], Published:Apr. 13, 2001, Searched:Nov. 9, 2017, CAS Reg. No. 331238-79-0.
Registry(STN)[online], Published:Jul. 19, 2010, Searched:Nov. 9, 2017, CAS Reg. No. 1232825-98-7.
Registry(STN)[online], Published:Apr. 19, 2002, Searched:Nov. 9, 2017, CAS Reg. No. 406193-78-0.
Registry(STN)[online], Published:Mar. 14, 2001, Searched:Nov. 9, 2017, CAS Reg. No. 327104-62-1.
PubChem, Published:Dec. 6, 2006, CID 11958865.
PubChem, Published:Feb. 28, 2012, CID 56642926.
PubChem, Published:Feb. 6, 2007, CID 12005691.

* cited by examiner

GCSFR Transmembrane Domain

| | | | | | | | | | | | | | | | | | | | | | |
|---|---|---|---|---|---|---|---|---|---|---|---|---|---|---|---|---|---|---|---|---|---|
| Human | E | G | S | E | L | H | I | L | G | L | F | G | L | L | L | L | T | C | L | C | G | T | A | W | L | C | C | S | P |
| Monkey | E | G | S | E | L | H | I | L | G | L | F | G | L | L | L | L | T | C | L | C | G | T | A | W | L | C | C | S | P |
| Rabbit | E | E | S | V | L | H | I | L | L | G | L | S | G | S | L | F | L | L | C | L | C | G | T | T | W | L | C | C | S | P |
| Guinea Pig | G | E | S | E | I | H | I | F | V | A | V | F | G | I | L | I | L | I | C | L | C | G | T | T | W | L | C | C | H | P |
| Mouse | D | P | S | D | L | N | I | F | L | G | I | L | - | C | L | V | L | L | S | T | T | C | V | V | T | W | L | C | C | K | R |

FIG. 5

METHODS AND COMPOSITIONS ASSOCIATED WITH THE GRANULOCYTE COLONY-STIMULATING FACTOR RECEPTOR

CROSS REFERENCE TO RELATED APPLICATIONS

This application is a continuation of U.S. application Ser. No. 14/357,551 filed May 9, 2014 which is the U.S. National Phase of Application No. PCT/US2012/064706 entitled "METHODS AND COMPOSITIONS ASSOCIATED WITH THE GRANULOCYTE COLONY-STIMULATING FACTOR RECEPTOR" filed Nov. 12, 2012 and published in English on May 23, 2013 as WO 2013/074459 which claims the benefit of U.S. Provisional Application No. 61/561,510 filed Nov. 18, 2011, and U.S. Provisional Application No. 61/559,660 filed Nov. 14, 2011, each entitled "METHODS AND COMPOSITIONS ASSOCIATED WITH THE GRANULOCYTE COLONY-STIMULATING FACTOR RECEPTOR" the contents of which are hereby incorporated by reference in their entireties.

REFERENCE TO SEQUENCE LISTING

The present application is being filed along with a Sequence Listing in electronic format. The Sequence Listing is provided as a file entitled LIGAND200C1SEQ.TXT, created Aug. 25, 2016, which is approximately 3 Kb in size. The information in the electronic format of the Sequence Listing is incorporated herein by reference in its entirety.

FIELD OF THE INVENTION

Compositions and methods in the fields of chemistry and medicine are disclosed. Some of the disclosed embodiments are compositions that modulate the activity of the granulocyte colony-stimulating factor receptor (GCFR). Some of the disclosed embodiments are and methods of using or identifying compounds that modulate the activity of the granulocyte colony-stimulating factor receptor (GCFR). Some of the disclosed embodiments include the use of compounds to treat certain disorders, such as hematopoietic or neurological disorders, associated with the granulocyte colony-stimulating factor receptor (GCFR).

BACKGROUND OF THE INVENTION

Granulocyte colony-stimulating factor (GCSF) is one of the hematopoietic growth factors with multifunctional activities. As a glycoprotein, GCSF plays important regulatory functions in the processes of maturation, proliferation, differentiation, and functional activation of granulocyte precursors and mature granulocytes in the bone marrow. It is able to augment white blood cell production when bone marrow dysfunction exists. Recombinant DNA technology has made it possible to clone the genes responsible for GCSF and to develop pharmaceutical products to treat a number of human hematopoietic conditions and disorders such as neutropenia and hematopietic stem cell transplantation.

Human GCSF (hGCSF) protein has a molecular mass of 19.6 kDa and exerts its biological functions through binding to the human GCSF receptor (hGCSFR), a single transmembrane protein with a large extracellular region that consists of an immunoglobulin-like (Ig-like) domain, a cytokine receptor homology (CRH) domain, and three fibronectin type III domains. Binding of GCSF to the extracellular Ig-like and CRH domains of the receptor triggers receptor homodimerization with a 2:2 stoichiometry of hGCSF/hGCSFR (Tamada T, et al. 2006 Homodimeric cross-over structure of the human GCSF receptor signaling complex. PNAS 103:3135-3140). The dimerization results in activation of intracellular Janus tyrosine kinase-signal transducers and activators of transcription (Jak-Stat) type signaling cascade. The signaling transfer of hematopoietic factor receptors from extracellular region to intracellular cascades has been suggested to be via conformational changes of the receptor dimer in TM domains. It has been demonstrated that the dimeric erythropoietin (EPO) receptor can be activated by mutations at the TM domain in the absence of the natural ligand EPO, a hematopoietic growth factor regulating red blood cell production (Lu X, et al. 2006 Active conformation of the erythropoietin receptor: Random and cycteine-scanning mutagenesis of the extracellular juxtamembrane and transmembrane domains. JBC 281:7002-7011). Patients with mutations in TM domain of hGCSFR have experienced chronic neutrophilia due to the receptor constitutive activation (Plo I, et al. 2009 An activating mutation in the CSF3R gene induces a hereditary chronic neutrophilia. JEM 206:1701-1707).

Development of bioengineered EPO and GCSF targeted binding sites of the natural ligands have been successful, while development of a protein-based thrombopoietin (TPO) drug has failed due to drug-related increase in antibody production against endogenous TPO. A peptide-based TPO mimic molecule, romiplostim, recently received FDA approval, although the risk of drug-related antibody development is to be monitored in longer term use. Discovery efforts to find small molecules targeting the same site have not been fruitful. Eltrombopag is the first FDA approved small molecule drug in the hematopoietic growth factor field for the treatment of thrombocytopenia. Different from romiplostim that competes with endogenous TPO for the same binding site of TPO receptor, eltrombopag activates TPO receptor most likely by interacting with the TM domain and, as a result, its activity is additive to that of endogenous TPO. Eltrombopag showed a unique species-specific TPO receptor activation that requires histidine-499, and partially activated a mouse GCSF receptor where a cysteine residue in the TM domain was mutated to histidine (Erickson-Miller C, et al. 2004 Species specificity and receptor domain interaction of small molecule TPO receptor agonists. ASH 2004 San Diego, poster). Several classes of compounds have been reported to activate the TPO receptor. For example, WO 2004/033433, WO 2007/062078, WO 2006/047344, WO 01/89457, WO 2009/103218, U.S. Pat. No. 7,026,334, WO 2005/014561, WO 2005/007651, WO 2006/033005, WO 2007/004038, WO 2007/036769, and WO 2007/054783.

A small molecule that selectively activates mouse GCSF receptor has been identified. (Tian S-S, et al. 1998 A small, nonpeptidyl mimics of granulocyte-colony-stimulating factor. Science 281:257-259). This molecule is reported to not directly compete with GCSF, although it seems to bind to the extracellular region of mouse GCSF receptor. (Doyle M L, et al. 2003 Selective binding and oligomerization of the murine GCSF receptor by a low molecular weight, nonpeptidyl ligand. JBC 278:9426-9434). A class of small molecules have been reported to activate the both mouse and human GCSF receptors and the site of action is not suggested (Kusano K, et al. 2004 A potential therapeutic role for small nonpeptidyl compounds that mimic human GCSF.

Blood 103:836-842; Tokizawa M, et al. 2004 Imidazole derivatives of their salts. U.S. Pat. No. 6,737,434).

SUMMARY OF THE INVENTION

Compositions that modulate the activity of the granulocyte colony-stimulating factor receptor (GCFR) are disclosed. Methods of using and methods of identifying compounds that modulate the activity of the granulocyte colony-stimulating factor receptor (GCFR) are disclosed. Other embodiments are disclosed that include use of compounds to treat certain disorders, such as hematopoietic or neurological disorders.

Some embodiments include a compound of Formula (I), (II), (III), or (IV):

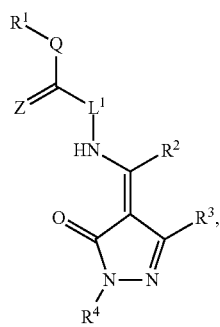
(I)

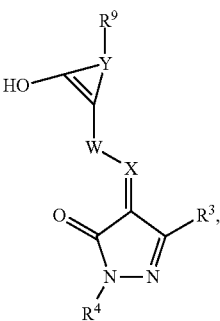
(II)

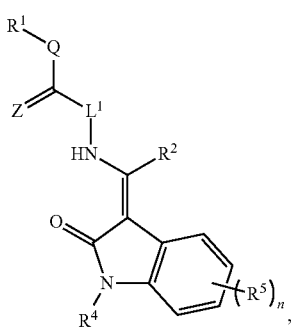
(III)

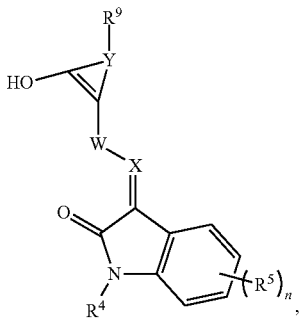
(IV)

a tautomer thereof, or a pharmaceutically acceptable salt thereof, wherein:

$R^1$ is selected from hydrogen, $OR^6$, $NO_2$, CN, $NR^6R^7$, $CO_2R^6$, $C(=O)NR^6R^7$, $SO_3R^6$, $SO_2NR^6R^8$, an optionally substituted $C_1$-$C_6$ alkyl, an optionally substituted $C_2$-$C_6$ alkenyl, an optionally substituted $C_2$-$C_6$ alkynyl, an optionally substituted $C_1$-$C_6$ heteroalkyl, an optionally substituted $C_3$-$C_6$ cycloalkyl, an optionally substituted $C_3$-$C_6$ cycloalkenyl, an optionally substituted $C_2$-$C_6$ heterocyclyl, an optionally substituted arylalkyl, an optionally substituted aryl, and an optionally substituted heteroaryl;

$R^2$ and $R^3$ are independently selected from hydrogen, an optionally substituted $C_1$-$C_6$ alkyl, an optionally substituted $C_2$-$C_6$ alkenyl, an optionally substituted $C_2$-$C_6$ alkynyl, an optionally substituted $C_1$-$C_6$ heteroalkyl, an optionally substituted $C_3$-$C_8$ cycloalkyl, an optionally substituted $C_3$-$C_8$ cycloalkenyl, an optionally substituted $C_1$-$C_6$ heterocycle, an optionally substituted aryl, and an optionally substituted heteroaryl;

$R^4$ is selected from hydrogen, an optionally substituted $C_1$-$C_6$ alkyl, an optionally substituted $C_2$-$C_6$ alkenyl, an optionally substituted $C_2$-$C_6$ alkynyl, an optionally substituted $C_1$-$C_6$ heteroalkyl, an optionally substituted $C_3$-$C_8$ cycloalkyl, an optionally substituted $C_3$-$C_8$ cycloalkenyl, an optionally substituted $C_1$-$C_6$ heterocycle, an optionally substituted aryl, an optionally substituted heteroaryl, an optionally substituted arylalkyl, an optionally substituted arylalkenyl, an optionally substituted arylalkynyl, and an optionally substituted heteroarylalkyl;

$R^5$ is selected from hydrogen, halogen, $NO_2$, CN, $CF_3$, $OR^6$, $CO_2R^6$, $C(=O)NR^6R^7$, $SO_3R^6$, and $SO_2NR^6R^8$, an optionally substituted aryl, an optionally substituted $C_1$-$C_6$ alkyl, and an optionally substituted $C_1$-$C_6$ heteroalkyl;

$R^6$ is selected from hydrogen, an optionally substituted $C_1$-$C_6$ alkyl, a $C_1$-$C_6$ heteroalkyl, an optionally substituted aryl, and an optionally substituted heteroaryl;

$R^7$ is selected from hydrogen, $C(=O)R^8$, $C(=O)NHR^8$, an optionally substituted $C_1$-$C_6$ alkyl, and an optionally substituted $C_1$-$C_6$ heteroalkyl; or —$NR^6R^7$ is an optionally substituted non-aromatic heterocycle linked through a ring nitrogen;

$R^8$ is selected from hydrogen, an optionally substituted $C_1$-$C_6$ alkyl, and an optionally substituted $C_1$-$C_6$ heteroalkyl;

$R^9$ is selected from hydrogen, an optionally substituted $C_1$-$C_6$ alkyl, an optionally substituted $C_2$-$C_6$ alkenyl, an optionally substituted $C_2$-$C_6$ alkynyl, an optionally substituted $C_1$-$C_6$ heteroalkyl, an optionally substituted $C_3$-$C_8$ cycloalkyl, an optionally substituted $C_3$-$C_8$ cycloalkenyl, an optionally substituted $C_1$-$C_6$ heterocycle, an optionally substituted heteroaryl, an optionally substituted arylalkyl, an optionally substituted arylalkenyl, an optionally substituted arylalkynyl, an optionally substituted heteroarylalkyl, an optionally substituted heteroarylalkenyl, and an optionally substituted heteroarylalkynyl;

Q is selected from the group consisting of $NR^6$, an optionally substituted $C_1$-$C_6$ alkyl, an optionally substituted $C_3$-$C_8$ cycloalkyl, an optionally substituted $C_1$-$C_6$ heteroalkyl, and an optionally substituted non-aromatic heterocycle;

$L^1$ is selected from NH and $CHR^2$;

W is selected from O (oxygen) and NH;

X is N (nitrogen) or $CR^2$;

Y is selected from an optionally substituted $C_1$-$C_6$ alkyl, $C_2$-$C_6$ alkenyl, an optionally substituted $C_1$-$C_6$ heteroalkyl, an optionally substituted $C_1$-$C_6$ heteroalkenyl, an optionally substituted phenylalkenyl, and an optionally substituted heterocyclealkenyl;

Z is O (oxygen) or S (sulfur);

n is 1, 2 or 3; and provided that if $R^2$ is methyl, $R^4$ is phenyl, $L^1$ is NH, and Q is N-Ph-$R^1$ in Formula I and III, $R^1$ of Formula I and III is not selected from the group of halogen, alkyl, substituted alkyl, carboxylic acid, and carboxylic esters.

In some embodiments, the compound is a GCSF receptor agonist.

In some embodiments, the compound is a GCSF receptor partial agonist.

Some embodiments include pharmaceutical compositions comprising a compound provided herein and a pharmaceutically acceptable excipient.

Some embodiments include methods of treating a hematopoietic or neurological disorder comprising administering an effective amount of a compound provided herein to a subject in need thereof.

In some embodiments, the disorder is selected from the group consisting of granulocytopenia, neutropenia, amyotrophic lateral sclerosis, multiple sclerosis, multiple dystrophy, and spinal cord injury.

In some embodiments, the compound is administered in combination with an additional therapeutic regimen. In some embodiments, the additional therapeutic regimen is selected from the group consisting of chemotherapy, bone marrow transplantation, and radiation therapy.

Some embodiments include methods of treating a hematopoietic or neurological disorder comprising administering an effective amount of a compound of Formula (V) or (VI) to a subject in need thereof, wherein Formula (V) or (VI) having the structure:

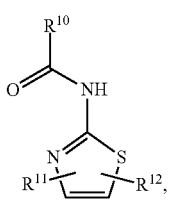
(V)

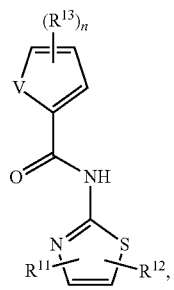
(VI)

or pharmaceutically acceptable salt thereof, wherein:

$R^{10}$ is selected from an optionally substituted $C_1$-$C_{12}$ alkyl, an optionally substituted $C_1$-$C_{12}$ heteroalkyl, an optionally substituted $C_2$-$C_{12}$ heteroalkenyl, an optionally substituted $C_2$-$C_{12}$ heteroalkynyl, an optionally substituted $C_1$-$C_{12}$ cycloalkyl; an optionally substituted $C_1$-$C_6$ heterocycloalkyl, an optionally substituted heteroarylalkyl, an optionally substituted arylheteroalkyl, an optionally substituted heteroarylheteroalkyl, $OR^{14}$, $SR^{14}$, and $NR^8R^{14}$;

$R^{11}$ is selected from hydrogen, halogen, an optionally substituted $C_1$-$C_6$ alkyl, an optionally substituted $C_1$-$C_6$ heteroalkyl, an optionally substituted $C_3$-$C_8$ cycloalkyl, and an optionally substituted $C_1$-$C_6$ heterocycle;

$R^{12}$ is selected from an optionally substituted $C_1$-$C_6$ heteroalkyl, an optionally substituted $C_3$-$C_8$ cycloalkyl, an optionally substituted $C_1$-$C_6$ heterocycle, an optionally substituted aryl, and an optionally substituted heteroaryl;

$R^{13}$ is selected from hydrogen, halogen, an optionally substituted $C_1$-$C_8$ alkyl, an optionally substituted $C_1$-$C_8$ heteroalkyl, an optionally substituted $C_2$-$C_8$ heteroalkenyl, an optionally substituted $C_3$-$C_8$ cycloalkyl, an optionally substituted $C_1$-$C_6$ heterocycloalkyl, $OR^{14}$, $SR^{14}$, and $NR^8R^{14}$;

$R^{14}$ is selected from an optionally substituted aryl and an optionally substituted heteroaryl;

V is selected from CH=CH, N=CH, CH=N, NH, O (oxygen), and S (sulfur); and n is 1, 2 or 3.

In some embodiments, the disorder is selected from the group consisting of granulocytopenia, neutropenia, amyotrophic lateral sclerosis, multiple sclerosis, multiple dystrophy, and spinal cord injury.

In some embodiments, the compound is administered in combination with an additional therapeutic regimen. In some embodiments, the additional therapeutic regimen is selected from the group consisting of chemotherapy, bone marrow transplantation, and radiation therapy.

Some embodiments include methods for identifying a therapeutic compound comprising: contacting a target cell with a test compound comprising a GCSF receptor agonist, wherein the target cell comprises a mutant GCSF receptor protein; and determining whether the test compound significantly changes the level of activity of the mutant GCSF receptor in the target cell. Some such embodiments also include comparing the level of activity of the mutant GCSF receptor in the target cell to the level of activity of a wild type GCSF receptor protein in a cell contacted with the test compound. Some such embodiments also include determining whether the level of activity of the mutant GCSF receptor in the target cell contacted with the test compound is less than the level of activity of the wild type GCSF receptor protein in a cell contacted with the test compound.

In some embodiments, the mutant GCSF receptor protein comprises a mutation in the transmembrane domain of the protein or a mutation proximal to the transmembrane domain of the protein. In some such embodiments, the mutation is selected from the group consisting of a substitution at the residue corresponding to his-627 of the human GCSF receptor protein, and a substitution at the residue corresponding to Asp-602 of the mouse GCSF receptor protein.

In some embodiments, the mutant GCSF receptor comprises a mutant human GCSF receptor.

In some embodiments, the cell comprises a mammalian cell. In some embodiments, the cell comprises a human cell. In some embodiments, the cell is not a blood cell.

BRIEF DESCRIPTION OF THE DRAWINGS

FIG. 5 is a schematic comparison of amino acid sequences of the transmembrane domain of GCSFR from various species. Compound X is active in cells expressing human and monkey GCSFR, but not mouse, guinea pig, and rabbit receptors.

FIG. 6A: left panel: hGCSFR; right panel: hGCSFR-H627N. FIG. 6B: left panel: mGCSFR; right panel: mGCSFR-N607H.

DETAILED DESCRIPTION

Figure 1A:
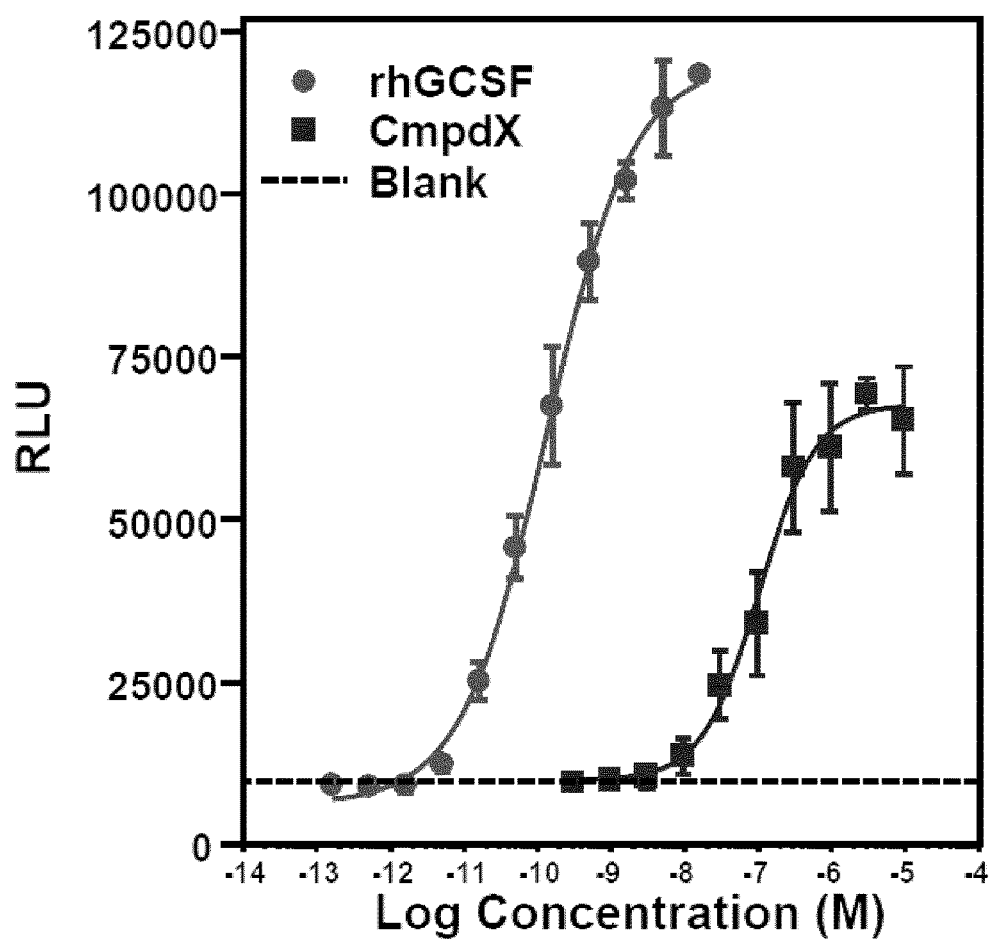
FIG. 1A is a graph of relative luciferase activity in HepG2 cells transfected with a STAT3-responsive reporter construct and treated with various concentrations of rhGCSF, Compound X, or control.

Some embodiments include compositions and methods of using or identifying compounds that modulate the activity of the granulocyte colony-stimulating factor receptor (GCFR). Some embodiments include use of compounds to treat certain disorders, such as hematopoietic or neurological disorders.

Certain embodiments include a compound of Formula (I), (II), (III), or (IV):

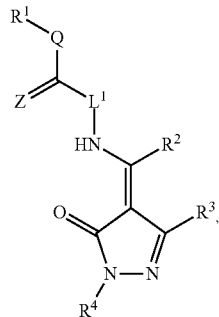

(I)

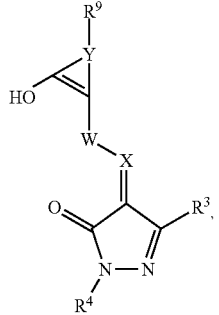

(II)

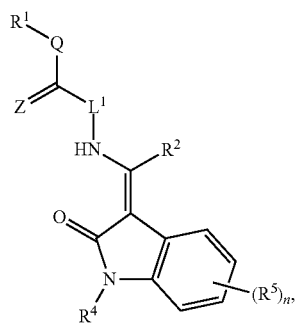

(III)

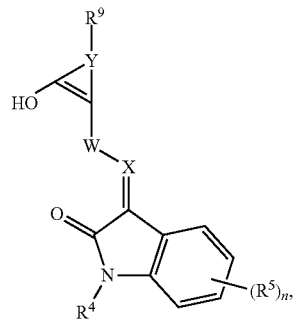

(IV)

a tautomer thereof, or a pharmaceutically acceptable salt thereof, wherein:

$R^1$ is selected from hydrogen, $OR^6$, $NO_2$, CN, $NR^6R^7$, $CO_2R^6$, $C(=O)NR^6R^7$, $SO_3R^6$, $SO_2NR^6R^8$, an optionally substituted $C_1$-$C_6$ alkyl, an optionally substituted $C_2$-$C_6$ alkenyl, an optionally substituted $C_2$-$C_6$ alkynyl, an optionally substituted $C_1$-$C_6$ heteroalkyl, an optionally substituted $C_3$-$C_6$ cycloalkyl, an optionally substituted $C_3$-$C_6$ cycloalkenyl, an optionally substituted $C_2$-$C_6$ heterocyclyl, an optionally substituted arylalkyl, an optionally substituted aryl, and an optionally substituted heteroaryl;

$R^2$ and $R^3$ are independently selected from hydrogen, an optionally substituted $C_1$-$C_6$ alkyl, an optionally substituted $C_2$-$C_6$ alkenyl, an optionally substituted $C_2$-$C_6$ alkynyl, an optionally substituted $C_1$-$C_6$ heteroalkyl, an optionally substituted $C_3$-$C_8$ cycloalkyl, an optionally substituted $C_3$-$C_8$ cycloalkenyl, an optionally substituted $C_1$-$C_6$ heterocycle, an optionally substituted aryl, and an optionally substituted heteroaryl;

$R^4$ is selected from hydrogen, an optionally substituted $C_1$-$C_6$ alkyl, an optionally substituted $C_2$-$C_6$ alkenyl, an optionally substituted $C_2$-$C_6$ alkynyl, an optionally substituted $C_1$-$C_6$ heteroalkyl, an optionally substituted $C_3$-$C_8$ cycloalkyl, an optionally substituted $C_3$-$C_8$ cycloalkenyl, an optionally substituted $C_1$-$C_6$ heterocycle, an optionally substituted aryl, an optionally substituted heteroaryl, an optionally substituted arylalkyl, an optionally substituted arylalkenyl, an optionally substituted arylalkynyl, and an optionally substituted heteroarylalkyl;

$R^5$ is selected from hydrogen, halogen, $NO_2$, CN, $CF_3$, $OR^6$, $CO_2R^6$, $C(=O)NR^6R^7$, $SO_3R^6$, and $SO_2NR^6R^8$, an optionally substituted aryl, an optionally substituted $C_1$-$C_6$ alkyl, and an optionally substituted $C_1$-$C_6$ heteroalkyl;

$R^6$ is selected from hydrogen, an optionally substituted $C_1$-$C_6$ alkyl, a $C_1$-$C_6$ heteroalkyl, an optionally substituted aryl, and an optionally substituted heteroaryl;

$R^7$ is selected from hydrogen, $C(=O)R^8$, $C(=O)NHR^8$, an optionally substituted $C_1$-$C_6$ alkyl, and an optionally substituted $C_1$-$C_6$ heteroalkyl; or —$NR^6R^7$ is an optionally substituted non-aromatic heterocycle linked through a ring nitrogen;

$R^8$ is selected from hydrogen, an optionally substituted $C_1$-$C_6$ alkyl, and an optionally substituted $C_1$-$C_6$ heteroalkyl;

$R^9$ is selected from hydrogen, an optionally substituted $C_1$-$C_6$ alkyl, an optionally substituted $C_2$-$C_6$ alkenyl, an optionally substituted $C_2$-$C_6$ alkynyl, an optionally substituted $C_1$-$C_6$ heteroalkyl, an optionally substituted $C_3$-$C_8$ cycloalkyl, an optionally substituted $C_3$-$C_8$ cycloalkenyl, an optionally substituted $C_1$-$C_6$ heterocycle, an optionally substituted heteroaryl, an optionally substituted arylalkyl, an optionally substituted arylalkenyl, an optionally substituted arylalkynyl, an optionally substituted heteroarylalkyl, an optionally substituted heteroarylalkenyl, and an optionally substituted heteroarylalkynyl;

Q is selected from the group consisting of $NR^6$, an optionally substituted $C_1$-$C_6$ alkyl, an optionally substituted $C_3$-$C_8$ cycloalkyl, an optionally substituted $C_1$-$C_6$ heteroalkyl, and an optionally substituted non-aromatic heterocycle;

$L^1$ is selected from NH and $CHR^2$;

W is selected from O (oxygen) and NH;

X is N (nitrogen) or $CR^2$;

Y is selected from an optionally substituted $C_1$-$C_6$ alkyl, $C_2$-$C_6$ alkenyl, an optionally substituted $C_1$-$C_6$ heteroalkyl, an optionally substituted $C_1$-$C_6$ heteroalkenyl, an optionally substituted phenylalkenyl, and an optionally substituted heterocyclealkenyl;

Z is O (oxygen) or S (sulfur);

n is 1, 2 or 3; and provided that if $R^2$ is methyl, $R^4$ is phenyl, $L^1$ is NH, and Q is N-Ph-$R^1$ in Formula I and III, $R^1$ of Formula I and III is not selected from the group of halogen, alkyl, substituted alkyl, carboxylic acid, and carboxylic esters.

Certain embodiments include methods of treating a hematopoietic or neurological disorder comprising administering an effective amount of a compound of Formula (V) or (VI) to a subject in need thereof, wherein Formula (V) or (VI): having the structure:

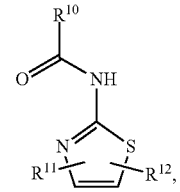

(V)

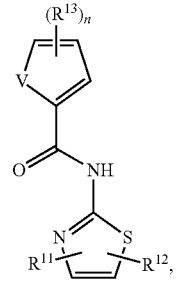

(VI)

or pharmaceutically acceptable salt thereof, wherein:

$R^{10}$ is selected from an optionally substituted $C_1$-$C_{12}$ alkyl, an optionally substituted $C_1$-$C_{12}$ heteroalkyl, an optionally substituted $C_2$-$C_{12}$ heteroalkenyl, an optionally substituted $C_2$-$C_{12}$ heteroalkynyl, an optionally substituted $C_1$-$C_{12}$ cycloalkyl; an optionally substituted $C_1$-$C_6$ heterocycloalkyl, an optionally substituted heteroarylalkyl, an optionally substituted arylheteroalkyl, an optionally substituted heteroarylheteroalkyl, $OR^{14}$, $SR^{14}$, and $NR^8R^{14}$;

$R^{11}$ is selected from hydrogen, halogen, an optionally substituted $C_1$-$C_6$ alkyl, an optionally substituted $C_1$-$C_6$ heteroalkyl, an optionally substituted $C_3$-$C_8$ cycloalkyl, and an optionally substituted $C_1$-$C_6$ heterocycle;

$R^{12}$ is selected from an optionally substituted $C_1$-$C_6$ heteroalkyl, an optionally substituted $C_3$-$C_8$ cycloalkyl, an optionally substituted $C_1$-$C_6$ heterocycle, an optionally substituted aryl, and an optionally substituted heteroaryl;

$R^{13}$ is selected from hydrogen, halogen, an optionally substituted $C_1$-$C_8$ alkyl, an optionally substituted $C_1$-$C_8$ heteroalkyl, an optionally substituted $C_2$-$C_8$ heteroalkenyl, an optionally substituted $C_3$-$C_8$ cycloalkyl, an optionally substituted $C_1$-$C_6$ heterocycloalkyl, $OR^{14}$, $SR^{14}$, and $NR^8R^{14}$;

$R^{14}$ is selected from an optionally substituted aryl and an optionally substituted heteroaryl;

V is selected from CH=CH, N=CH, CH=N, NH, O (oxygen), and S (sulfur); and n is 1, 2 or 3.

In certain embodiments, a compound of Formula I, II, III, IV, V, and VI is a GCSFR agonist. In some such embodiments, a compound of Formula I, II, III, IV, V, and VI is a hGCSFR agonist.

Compounds provided herein can have a variety of functions. For example, in certain embodiments, a compound of Formula I, II, III, IV, V, and VI is a GCSFR partial agonist. In some such embodiments, a compound of Formula I, II, III, IV, V, and VI is a hGCSFR partial agonist. In certain embodiments provide a selective GCSFR modulator. In certain embodiments provide a selective GCSF receptor agonist. In certain embodiments provide a selective GCSFR partial agonist. In certain embodiments provide a selective GCSF receptor binding compound. In certain embodiments, selective GCSFR modulators are agonists, partial agonists, and/or antagonists for the GCSF receptor.

Definitions

Unless specific definitions are provided, the nomenclatures utilized in connection with, and the laboratory procedures and techniques of, analytical chemistry, synthetic organic chemistry, and medicinal and pharmaceutical chemistry described herein are those known in the art. Standard chemical symbols are used interchangeably with the full names represented by such symbols. Thus, for example, the terms "hydrogen" and "H" are understood to have identical meaning. Standard techniques may be used for chemical syntheses, chemical analyses, pharmaceutical preparation, formulation, and delivery, and treatment of patients. Standard techniques may be used for recombinant DNA, oligonucleotide synthesis, and tissue culture and transformation (e.g., electroporation, lipofection). Reactions and purification techniques may be performed e.g., using kits according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)), which is incorporated herein by reference in its entirety for any purpose.

The term "selective binding compound" refers to a compound that selectively binds to any portion of one or more target.

The term "binding-site selective hGCSFR activators" refers to a compound that selectively binds to a hGCSF receptor at or near TM domain.

The term "selectively binds" refers to the ability of a selective binding compound to bind to a target receptor with greater affinity than it binds to a non-target receptor. In certain embodiments, selective binding refers to binding to a target with an affinity that is at least 10, 50, 100, 250, 500, or 1000 times greater than the affinity for a non-target.

The term "target receptor" refers to a receptor or a portion of a receptor capable of being bound by a selective binding compound. In certain embodiments, a target receptor is a hGCSF receptor.

The term "modulator" refers to a compound that alters an activity. For example, a modulator may cause an increase or decrease in the magnitude of a certain activity compared to the magnitude of the activity in the absence of the modulator. In certain embodiments, a modulator is an inhibitor, which decreases the magnitude of one or more activities. In certain embodiments, an inhibitor completely prevents one or more biological activities. In certain embodiments, a modulator is an activator, which increases the magnitude of at least one activity. In certain embodiments the presence of a modulator results in a activity that does not occur in the absence of the modulator.

The term "selective modulator" refers to a compound that selectively modulates a target activity.

The term "selective hGCSFR modulator" refers to a compound that selectively modulates hGCSFR activity. The term selective hGCSFR modulator includes, but is not limited to "hGCSF mimic" which refers to a compound, the presence of which results in similar GCSF activity.

The term "selectively modulates" refers to the ability of a selective modulator to modulate a target activity to a greater extent than it modulates a non-target activity.

The term "target activity" refers to a biological activity capable of being modulated by a selective modulator. Certain exemplary target activities include, but are not limited to, binding affinity, signal transduction, enzymatic activity, the proliferation and/or differentiation of progenitor cells, generation of white blood cells, and alleviation of symptoms of a disease or condition.

The term "GCSF activity" refers to a biological activity that results, either directly or indirectly from the presence of GCSF. Example GCSF activities include, but are not limited to, proliferation and or differentiation of progenitor cells to produce white blood cells; hematopoiesis; growth and/or development of glial cells; repair of nerve cells; and alleviation of granulocytopenia.

The term "receptor mediated activity" refers to any biological activity that results, either directly or indirectly, from binding of a ligand to a receptor.

The term "agonist" refers to a compound, the presence of which results in a biological activity of a receptor that is the same as the biological activity resulting from the presence of a naturally occurring ligand for the receptor.

The term "partial agonist" refers to a compound, the presence of which results in a biological activity of a receptor that is of the same type as that resulting from the presence of a naturally occurring ligand for the receptor, but of a lower magnitude.

The term "antagonist" refers to a compound, the presence of which results in a decrease in the magnitude of a biological activity of a receptor. In certain embodiments, the presence of an antagonist results in complete inhibition of a biological activity of a receptor.

The term "alkyl" refers to a branched or unbranched fully saturated acyclic aliphatic hydrocarbon group. An alkyl may be branched or straight chain. Alkyls may be substituted or unsubstituted. Alkyls include, but are not limited to, methyl, ethyl, propyl, isopropyl, butyl, isobutyl, tertiary butyl, pentyl, hexyl, and the like, each of which may be optionally substituted.

In certain embodiments, an alkyl comprises 1 to 20 carbon atoms (whenever it appears herein, a numerical range such as "1 to 20" refers to each integer in the given range; e.g., "1 to 20 carbon atoms" means that an alkyl group may comprise only 1 carbon atom, 2 carbon atoms, 3 carbon atoms, etc., up to and including 20 carbon atoms, although the term "alkyl" also includes instances where no numerical range of carbon atoms is designated). An alkyl may be designated as "$C_1$-$C_6$ alkyl" or similar designations. By way of example only, "$C_1$-$C_4$ alkyl" indicates an alkyl having one, two, three, or four carbon atoms, e.g., the alkyl is selected from methyl, ethyl, propyl, iso-propyl, butyl, iso-butyl, sec-butyl, and tert-butyl.

The term "alkenyl" used herein refers to a monovalent straight or branched chain aliphatic hydrocarbon radical of from two to twenty carbon atoms containing at least one carbon-carbon double bond including, but not limited to, 1-propenyl, 2-propenyl, 2-methyl-1-propenyl, 1-butenyl, 2-butenyl, and the like. In certain embodiments, an alkenyl comprises 2 to 20 carbon atoms (whenever it appears herein, a numerical range such as "2 to 20" refers to each integer in the given range; e.g., "2 to 20 carbon atoms" means that an alkenyl group may comprise only 2 carbon atoms, 3 carbon atoms, etc., up to and including 20 carbon atoms, although the term "alkenyl" also includes instances where no numerical range of carbon atoms is designated). An alkenyl may be designated as "$C_2$-$C_6$ alkenyl" or similar designations. By way of example only, "$C_2$-$C_4$ alkenyl" indicates an alkenyl having two, three, or four carbon atoms, e.g., the alkenyl is selected from ethenyl, propenyl, and butenyl.

The term "alkynyl" used herein refers to a monovalent straight or branched chain aliphatic hydrocarbon radical of from two to twenty carbon atoms containing at least one carbon-carbon triple bond including, but not limited to, 1-propynyl, 1-butynyl, 2-butynyl, and the like. In certain embodiments, an alkynyl comprises 2 to 20 carbon atoms (whenever it appears herein, a numerical range such as "2 to 20" refers to each integer in the given range; e.g., "2 to 20 carbon atoms" means that an alkynyl group may comprise only 2 carbon atoms, 3 carbon atoms, etc., up to and including 20 carbon atoms, although the term "alkynyl" also includes instances where no numerical range of carbon atoms is designated). An alkynyl may be designated as "$C_2$-$C_6$ alkynyl" or similar designations. By way of example only, "$C_2$-$C_4$ alkynyl" indicates an alkenyl having two, three, or four carbon atoms, e.g., the alkenyl is selected from ethynyl, propynyl, and butynyl.

The term "cycloalkyl" used herein refers to saturated aliphatic ring system radical having three to twenty carbon atoms. A cycloalkyl refers to monocyclic and polycyclic saturated aliphatic ring system including, but not limited to, cyclopropyl, cyclopentyl, cyclohexyl, cycloheptyl, bicyclo[4.4.0]decanyl, bicyclo[2.2.1]heptanyl, adamantyl, norbornyl, and the like. In certain embodiments, a cycloalkyl comprises 3 to 20 carbon atoms (whenever it appears herein, a numerical range such as "3 to 20" refers to each integer in the given range; e.g., "3 to 20 carbon atoms" means that a cycloalkyl group may comprise only 3 carbon atoms, etc., up to and including 20 carbon atoms, although the term "cycloalkyl" also includes instances where no numerical range of carbon atoms is designated). A cycloalkyl may be designated as "$C_3$-$C_7$ cycloalkyl" or similar designations. By way of example only, "$C_3$-$C_6$ cycloalkyl" indicates an alkenyl having two, three, four, five or six carbon atoms, e.g., the cycloalkyl is selected from cyclopropyl, cyclobutyl, cyclopentyl, and cyclohexyl.

The term "cycloalkenyl" used herein refers to aliphatic ring system radical having three to twenty carbon atoms having at least one carbon-carbon double bond in the ring. A cycloalkenyl refers to monocyclic and polycyclic unsaturated aliphatic ring system including, but are not limited to, cyclopropenyl, cyclopentenyl, cyclohexenyl, cycloheptenyl, bicyclo[3.1.0]hexyl, norbornylenyl, 1,1'-bicyclopentenyl, and the like. In certain embodiments, a cycloalkenyl comprises 3 to 20 carbon atoms (whenever it appears herein, a numerical range such as "3 to 20" refers to each integer in the given range; e.g., "3 to 20 carbon atoms" means that a cycloalkenyl group may comprise only 3 carbon atoms, etc., up to and including 20 carbon atoms, although the term "cycloalkenyl" also includes instances where no numerical range of carbon atoms is designated). A cycloalkenyl may be designated as "$C_3$-$C_7$ cycloalkenyl" or similar designations. By way of example only, "$C_3$-$C_6$ cycloalkenyl" indicates an alkenyl having two, three, four, five or six carbon atoms, e.g., the cycloalkyl is selected from cyclopropenyl, cyclobutenyl, cyclopentenyl, and cyclohexenyl.

The term "heteroalkyl" refers to a group comprising an alkyl and one or more heteroatoms. Certain heteroalkyls are acylalkyls, in which the one or more heteroatoms are within an alkyl chain. Examples of heteroalkyls include, but are not limited to, $CH_3C(=O)CH_2-$, $CH_3C(=O)CH_2CH_2-$, $CH_3CH_2C(=O)CH_2CH_2-$, $CH_3C(=O)CH_2CH_2CH_2-$, $CH_3OCH_2CH_2-$, $CH_3NHCH_2-$, and the like.

The term "alkoxy" used herein refers to straight or branched chain alkyl radical covalently bonded to the parent molecule through an —O— linkage. Examples of alkoxy groups include, but are not limited to, methoxy, ethoxy, propoxy, isopropoxy, butoxy, n-butoxy, sec-butoxy, t-butoxy and the like. An alkoxy may be designated as "$C_1$-$C_6$ alkoxy" or similar designations. By way of example only, "$C_1$-$C_4$ alkoxy" indicates an alkyl having one, two, three, or four carbon atoms, e.g., the alkoxy is selected from methoxy, ethoxy, propoxy, iso-propoxy, butoxy, iso-butoxy, sec-butoxy, and tert-butoxy.

The term "olefin" refers to a C=C bond.

The term "alkylideneamino" used herein refers to a moiety of from one to twenty carbon atoms containing at least one carbon-nitrogen double bond where the moiety is connected to the main group through the nitrogen, including, but not limited to, methylideneamino, ethylideneamino, methylethylideneamino, propylideneamino, 1-methylpropylideneaminyl, 2-methylpropylideneamino, butylideneamino, 1-methylbutylideneamino, 2-methylbutylideneamino, cyclopropylideneamino, cyclobutylideneamino, cyclopentylideneamino, cyclohexylideneamino and the like.

The term "carbocycle" refers to a group comprising a covalently closed ring, wherein each of the atoms forming the ring is a carbon atom. Carbocyclic rings may be formed by three, four, five, six, seven, eight, nine, or more than nine carbon atoms. Carbocycles may be optionally substituted.

The term "heterocycle" refers to a group comprising a covalently closed ring wherein at least one atom forming the ring is a heteroatom. Heterocyclic rings may be formed by three, four, five, six, seven, eight, nine, or more than nine atoms. Any number of those atoms may be heteroatoms (i.e., a heterocyclic ring may comprise one, two, three, four, five, six, seven, eight, nine, or more than nine heteroatoms). In heterocyclic rings comprising two or more heteroatoms, those two or more heteroatoms may be the same or different from one another. Heterocycles may be optionally substituted. Binding to a heterocycle can be at a heteroatom or via a carbon atom. For example, binding for benzo-fused derivatives, may be via a carbon of the benzenoid ring. Examples of heterocycles include, but are not limited to the following:

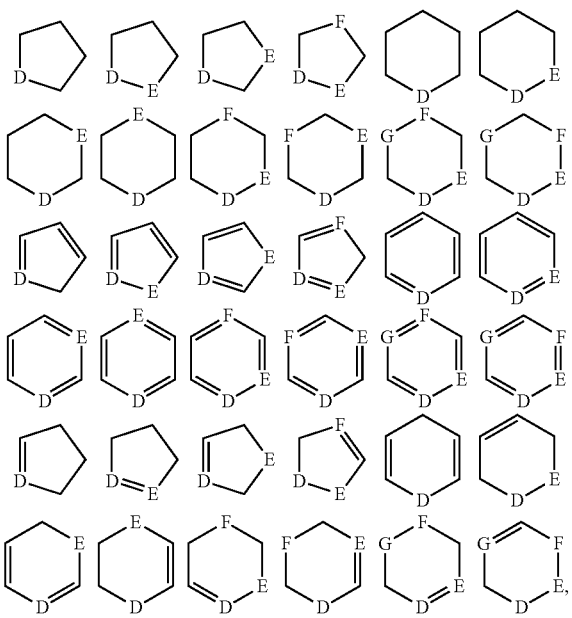

wherein D, E, F, and G independently represent a heteroatom. Each of D, E, F, and G may be the same or different from one another.

The term "heteroatom" refers to an atom other than carbon or hydrogen. Heteroatoms are typically independently selected from oxygen, sulfur, nitrogen, and phosphorus, but are not limited to those atoms. In embodiments in which two or more heteroatoms are present, the two or more heteroatoms may all be the same as one another, or some or all of the two or more heteroatoms may each be different from the others.

The term "aromatic" refers to a group comprising a covalently closed ring having a delocalized π-electron system. Aromatic rings may be formed by five, six, seven, eight, nine, or more than nine atoms. Aromatics may be optionally substituted. Examples of aromatic groups include, but are not limited to phenyl, naphthalenyl, phenanthrenyl, anthracenyl, tetralinyl, fluorenyl, indenyl, and indanyl. The term aromatic includes, for example, benzenoid groups, connected via one of the ring-forming carbon atoms, and optionally carrying one or more substituents selected from an aryl, a heteroaryl, a cycloalkyl, a non-aromatic heterocycle, a halo, a hydroxy, an amino, a cyano, a nitro, an alkylamido, an acyl, a $C_{1-6}$ alkoxy, a $C_{1-6}$ alkyl, a $C_{1-6}$ hydroxyalkyl, a $C_{1-6}$ aminoalkyl, a $C_{1-6}$ alkylamino, an alkylsulfenyl, an alkylsulfinyl, an alkylsulfonyl, an sulfamoyl, or a trifluoromethyl. In certain embodiments, an aromatic group is substituted at one or more of the para, meta, and/or ortho positions. Examples of aromatic groups comprising substitutions include, but are not limited to, phenyl, 3-halophenyl, 4-halophenyl, 3-hydroxyphenyl, 4-hydroxyphenyl, 3-aminophenyl, 4-aminophenyl, 3-methylphenyl, 4-methylphenyl, 3-methoxyphenyl, 4-methoxyphenyl, 4-trifluoromethoxyphenyl, 3-cyanophenyl, 4-cyanophenyl, dimethylphenyl, naphthyl, hydroxynaphthyl, hydroxymethylphenyl, (trifluoromethyl)phenyl, alkoxyphenyl, 4-morpholin-4-ylphenyl, 4-pyrrolidin-1-ylphenyl, 4-pyrazolylphenyl, 4-triazolylphenyl, and 4-(2-oxopyrrolidin-1-yl)phenyl.

The term "aryl" refers to an aromatic group wherein each of the atoms forming the ring is a carbon atom. Aryl rings may be formed by five, six, seven, eight, nine, or more than nine carbon atoms. Aryl groups may be optionally substituted.

The term "heteroaryl" refers to an aromatic group wherein at least one atom forming the aromatic ring is a heteroatom. Heteroaryl rings may be formed by three, four, five, six, seven, eight, nine, or more than nine atoms. Heteroaryl groups may be optionally substituted. Examples of heteroaryl groups include, but are not limited to, aromatic $C_{3-8}$ heterocyclic groups comprising one oxygen or sulfur atom or up to four nitrogen atoms, or a combination of one oxygen or sulfur atom and up to two nitrogen atoms, and their substituted as well as benzo- and pyrido-fused derivatives, for example, connected via one of the ring-forming carbon atoms. In certain embodiments, heteroaryl groups are optionally substituted with one or more substituents, independently selected from halo, hydroxy, amino, cyano, nitro, alkylamido, acyl, $C_{1-6}$-alkoxy, $C_{1-6}$-alkyl, $C_{1-6}$-hydroxyalkyl, $C_{1-6}$-aminoalkyl, $C_{1-6}$-alkylamino, alkylsulfenyl, alkylsulfinyl, alkylsulfonyl, sulfamoyl, or trifluoromethyl. Examples of heteroaryl groups include, but are not limited to, unsubstituted and mono- or di-substituted derivatives of furan, benzofuran, thiophene, benzothiophene, pyrrole, pyridine, indole, oxazole, benzoxazole, isoxazole, benzisoxazole, thiazole, benzothiazole, isothiazole, imidazole, benzimidazole, pyrazole, indazole, tetrazole, quinoline, isoquinoline, pyridazine, pyrimidine, purine and pyrazine, furazan, 1,2,3-oxadiazole, 1,2,3-thiadiazole, 1,2,4-thiadiazole, triazole, benzotriazole, pteridine, phenoxazole, oxadiazole, benzopyrazole, quinolizine, cinnoline, phthalazine, quinazoline, and quinoxaline. In some embodiments, the substituents are halo, hydroxy, cyano, O—$C_{1-6}$-alkyl, $C_{1-6}$-alkyl, hydroxy-$C_{1-6}$-alkyl, and amino-$C_{1-6}$-alkyl.

The term "non-aromatic ring" refers to a group comprising a covalently closed ring that does not have a delocalized π-electron system.

The term "non-aromatic heterocycle" refers to a group comprising a non-aromatic ring wherein one or more atoms forming the ring is a heteroatom. Non-aromatic heterocyclic rings may be formed by three, four, five, six, seven, eight, nine, or more than nine atoms. Non-aromatic heterocycles may be optionally substituted. In certain embodiments, non-aromatic heterocycles comprise one or more carbonyl or thiocarbonyl groups such as, for example, oxo- and thio-containing groups. Examples of non-aromatic heterocycles include, but are not limited to, lactams, lactones, cyclic imides, cyclic thioimides, cyclic carbamates, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, pyrrolidone, pyrrolidione, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane.

The term "arylalkyl" refers to a group comprising an aryl group bound to an alkyl group.

The term "arylalkenyl" refers to a group comprising an aryl group bound to an alkenyl group.

The term "arylalkynyl" refers to a group comprising an aryl group bound to an alkynyl group.

The term "heteroarylalkyl" refers to a group comprising a heteroaryl group bound to an alkyl group.

The term "heteroarylalkenyl" refers to a group comprising a heteroaryl group bound to an alkenyl group.

The term "heteroarylalkynyl" refers to a group comprising a heteroaryl group bound to an alkynyl group.

The term "carbocycloalkyl" refers to a group comprising a carbocyclic cycloalkyl ring. Carbocycloalkyl rings may be formed by three, four, five, six, seven, eight, nine, or more than nine carbon atoms. Carbocycloalkyl groups may be optionally substituted.

The term "ring" refers to any covalently closed structure. Rings include, for example, carbocycles (e.g., aryls and cycloalkyls), heterocycles (e.g., heteroaryls and non-aromatic heterocycles), aromatics (e.g., aryls and heteroaryls), and non-aromatics (e.g., cycloalkyls and non-aromatic heterocycles). Rings may be optionally substituted. Rings may form part of a ring system.

The term "ring system" refers to a either a single ring or two or more rings, wherein, if two or more rings are present, the two or more of the rings are fused. The term "fused" refers to structures in which two or more rings share one or more bonds.

As used herein, the term "linked to form a ring" refers to instances where two atoms that are bound either to a single atom or to atoms that are themselves ultimately bound, are each bound to a linking group, such that the resulting structure forms a ring. That resulting ring comprises the two atoms that are linked to form a ring, the atom (or atoms) that previously linked those atoms, and the linker. For example, if A and E below are "linked to form a ring"

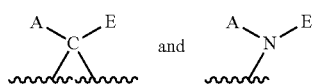 and the resulting ring includes A, E, the C (carbon) or N (nitrogen) to which they are attached, and a linking group. Unless otherwise indicated, that linking group may be of any length and may be optionally substituted. Referring to the above example, resulting structures include, but are not limited to:

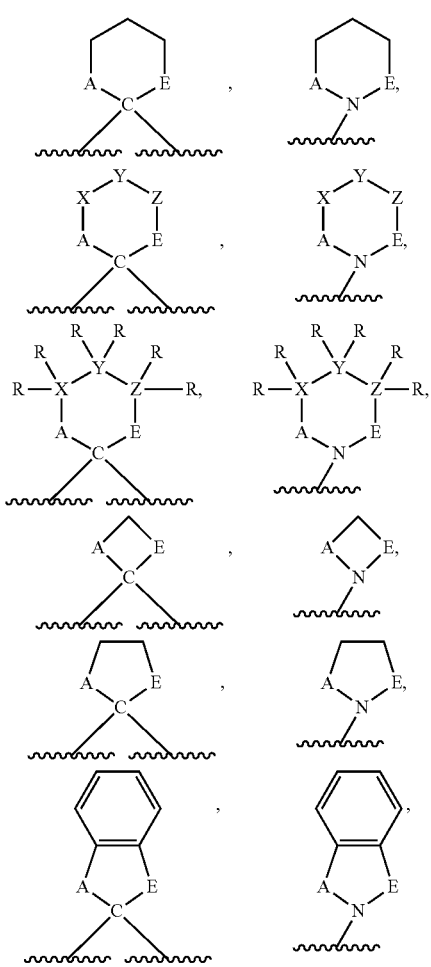

and the like.

In certain embodiments, the two substituents that together form a ring are not immediately bound to the same atom. For example, if A and E, below, are linked to form a ring:

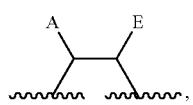

the resulting ring comprises A, E, the two atoms that already link A and E and a linking group. Examples of resulting structures include, but are not limited to:

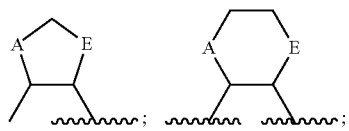

and the like.

In certain embodiments, the atoms that together form a ring are separated by three or more atoms. For example, if A and E, below, are linked to form a ring:

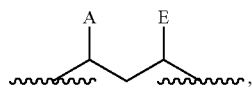

the resulting ring comprises A, E, the 3 atoms that already link A and E, and a linking group. Examples of resulting structures include, but are not limited to:

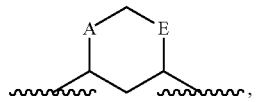

and the like.

As used herein, the term "together form a bond" refers to the instance in which two substituents to neighboring atoms are null the bond between the neighboring atoms becomes a double bond. For example, if A and E below "together form a bond"

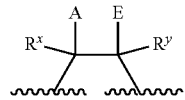

the resulting structure is:

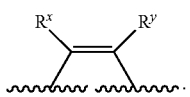

The term "null" refers to a group being absent from a structure. For example, in the structure

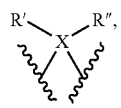

where in certain instances X is N (nitrogen), if X is N (nitrogen), one of R' or R" is null, meaning that only three groups are bound to the N (nitrogen).

The substituent "R" appearing by itself and without a number designation refers to a substituent selected from alkyl, cycloalkyl, aryl, heteroaryl (bonded through a ring carbon) and non-aromatic heterocycle (bonded through a ring carbon).

The term "O-carboxy" refers to the group consisting of formula RC(=O)O—.

The term "C-carboxy" refers to the group consisting of formula —C(=O)OR.

The term "acetyl" refers to the group consisting of formula —C(=O)CH$_3$.

The term "trihalomethanesulfonyl" refers to the group consisting of formula X$_3$CS(=O)$_2$— where X is a halogen.

The term "cyano" refers to the group consisting of formula —CN.

The term "isocyanato" refers to the group consisting of formula —NCO.

The term "thiocyanato" refers to the group consisting of formula —CNS.

The term "isothiocyanato" refers to the group consisting of formula —NCS.

The term "sulfonyl" refers to the group consisting of formula —S(=O)—R.

The term "S-sulfonamido" refers to the group consisting of formula —S(=O)$_2$NR.

The term "N-sulfonamido" refers to the group consisting of formula RS(=O)$_2$NH—.

The term "trihalomethanesulfonamido" refers to the group consisting of formula X$_3$CS(=O)$_2$NR—.

The term "O-carbamyl" refers to the group consisting of formula —OC(=O)—NR.

The term "N-carbamyl" refers to the group consisting of formula ROC(=O)NH—.

The term "O-thiocarbamyl" refers to the group consisting of formula —OC(=S)—NR.

The term "N-thiocarbamyl" refers to the group consisting of formula ROC(=S)NH—.

The term "C-amido" refers to the group consisting of formula —C(=O)—NR$_2$.

The term "N-amido" refers to the group consisting of formula RC(=O)NH—.

The term "oxo" refers to the group consisting of formula =O.

The term "keto" and "carbonyl" used herein refers to C=O.

The term "thiocarbonyl" used herein refers to C=S.

The term "ester" refers to a chemical moiety with formula —(R)$_n$—C(=O)OR', where R and R' are independently selected from alkyl, cycloalkyl, aryl, heteroaryl (bonded through a ring carbon) and non-aromatic heterocycle (bonded through a ring carbon), where n is 0 or 1.

The term "amide" refers to a chemical moiety with formula —(R)$_n$—C(=O)NHR' or —(R)$_n$—NHC(=O)R', where R is selected from alkyl, cycloalkyl, aryl, heteroaryl (bonded through a ring carbon) and heteroalicyclic (bonded through a ring carbon), where n is 0 or 1 and R' is selected from hydrogen, alkyl, cycloalkyl, aryl, heteroaryl (bonded through a ring carbon) and heteroalicyclic (bonded through a ring carbon), where n is 0 or 1. In certain embodiments, an amide may be an amino acid or a peptide.

The term "amino" refers to a chemical moiety with formula —NHR'R", where R' and R" are each independently selected from hydrogen, alkyl, cycloalkyl, aryl, heteroaryl (bonded through a ring carbon) and heteroalicyclic (bonded through a ring carbon).

The terms "amine," "hydroxy," and "carboxyl" include such groups that have been esterified or amidified. Procedures and specific groups used to achieve esterification and amidification are known to those of skill in the art and can readily be found in reference sources such as Greene and Wuts, Protective Groups in Organic Synthesis, 3$^{rd}$ Ed., John Wiley & Sons, New York, N.Y., 1999, which is incorporated herein in its entirety.

Unless otherwise indicated, the term "optionally substituted," refers to a group in which none, one, or more than one of the hydrogen atoms has been replaced with one or more group(s) individually and independently selected from: alkyl, alkenyl, cycloalkenyl, alkynyl, heteroalkyl, haloalkyl, cycloalkyl, aryl, arylalkyl, alkenylO—, arylalkylO—, arylalkylNH—, alkenylO—, cycloalkylC(=O)—, arylC(=O)—, arylC(=O)NH—, arylNHC(=O)—, aryl(CH$_2$)$_{0-3}$O(CH$_2$)$_{0-3}$—, —COOH, HO(CH$_2$)$_{1-3}$NH—, HO(CH$_2$)$_{1-3}$O—, HO(CH$_2$)$_{1-3}$—, HO(CH$_2$)$_{1-3}$O(CH$_2$)$_{1-3}$—, —C(=O)NHNH$_2$, heteroaryl, non-aromatic heterocycle, hydroxy, alkoxy, aryloxy, mercapto, alkylthio, arylthio, cyano, halo, carbonyl, oxo, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and amino, including mono- and di-substituted amino groups, and the protected derivatives of amino groups. Such protective derivatives (and protecting groups that may form such protective derivatives) are known to those of skill in the art and may be found in references such as Greene and Wuts, above. When the group contains a nitrogen, or a sulfur, an oxo as a substituent also includes oxides, for example pyridine-N-oxide, thiopyran sulfoxide and thiopyran-S,S-dioxide. In embodiments in which two or more hydrogen atoms have been substituted, the substituent groups may together form a ring.

The term "isomer" includes but not limited to stereoic isomers, geometric isomers, enantiomeric isomers, tautomeric isomers, and atromeric isomers.

Throughout the specification, groups and substituents thereof can be chosen by one skilled in the field to provide stable moieties and compounds.

The term "carrier" refers to a compound that facilitates the incorporation of another compound into cells or tissues. For example, dimethyl sulfoxide (DMSO) is a commonly used carrier for improving incorporation of certain organic compounds into cells or tissues.

The term "pharmaceutical agent" refers to a chemical compound or composition capable of inducing a desired therapeutic effect in a patient. In certain embodiments, a pharmaceutical agent comprises an active agent, which is the agent that induces the desired therapeutic effect. In certain embodiments, a pharmaceutical agent comprises a prodrug. In certain embodiments, a pharmaceutical agent comprises inactive ingredients such as carriers, excipients, and the like.

The term "therapeutically effective amount" refers to an amount of a pharmaceutical agent sufficient to achieve a desired therapeutic effect.

The term "prodrug" refers to a pharmaceutical agent that is converted from a less active form into a corresponding more active form in vivo.

The term "pharmaceutically acceptable" refers to a formulation of a compound that does not significantly abrogate the biological activity, a pharmacological activity and/or other properties of the compound when the formulated compound is administered to a patient. In certain embodiments, a pharmaceutically acceptable formulation does not cause significant irritation to a patient.

The term "co-administer" refers to administering more than one pharmaceutical agent to a patient. In certain embodiments, co-administered pharmaceutical agents are administered together in a single dosage unit. In certain embodiments, co-administered pharmaceutical agents are administered separately. In certain embodiments, co-administered pharmaceutical agents are administered at the same time. In certain embodiments, co-administered pharmaceutical agents are administered at different times.

The term "patient" includes human and animal subjects.

The term "substantially pure" means an object species (e.g., compound) is the predominant species present (i.e., on a molar basis it is more abundant than any other individual species in the composition). In certain embodiments, a substantially purified fraction is a composition wherein the object species comprises at least about 50 percent (on a molar basis) of all species present. In certain embodiments, a substantially pure composition will comprise more than about 80%, 85%, 90%, 95%, or 99% of all species present in the composition. In certain embodiments, the object species is purified to essential homogeneity (contaminant species cannot be detected in the composition by conventional detection methods) wherein the composition consists essentially of a single species.

The term "tissue-selective" refers to the ability of a compound to modulate a biological activity in one tissue to a greater or lesser degree than it modulates a biological activity in another tissue. The biological activities in the different tissues may be the same or they may be different. The biological activities in the different tissues may be mediated by the same type of target receptor. For example, in certain embodiments, a tissue-selective compound may modulate receptor mediated biological activity in one tissue and fail to modulate, or modulate to a lesser degree, receptor mediated biological activity in another tissue type.

The term "monitoring" refers to observing an effect or absence of any effect. In certain embodiments, one monitors cells after contacting those cells with a compound of the present embodiments. Examples of effects that may be monitored include, but are not limited to, changes in cell phenotype, cell proliferation, receptor activity, or the interaction between a receptor and a compound known to bind to the receptor.

The term "cell phenotype" refers to physical or biological characteristics. Examples of characteristics that constitute phenotype included, but are not limited to, cell size, cell proliferation, cell differentiation, cell survival, apoptosis (cell death), or the utilization of a metabolic nutrient (e.g., glucose uptake). Certain changes or the absence of changes in cell phenotype are readily monitored using techniques known in the art.

The term "cell proliferation" refers to the rate at which cells divide. In certain embodiments, cells are in situ in an organism. In certain embodiments, cell are grown in vitro in a vessel. The number of cells growing in a vessel can be quantified by a person skilled in the art (e.g., by counting cells in a defined area using a microscope or by using laboratory apparatus that measure the density of cells in an appropriate medium). One skilled in that art can calculate cell proliferation by determining the number of cells at two or more times.

The term "contacting" refers to bringing two or more materials into close enough proximity that they may interact. In certain embodiments, contacting can be accomplished in a vessel such as a test tube, a petri dish, or the like. In certain embodiments, contacting may be performed in the presence of additional materials. In certain embodiments, contacting may be performed in the presence of cells. In certain of such embodiments, one or more of the materials that are being contacted may be inside a cell. Cells may be alive or may dead. Cells may or may not be intact.

In certain embodiments, a salt corresponding to any of the compounds provided herein is provided. In certain embodiments, a salt corresponding to a selective GCSFR modulator is provided. In certain embodiments, a salt corresponding to a selective GCSF receptor binding agent is provided. In certain embodiments, a salt is obtained by reacting a compound with an acid, such as hydrochloric acid, hydrobromic acid, sulfuric acid, nitric acid, phosphoric acid, methanesulfonic acid, ethanesulfonic acid, p-toluenesulfonic acid, salicylic acid, and the like. In certain embodiments, a salt is obtained by reacting a compound with a base to form a salt such as an ammonium salt, an alkali metal salt, such as a sodium or a potassium salt, an alkaline earth metal salt, such as a calcium or a magnesium salt, a salt of organic bases such as choline, dicyclohexylamine, N-methyl-D-glucamine, tris(hydroxymethyl)methylamine, 4-(2-hydroxyethyl)-morpholine, 1-(2-hydroxyethyl)-pyrrolidine, ethanolamine and salts with amino acids such as arginine, lysine, and the like. In certain embodiments, a salt is obtained by reacting a free acid form of a selective HGF modulator or selective GCSFR binding agent with multiple molar equivalents of a base, such as bis-sodium, bis-ethanolamine, and the like.

In certain embodiments, a salt corresponding to a compound of the present embodiments is selected from acetate, ammonium, benzenesulfonate, benzoate, bicarbonate, bisulfate, bitartrate, borate, bromide, calcium edetate, camsylate, carbonate, chloride, cholinate, clavulanate, citrate, dihydrochloride, diphosphate, edetate, edisylate, estolate, esylate, fumarate, gluceptate, gluconate, glutamate, glycollylarsanilate, hexylresorcinate, hydrabanine, hydrobromide, hydrochloride, hydroxynaphthoate, iodide, isethionate, lactate, lactobionate, laurate, magnesium, malate, maleate, mandelate, mucate, napsylate, nitrate, N-methylglucamine, oxalate, pamoate (embonate), palmitate, pantothenate, phosphate, polygalacturonate, potassium, salicylate, sodium, stearate, subaceatate, succinate, sulfate, tannate, tartrate, teoclate, tosylate, triethiodide, tromethamine, trimethylammonium, and valerate salts.

In certain embodiments, one or more carbon atoms of a compound of the present embodiments are replaced with silicon. See e.g., WO 03/037905A1; Tacke and Zilch, Endeavour, New Series, 10, 191-197 (1986); Bains and Tacke, Curr. Opin. Drug Discov Devel. July: 6(4):526-43 (2003), all of which are incorporated herein by reference in their entirety. In certain embodiments, compounds comprising one or more silicon atoms possess certain desired properties, including, but not limited to, greater stability and/or longer half-life in a patient, when compared to the same compound in which none of the carbon atoms have been replaced with a silicon atom.

Certain Compounds

Certain embodiments include a compound of Formula (I), (II), (III), or (IV):

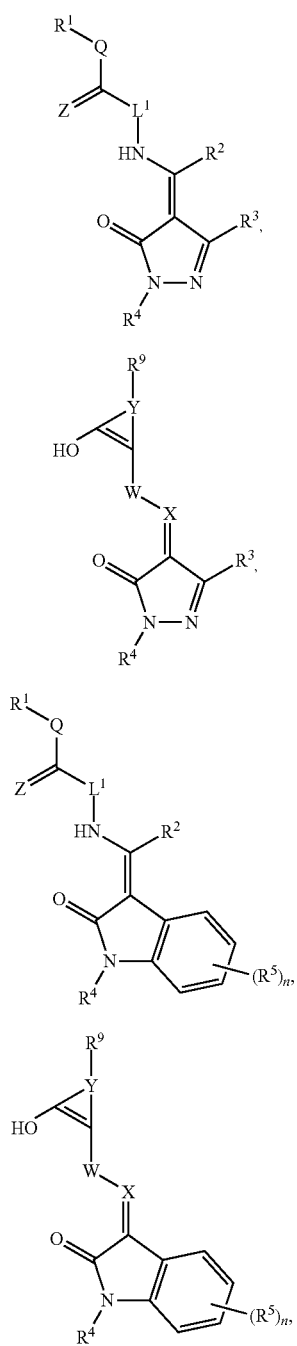

a tautomer thereof, or a pharmaceutically acceptable salt thereof, wherein:

$R^1$ is selected from hydrogen, $OR^6$, $NO_2$, CN, $NR^6R^7$, $CO_2R^6$, $C(=O)NR^6R^7$, $SO_3R^6$, $SO_2NR^6R^8$, an optionally substituted $C_1$-$C_6$ alkyl, an optionally substituted $C_2$-$C_6$ alkenyl, an optionally substituted $C_2$-$C_6$ alkynyl, an optionally substituted $C_1$-$C_6$ heteroalkyl, an optionally substituted $C_3$-$C_6$ cycloalkyl, an optionally substituted $C_3$-$C_6$ cycloalkenyl, an optionally substituted $C_2$-$C_6$ heterocyclyl, an optionally substituted arylalkyl, an optionally substituted aryl, and an optionally substituted heteroaryl;

$R^2$ and $R^3$ are independently selected from hydrogen, an optionally substituted $C_1$-$C_6$ alkyl, an optionally substituted $C_2$-$C_6$ alkenyl, an optionally substituted $C_2$-$C_6$ alkynyl, an optionally substituted $C_1$-$C_6$ heteroalkyl, an optionally substituted $C_3$-$C_8$ cycloalkyl, an optionally substituted $C_3$-$C_8$ cycloalkenyl, an optionally substituted $C_1$-$C_6$ heterocycle, an optionally substituted aryl, and an optionally substituted heteroaryl;

$R^4$ is selected from hydrogen, an optionally substituted $C_1$-$C_6$ alkyl, an optionally substituted $C_2$-$C_6$ alkenyl, an optionally substituted $C_2$-$C_6$ alkynyl, an optionally substituted $C_1$-$C_6$ heteroalkyl, an optionally substituted $C_3$-$C_8$ cycloalkyl, an optionally substituted $C_3$-$C_8$ cycloalkenyl, an optionally substituted $C_1$-$C_6$ heterocycle, an optionally substituted aryl, an optionally substituted heteroaryl, an optionally substituted arylalkyl, an optionally substituted arylalkenyl, an optionally substituted arylalkynyl, and an optionally substituted heteroarylalkyl;

$R^5$ is selected from hydrogen, halogen, $NO_2$, CN, $CF_3$, $OR^6$, $CO_2R^6$, $C(=O)NR^6R^7$, $SO_3R^6$, and $SO_2NR^6R^8$, an optionally substituted aryl, an optionally substituted $C_1$-$C_6$ alkyl, and an optionally substituted $C_1$-$C_6$ heteroalkyl;

$R^6$ is selected from hydrogen, an optionally substituted $C_1$-$C_6$ alkyl, a $C_1$-$C_6$ heteroalkyl, an optionally substituted aryl, and an optionally substituted heteroaryl;

$R^7$ is selected from hydrogen, $C(=O)R^8$, $C(=O)NHR^8$, an optionally substituted $C_1$-$C_6$ alkyl, and an optionally substituted $C_1$-$C_6$ heteroalkyl; or —$NR^6R^7$ is an optionally substituted non-aromatic heterocycle linked through a ring nitrogen;

$R^8$ is selected from hydrogen, an optionally substituted $C_1$-$C_6$ alkyl, and an optionally substituted $C_1$-$C_6$ heteroalkyl;

$R^9$ is selected from hydrogen, an optionally substituted $C_1$-$C_6$ alkyl, an optionally substituted $C_2$-$C_6$ alkenyl, an optionally substituted $C_2$-$C_6$ alkynyl, an optionally substituted $C_1$-$C_6$ heteroalkyl, an optionally substituted $C_3$-$C_8$ cycloalkyl, an optionally substituted $C_3$-$C_8$ cycloalkenyl, an optionally substituted $C_1$-$C_6$ heterocycle, an optionally substituted heteroaryl, an optionally substituted arylalkyl, an optionally substituted arylalkenyl, an optionally substituted arylalkynyl, an optionally substituted heteroarylalkyl, an optionally substituted heteroarylalkenyl, and an optionally substituted heteroarylalkynyl;

Q is selected from the group consisting of $NR^6$, an optionally substituted $C_1$-$C_6$ alkyl, an optionally substituted $C_3$-$C_8$ cycloalkyl, an optionally substituted $C_1$-$C_6$ heteroalkyl, and an optionally substituted non-aromatic heterocycle;

$L^1$ is selected from NH and $CHR^2$;

W is selected from O (oxygen) and NH;

X is N (nitrogen) or $CR^2$;

Y is selected from an optionally substituted $C_1$-$C_6$ alkyl, $C_2$-$C_6$ alkenyl, an optionally substituted $C_1$-$C_6$ heteroalkyl, an optionally substituted $C_1$-$C_6$ heteroalkenyl, an optionally substituted phenylalkenyl, and an optionally substituted heterocyclealkenyl;

Z is O (oxygen) or S (sulfur);

n is 1, 2 or 3; and provided that if $R^2$ is methyl, $R^4$ is phenyl, $L^1$ is NH, and Q is N-Ph-$R^1$ in Formula I and III, $R^1$ of Formula I and III is not selected from the group of halogen, alkyl, substituted alkyl, carboxylic acid, and carboxylic esters.

Certain embodiments include a compound having the structure of Formula (Ia):

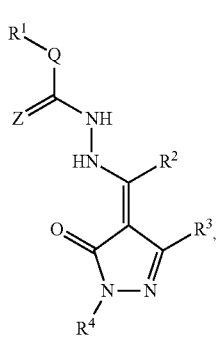

(Ia)

a tautomer thereof, or a pharmaceutically acceptable salt thereof, wherein:

$R^1$ is selected from hydrogen, an optionally substituted $C_1$-$C_6$ alkyl, an optionally substituted $C_3$-$C_6$ cycloalkyl, an optionally substituted $C_3$-$C_6$ cycloalkenyl, an optionally substituted $C_2$-$C_6$ heterocyclyl, an optionally substituted aryl, and an optionally substituted heteroaryl;

$R^2$ and $R^3$ are independently selected from hydrogen, an optionally substituted $C_1$-$C_6$ alkyl, an optionally substituted $C_3$-$C_8$ cycloalkyl, an optionally substituted $C_1$-$C_6$ heterocycle, an optionally substituted aryl, and an optionally substituted heteroaryl;

$R^4$ is selected from hydrogen, an optionally substituted $C_1$-$C_6$ alkyl, an optionally substituted $C_3$-$C_8$ cycloalkyl, an optionally substituted $C_3$-$C_8$ cycloalkenyl, an optionally substituted $C_1$-$C_6$ heterocycle, an optionally substituted aryl, and an optionally substituted heteroaryl;

Q is selected from an optionally substituted $C_1$-$C_6$ alkyl, an optionally substituted $C_3$-$C_8$ cycloalkyl, and an optionally substituted non-aromatic heterocycle; and Z is O (oxygen) or S (sulfur).

The compound of Claim 2, wherein:

$R^1$ is selected from hydrogen, and an optionally substituted $C_1$-$C_6$ alkyl;

$R^2$ and $R^3$ are independently selected from hydrogen, and an optionally substituted $C_1$-$C_6$ alkyl;

$R^4$ is selected from hydrogen, an optionally substituted $C_1$-$C_6$ alkyl, an optionally substituted aryl, and an optionally substituted heteroaryl;

Q is selected from an optionally substituted $C_1$-$C_6$ alkyl, and an optionally substituted $C_3$-$C_8$ cycloalkyl; and Z is O (oxygen).

The compound of Claim 3, wherein:

$R^1$ is selected from hydrogen, and an optionally substituted $C_1$-$C_3$ alkyl;

$R^2$ and $R^3$ are independently selected from hydrogen, and an optionally substituted $C_1$-$C_3$ alkyl;

$R^4$ is selected from optionally substituted $C_1$-$C_6$ alkyl, and an optionally substituted aryl; and Q is selected from an optionally substituted $C_1$-$C_3$ alkyl, and an optionally substituted $C_3$-$C_3$ cycloalkyl.

The compound of Claim 4, wherein:

$R^1$ is hydrogen;

$R^2$ and $R^3$ are independently an optionally substituted $C_1$-$C_3$ alkyl;

$R^4$ is an optionally substituted phenyl; and

Q is an optionally substituted $C_1$-$C_3$ alkyl.

Certain embodiments include a compound having the structure of Formula (IIa) or (IIb):

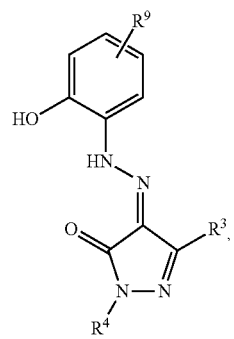

(IIa)

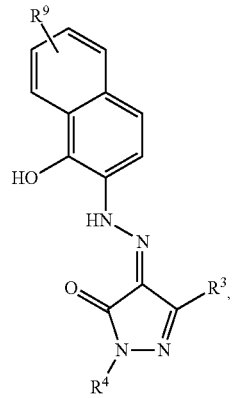

(IIb)

a tautomer thereof, or a pharmaceutically acceptable salt thereof, wherein:

$R^3$ is selected from hydrogen, an optionally substituted $C_1$-$C_6$ alkyl, an optionally substituted $C_3$-$C_8$ cycloalkyl, an optionally substituted $C_1$-$C_6$ heterocycle, an optionally substituted aryl, and an optionally substituted heteroaryl;

$R^4$ is selected from an optionally substituted $C_1$-$C_6$ alkyl, an optionally substituted $C_3$-$C_8$ cycloalkyl, an optionally substituted $C_1$-$C_6$ heterocyclyl, an optionally substituted aryl, an optionally substituted heteroaryl, an optionally substituted arylalkyl, and an optionally substituted heteroarylalkyl; and $R^9$ is selected from hydrogen, an optionally substituted $C_1$-$C_6$ alkyl, an optionally substituted $C_3$-$C_8$ cycloalkyl, an optionally substituted $C_1$-$C_6$ heterocyclyl, an optionally substituted heteroaryl, an optionally substituted arylalkyl, and an optionally substituted heteroarylalkyl.

The compound of Claim 6, wherein:

$R^3$ is selected from hydrogen, and an optionally substituted $C_1$-$C_3$ alkyl;

$R^4$ is selected from an optionally substituted $C_1$-$C_6$ alkyl, an optionally substituted $C_3$-$C_8$ cycloalkyl, and an optionally substituted aryl; and $R^9$ is selected from an optionally substituted $C_1$-$C_6$ alkyl, an optionally substituted arylalkyl, an optionally substituted arylalkenyl, an optionally substituted arylalkynyl, and an optionally substituted heteroarylalkyl.

In certain embodiments, $R^3$ is an optionally substituted $C_1$-$C_3$ alkyl;

$R^4$ is selected from an optionally substituted $C_1$-$C_4$ alkyl, and an optionally substituted aryl; and $R^9$ is selected from an optionally substituted $C_1$-$C_3$ alkyl, an optionally substituted arylalkyl, an optionally substituted arylalkenyl, and an optionally substituted arylalkynyl.

Certain embodiments include a compound having the structure of Formula (IIIa):

(IIIa)

a tautomer thereof, or a pharmaceutically acceptable salt thereof, wherein:

$R^1$ is selected from hydrogen, $OR^6$, $NR^6R^7$, $CO_2R^6$, $C(=O)NR^6R^7$, an optionally substituted $C_2$-$C_6$ heterocyclyl, an optionally substituted arylalkyl, an optionally substituted aryl, and an optionally substituted heteroaryl;

$R^2$ is selected from hydrogen, an optionally substituted $C_1$-$C_6$ alkyl, an optionally substituted $C_3$-$C_8$ cycloalkyl, an optionally substituted aryl, and an optionally substituted heteroaryl;

$R^4$ is selected from hydrogen, an optionally substituted $C_1$-$C_6$ alkyl, an optionally substituted aryl, an optionally substituted heteroaryl, an optionally substituted arylalkyl, and an optionally substituted heteroarylalkyl;

$R^5$ is selected from hydrogen, halogen, CN, $CF_3$, $OR^6$, an optionally substituted aryl, and an optionally substituted $C_1$-$C_6$ alkyl;

$R^6$ is selected from hydrogen, an optionally substituted $C_1$-$C_6$ alkyl, an optionally substituted aryl, and an optionally substituted heteroaryl;

$R^7$ is selected from hydrogen, $C(=O)R^8$, $C(=O)NHR^8$, and an optionally substituted $C_1$-$C_6$ alkyl; or —$NR^6R^7$ is an optionally substituted non-aromatic heterocycle linked through a ring nitrogen;

$R^8$ is selected from hydrogen, and an optionally substituted $C_1$-$C_6$ alkyl;

Q is selected from $NR^6$, an optionally substituted $C_1$-$C_6$ alkyl, an optionally substituted $C_3$-$C_8$ cycloalkyl, and an optionally substituted non-aromatic heterocyclyl;

Z is O (oxygen) or S (sulfur); and n is 1, or 2.

In certain embodiments, wherein $R^1$ is selected from hydrogen, $OR^6$, $NR^6R^7$, $CO_2R^6$, $C(=O)NR^6R^7$, an optionally substituted $C_2$-$C_6$ heterocyclyl, an optionally substituted arylalkyl, an optionally substituted aryl, and an optionally substituted heteroaryl;

$R^2$ is selected from hydrogen, an optionally substituted $C_1$-$C_6$ alkyl, an optionally substituted $C_3$-$C_8$ cycloalkyl, an optionally substituted aryl, and an optionally substituted heteroaryl;

$R^4$ is selected from hydrogen, an optionally substituted $C_1$-$C_6$ alkyl, an optionally substituted aryl, an optionally substituted heteroaryl, an optionally substituted arylalkyl, and an optionally substituted heteroarylalkyl;

$R^5$ is selected from hydrogen, halogen, CN, $CF_3$, $OR^6$, an optionally substituted aryl, and an optionally substituted $C_1$-$C_6$ alkyl;

$R^6$ is selected from hydrogen, and an optionally substituted $C_1$-$C_6$ alkyl;

$R^7$ is selected from hydrogen, $C(=O)R^8$, $C(=O)NHR^8$, and an optionally substituted $C_1$-$C_6$ alkyl;

$R^8$ is selected from hydrogen, and an optionally substituted $C_1$-$C_6$ alkyl;

Q is selected from $NR^6$, an optionally substituted $C_1$-$C_4$ alkyl, an optionally substituted $C_3$-$C_6$ cycloalkyl, and an optionally substituted non-aromatic heterocyclyl;

Z is O (oxygen); and n is 1.

In certain embodiments, $R^1$ is selected from hydrogen, $OR^6$, $NR^6R^7$, $C(=O)NR^6R^7$, an optionally substituted arylalkyl, and an optionally substituted heteroaryl;

$R^2$ is selected from hydrogen, an optionally substituted $C_1$-$C_6$ alkyl, an optionally substituted aryl, and an optionally substituted heteroaryl;

$R^4$ is an optionally substituted aryl;

$R^5$ is selected from hydrogen, chloro, CN, $CF_3$, $OR^6$, an optionally substituted aryl, and an optionally substituted $C_1$-$C_6$ alkyl;

$R^6$ is selected from hydrogen, and an optionally substituted $C_1$-$C_3$ alkyl;

$R^7$ is selected from hydrogen, $C(=O)R^8$, $C(=O)NHR^8$, and an optionally substituted $C_1$-$C_3$ alkyl;

$R^8$ is selected from hydrogen, and an optionally substituted $C_1$-$C_3$ alkyl; and Q is selected from optionally substituted $C_1$-$C_3$ alkyl, an optionally substituted $C_3$-$C_6$ cycloalkyl, and an optionally substituted non-aromatic heterocyclyl.

Certain embodiments include a compound having the structure of Formula (IVa) or (IVb):

(IVa)

(IVb)

a tautomer thereof, or a pharmaceutically acceptable salt thereof, wherein:

$R^4$ is selected from an optionally substituted $C_1$-$C_6$ alkyl, an optionally substituted $C_3$-$C_8$ cycloalkyl, an optionally substituted $C_1$-$C_6$ heterocyclyl, an optionally substituted aryl, an optionally substituted heteroaryl, an optionally substituted arylalkyl, and an optionally substituted heteroarylalkyl;

$R^5$ is selected from halogen, CN, $CF_3$, $OR^6$, an optionally substituted aryl, and an optionally substituted $C_1$-$C_6$ alkyl;

$R^6$ is selected from hydrogen, an optionally substituted $C_1$-$C_6$ alkyl, an optionally substituted aryl, and an optionally substituted heteroaryl; and $R^9$ is selected from hydrogen, an optionally substituted $C_1$-$C_6$ alkyl, an optionally substituted $C_3$-$C_8$ cycloalkyl, an optionally substituted $C_1$-$C_6$ heterocyclyl, an optionally substituted heteroaryl, an optionally substituted arylalkyl, and an optionally substituted heteroarylalkyl.

In certain embodiments, $R^4$ is selected from an optionally substituted $C_1$-$C_6$ alkyl, an optionally substituted $C_3$-$C_8$ cycloalkyl, and an optionally substituted aryl;

$R^5$ is selected from chloro, CN, $CF_3$, $OR^6$, an optionally substituted aryl, and an optionally substituted $C_1$-$C_6$ alkyl;

$R^6$ is selected from hydrogen, and an optionally substituted $C_1$-$C_3$ alkyl;

$R^9$ is selected from an optionally substituted $C_1$-$C_6$ alkyl, an optionally substituted arylalkyl, an optionally substituted arylalkenyl, an optionally substituted arylalkynyl, and an optionally substituted heteroarylalkyl, and n is 1, or 2.

In certain embodiments, $R^4$ is selected from an optionally substituted $C_1$-$C_4$ alkyl, and an optionally substituted aryl;

$R^5$ is selected from chloro, CN, $CF_3$, and an optionally substituted $C_1$-$C_3$ alkyl;

$R^9$ is selected from an optionally substituted $C_1$-$C_3$ alkyl, an optionally substituted arylalkyl, an optionally substituted arylalkenyl, and an optionally substituted arylalkynyl; and n is 1.

In certain embodiments, unless otherwise specified, groups indicated as "optionally substituted" are optionally substituted with one or more group(s) individually and independently selected from the group consisting of $C_1$-$C_6$ alkyl, $C_2$-$C_6$ alkenyl, $C_2$-$C_6$ alkynyl, $C_1$-$C_6$ heteroalkyl, $C_1$-$C_6$ haloalkyl, $C_3$-$C_6$ cycloalkyl, aryl, arylalkyl, alkenylO—, arylalkylO—, arylalkylNH—, alkenylO—, cycloalkylC(=O)—, arylC(=O)—, arylC(=O)NH—, arylNHC(=O)—, aryl$(CH_2)_{0-3}$O$(CH_2)_{0-3}$—, HO$(CH_2)_{1-3}$NH—, HO$(CH_2)_{1-3}$O—, HO$(CH_2)_{1-3}$—, HO$(CH_2)_{1-3}$O$(CH_2)_{1-3}$—, —C(=O)NHNH$_2$, heteroaryl, non-aromatic heterocycle, hydroxy, alkoxy, aryloxy, mercapto, alkylthio, arylthio, cyano, halo, oxo, O-carbamyl, N-carbamyl, O-thiocarbamyl, N-thiocarbamyl, C-amido, N-amido, S-sulfonamido, N-sulfonamido, C-carboxy, O-carboxy, nitro, and amino.

Certain embodiments include use of a compound for treating a hematopoietic or neurological disorder comprising administering an effective amount of a compound of Formula (V) or (VI) to a subject in need thereof, wherein Formula (V) or (VI): having the structure:

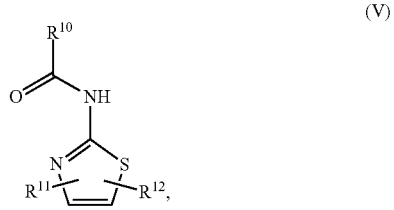

(V)

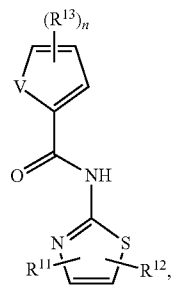

(VI)

or pharmaceutically acceptable salt thereof, wherein:

$R^{10}$ is selected from an optionally substituted $C_1$-$C_{12}$ alkyl, an optionally substituted $C_1$-$C_{12}$ heteroalkyl, an optionally substituted $C_2$-$C_{12}$ heteroalkenyl, an optionally substituted $C_2$-$C_{12}$ heteroalkynyl, an optionally substituted $C_1$-$C_{12}$ cycloalkyl; an optionally substituted $C_1$-$C_6$ heterocycloalkyl, an optionally substituted heteroarylalkyl, an optionally substituted arylheteroalkyl, an optionally substituted heteroarylheteroalkyl, $OR^{14}$, $SR^{14}$, and $NR^8R^{14}$;

$R^{11}$ is selected from hydrogen, halogen, an optionally substituted $C_1$-$C_6$ alkyl, an optionally substituted $C_1$-$C_6$ heteroalkyl, an optionally substituted $C_3$-$C_8$ cycloalkyl, and an optionally substituted $C_1$-$C_6$ heterocycle;

$R^{12}$ is selected from an optionally substituted $C_1$-$C_6$ heteroalkyl, an optionally substituted $C_3$-$C_8$ cycloalkyl, an optionally substituted $C_1$-$C_6$ heterocycle, an optionally substituted aryl, and an optionally substituted heteroaryl;

$R^{13}$ is selected from hydrogen, halogen, an optionally substituted $C_1$-$C_8$ alkyl, an optionally substituted $C_1$-$C_8$ heteroalkyl, an optionally substituted $C_2$-$C_8$ heteroalkenyl, an optionally substituted $C_3$-$C_8$ cycloalkyl, an optionally substituted $C_1$-$C_6$ heterocycloalkyl, $OR^{14}$, $SR^{14}$, and $NR^8R^{14}$;

$R^{14}$ is selected from an optionally substituted aryl and an optionally substituted heteroaryl;

V is selected from CH=CH, N=CH, CH=N, NH, O (oxygen), and S (sulfur); and n is 1, 2 or 3.

In certain embodiments, compounds as disclosed herein can exist in tautomeric forms. All tautomeric forms are intended to be included in the scope of the compounds as disclosed herein. Likewise, when compounds contain a double bond, there exists the possibility of cis- and trans-type isomeric forms of the compounds. Both cis- and trans-isomers, both in pure form as well as mixtures of cis- and trans-isomers, are contemplated. Thus, reference herein to a compound includes all of the aforementioned isomeric forms unless the context clearly dictates otherwise.

In certain embodiments, a compound of Formula (I) can reside in one or more of the tautomeric forms. For example, the compound of Formula (I) can reside in the tautomeric forms shown below:

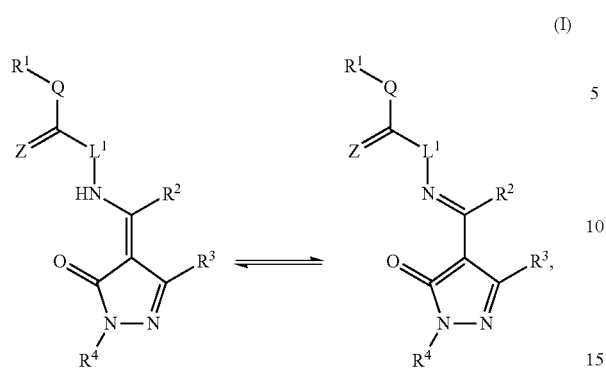

(I)

or their pharmaceutically acceptable salts.

In certain embodiments, a compound of Formula (II) can reside in one or more of the tautomeric forms. For example, the compound of Formula (II) can reside in the tautomeric forms shown below:

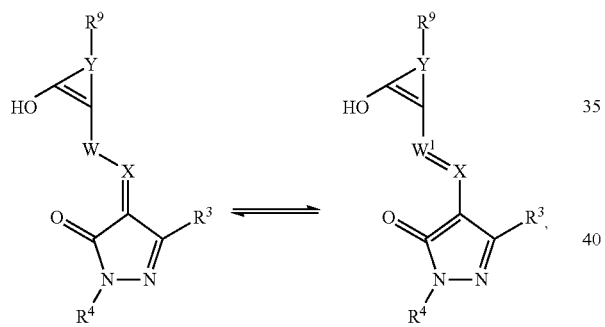

(II)

or their pharmaceutically acceptable salts, wherein W can be NH; and $W^1$ can be N (nitrogen).

In certain embodiments, a compound of Formula (III) can reside in one or more of the tautomeric forms. For example, the compound of Formula (III) can reside in the tautomeric forms shown below:

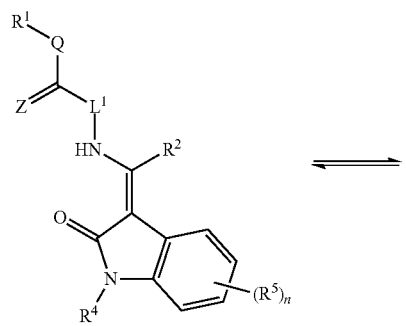

(III)

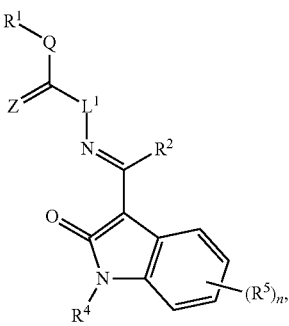

or their pharmaceutically acceptable salts.

In certain embodiments, a compound of Formula (IV) can reside in one or more of the tautomeric forms. For example, the compound of Formula (IV) can reside in the tautomeric forms shown below:

(IV)

or their pharmaceutically acceptable salts, wherein W can be NH; and $W^1$ can be N (nitrogen).

Certain Synthesis Methods

Scheme I

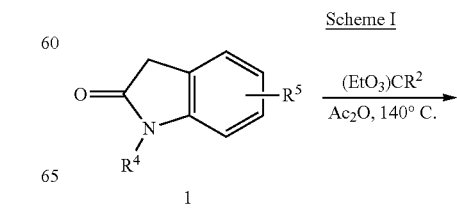

1

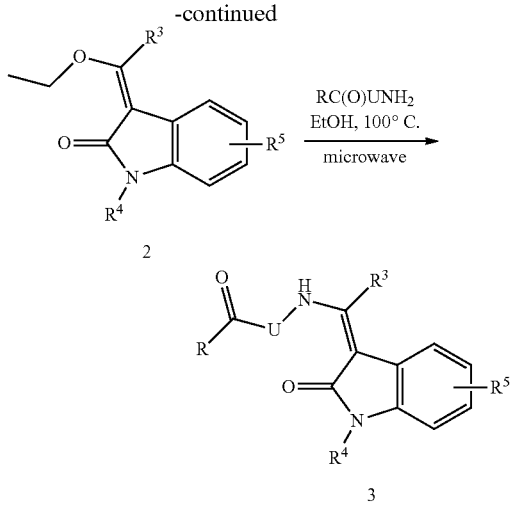

Scheme III

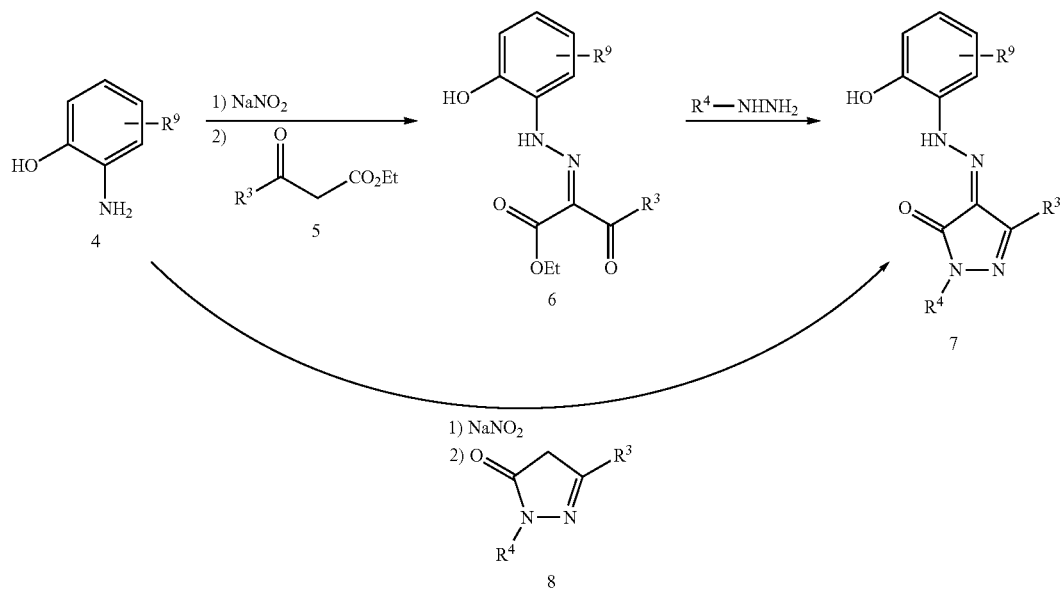

Scheme III describes general synthesis of compounds of Formula V and VI. The compounds of structure 11 can be prepared through a simple amide formation reaction between an acid derivative of structure 9 and a 2-aminothiazole derivative of structure 10 with or without activation.

One of skill in the art will recognize that analogous synthesis schemes may be used to synthesize compounds provided herein. One of skill will recognize that compounds provided herein may be synthesized using other synthesis schemes.

Certain Pharmaceutical Agents

In certain embodiments, a selective GCSFR modulator, or pharmaceutically acceptable salt, ester, amide, and/or prodrug thereof, either alone or combined with one or more pharmaceutically acceptable carriers, forms a pharmaceutical agent. Techniques for formulation and administration of The process of Scheme I describes the general synthesis of compounds of general structure 3 described in Formula III, wherein R can be an alkyl or heteroalkyl derivative. Treatment of the indolone derivatives of general structure 1 with a triethyl orthoester in acetic anhydride affords intermediates of general structure 2. The intermediates of general structure 2 are then condensed with a hydrazide to generate the compounds of general structure 3.

The process of Scheme II describes general synthesis of the compounds of Formula II. Compounds of structure 4 are diazotized under standard conditions and then are coupled with a ketoester of structure 5 to provide hydrazone intermediates of structure 6. Condensation reaction of the intermediate ketoester of structure 6 and a hydrazine affords the final compounds of structure 7. Alternatively, compounds of structure 7 can be obtained directly from coupling reaction of compounds of structure 8 with diazotized compounds of structure 4.

compounds of the present embodiments may be found for example, in "Remington's Pharmaceutical Sciences," Mack Publishing Co., Easton, Pa., 18th edition, 1990, which is incorporated herein by reference in its entirety.

In certain embodiments, a pharmaceutical agent comprising one or more compounds of the present embodiments is prepared using known techniques, including, but not limited to mixing, dissolving, granulating, dragee-making, levigating, emulsifying, encapsulating, entrapping or tabletting processes.

In certain embodiments, a pharmaceutical agent comprising one or more compounds of the present embodiments is a liquid (e.g., a suspension, elixir and/or solution). In certain of such embodiments, a liquid pharmaceutical agent comprising one or more compounds of the present embodiments is prepared using ingredients known in the art, including, but not limited to, water, glycols, oils, alcohols, flavoring agents, preservatives, and coloring agents.

In certain embodiments, a pharmaceutical agent comprising one or more compounds of the present embodiments is a solid (e.g., a powder, tablet, and/or capsule). In certain of such embodiments, a solid pharmaceutical agent comprising one or more compounds of the present embodiments is prepared using ingredients known in the art, including, but not limited to, starches, sugars, diluents, granulating agents, lubricants, binders, and disintegrating agents.

In certain embodiments, a pharmaceutical agent comprising one or more compounds of the present embodiments is formulated as a depot preparation. Certain such depot preparations are typically longer acting than non-depot preparations. In certain embodiments, such preparations are administered by implantation (for example subcutaneously or intramuscularly) or by intramuscular injection. In certain embodiments, depot preparations are prepared using suitable polymeric or hydrophobic materials (for example an emulsion in an acceptable oil) or ion exchange resins, or as sparingly soluble derivatives, for example, as a sparingly soluble salt.

In certain embodiments, a pharmaceutical agent comprising one or more compounds of the present embodiments comprises a delivery system. Examples of delivery systems include, but are not limited to, liposomes and emulsions. Certain delivery systems are useful for preparing certain pharmaceutical agents including those comprising hydrophobic compounds. In certain embodiments, certain organic solvents such as dimethylsulfoxide are used.

In certain embodiments, a pharmaceutical agent comprising one or more compounds of the present embodiments comprises one or more tissue-specific delivery molecules designed to deliver the pharmaceutical agent to specific tissues or cell types. For example, in certain embodiments, pharmaceutical agents include liposomes coated with a tissue-specific antibody.

In certain embodiments, a pharmaceutical agent comprising one or more compounds of the present embodiments comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™, and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical agent comprising one or more compounds of the present embodiments comprises a sustained-release system. A non-limiting example of such a sustained-release system is a semipermeable matrix of solid hydrophobic polymers. In certain embodiments, sustained-release systems may, depending on their chemical nature, release compounds over a period of hours, days, weeks or months.

Certain compounds used in pharmaceutical agent of the present embodiments may be provided as pharmaceutically acceptable salts with pharmaceutically compatible counterions. Pharmaceutically compatible salts may be formed with many acids, including but not limited to hydrochloric, sulfuric, acetic, lactic, tartaric, malic, succinic, etc.

In certain embodiments, a pharmaceutical agent comprising one or more compounds of the present embodiments comprises an active ingredient in a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, a pharmaceutical agent comprising one or more compounds of the present embodiments is formulated as a prodrug. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, a prodrug is an ester. In certain embodiments, such prodrugs are less water soluble than the corresponding active form. In certain instances, such prodrugs possess superior transmittal across cell membranes, where water solubility is detrimental to mobility. In certain embodiments, the ester in such prodrugs is metabolically hydrolyzed to carboxylic acid. In certain instances the carboxylic acid containing compound is the corresponding active form. In certain embodiments, a prodrug comprises a short peptide (polyaminoacid) bound to an acid group. In certain of such embodiments, the peptide is metabolized to form the corresponding active form.

In certain embodiments, a pharmaceutical agent comprising one or more compounds of the present embodiments is useful for treating a conditions or disorder in a mammalian, and particularly in a human patient. Suitable administration routes include, but are not limited to, oral, rectal, transmucosal, intestinal, enteral, topical, suppository, through inhalation, intrathecal, intraventricular, intraperitoneal, intranasal, intraocular and parenteral (e.g., intravenous, intramuscular, intramedullary, and subcutaneous). In certain embodiments, pharmaceutical intrathecals are administered to achieve local rather than systemic exposures. For example, pharmaceutical agents may be injected directly in the area of desired effect (e.g., in the renal or cardiac area).

In certain embodiments, a pharmaceutical agent comprising one or more compounds of the present embodiments is administered in the form of a dosage unit (e.g., tablet, capsule, bolus, etc.). In certain embodiments, such dosage units comprise a selective HGF modulator in a dose from about 1 µg/kg of body weight to about 50 mg/kg of body weight. In certain embodiments, such dosage units comprise a selective HGF modulator in a dose from about 2 µg/kg of body weight to about 25 mg/kg of body weight. In certain embodiments, such dosage units comprise a selective HGF modulator in a dose from about 10 µg/kg of body weight to about 5 mg/kg of body weight. In certain embodiments, pharmaceutical agents are administered as needed, once per day, twice per day, three times per day, or four or more times per day. It is recognized by those skilled in the art that the particular dose, frequency, and duration of administration depends on a number of factors, including, without limitation, the biological activity desired, the condition of the patient, and tolerance for the pharmaceutical agent.

In certain embodiments, a pharmaceutical agent comprising a compound of the present embodiments is prepared for oral administration. In certain of such embodiments, a pharmaceutical agent is formulated by combining one or more compounds of the present embodiments with one or more pharmaceutically acceptable carriers. Certain of such carriers enable compounds of the present embodiments to be formulated as tablets, pills, dragees, capsules, liquids, gels, syrups, slurries, suspensions and the like, for oral ingestion by a patient. In certain embodiments, pharmaceutical agents for oral use are obtained by mixing one or more compounds of the present embodiments and one or more solid excipient. Suitable excipients include, but are not limited to, fillers, such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). In certain embodiments, such a mixture is optionally ground and auxiliaries are optionally added. In certain embodiments, pharmaceutical agents are formed to obtain tablets or dragee cores. In certain embodiments, disintegrating agents (e.g., cross-linked polyvinyl pyrrolidone, agar, or alginic acid or a salt thereof, such as sodium alginate) are added.

In certain embodiments, dragee cores are provided with coatings. In certain of such embodiments, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to tablets or dragee coatings.

In certain embodiments, pharmaceutical agents for oral administration are push-fit capsules made of gelatin. Certain of such push-fit capsules comprise one or more compounds of the present embodiments in admixture with one or more filler such as lactose, binders such as starches, and/or lubricants such as talc or magnesium stearate and, optionally, stabilizers. In certain embodiments, pharmaceutical agents for oral administration are soft, sealed capsules made of gelatin and a plasticizer, such as glycerol or sorbitol. In certain soft capsules, one or more compounds of the present embodiments are be dissolved or suspended in suitable liquids, such as fatty oils, liquid paraffin, or liquid polyethylene glycols. In addition, stabilizers may be added.

In certain embodiments, pharmaceutical agents are prepared for buccal administration. Certain of such pharmaceutical agents are tablets or lozenges formulated in conventional manner.

In certain embodiments, a pharmaceutical agent is prepared for administration by injection (e.g., intravenous, subcutaneous, intramuscular, etc.). In certain of such embodiments, a pharmaceutical agent comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical agents for injection are presented in unit dosage form, e.g., in ampoules or in multi-dose containers. Certain pharmaceutical agents for injection are suspensions, solutions or emulsions in oily or aqueous vehicles, and may contain formulatory agents such as suspending, stabilizing and/or dispersing agents. Certain solvents suitable for use in pharmaceutical agents for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the compounds to allow for the preparation of highly concentrated solutions.

In certain embodiments, a pharmaceutical agent is prepared for transmucosal administration. In certain of such embodiments penetrants appropriate to the barrier to be permeated are used in the formulation. Such penetrants are generally known in the art.

In certain embodiments, a pharmaceutical agent is prepared for administration by inhalation. Certain of such pharmaceutical agents for inhalation are prepared in the form of an aerosol spray in a pressurized pack or a nebulizer. Certain of such pharmaceutical agents comprise a propellant, e.g., dichlorodifluoromethane, trichlorofluoromethane, dichlorotetrafluoroethane, carbon dioxide or other suitable gas. In certain embodiments using a pressurized aerosol, the dosage unit may be determined with a valve that delivers a metered amount. In certain embodiments, capsules and cartridges for use in an inhaler or insufflator may be formulated. Certain of such formulations comprise a powder mixture of a compound of the present embodiments and a suitable powder base such as lactose or starch.

In certain embodiments, a pharmaceutical agent is prepared for rectal administration, such as a suppositories or retention enema. Certain of such pharmaceutical agents comprise known ingredients, such as cocoa butter and/or other glycerides.

In certain embodiments, a pharmaceutical agent is prepared for topical administration. Certain of such pharmaceutical agents comprise bland moisturizing bases, such as ointments or creams. Exemplary suitable ointment bases include, but are not limited to, petrolatum, petrolatum plus volatile silicones, lanolin and water in oil emulsions such as Eucerin™, available from Beiersdorf (Cincinnati, Ohio). Exemplary suitable cream bases include, but are not limited to, Nivea™ Cream, available from Beiersdorf (Cincinnati, Ohio), cold cream (USP), Purpose Cream™, available from Johnson & Johnson (New Brunswick, N.J., hydrophilic ointment (USP) and Lubriderm™, available from Pfizer (Morris Plains, N.J.).

In certain embodiments, the formulation, route of administration and dosage for a pharmaceutical agent of the present embodiments can be chosen in view of a particular patient's condition. (See e.g., Fingl et al. 1975, in "The Pharmacological Basis of Therapeutics", Ch. 1 p. 1, which is incorporated herein by reference in its entirety). In certain embodiments, a pharmaceutical agent is administered as a single dose. In certain embodiments, a pharmaceutical agent is administered as a series of two or more doses administered over one or more days.

In certain embodiments, a pharmaceutical agent of the present embodiments is administered to a patient between about 0.1% and 500%, 5% and 200%, 10% and 100%, 15% and 85%, 25% and 75%, or 40% and 60% of an established human dosage. Where no human dosage is established, a suitable human dosage may be inferred from $ED_{50}$ or $ID_{50}$ values, or other appropriate values derived from in vitro or in vivo studies.

In certain embodiments, a daily dosage regimen for a patient comprises an oral dose of between 0.1 mg and 2000 mg, 5 mg and 1500 mg, 10 mg and 1000 mg, 20 mg and 500 mg, 30 mg and 200 mg, or 40 mg and 100 mg of a compound of the present embodiments. In certain embodiments, a daily dosage regimen is administered as a single daily dose. In certain embodiments, a daily dosage regimen is administered as two, three, four, or more than four doses.

In certain embodiments, a pharmaceutical agent of the present embodiments is administered by continuous intravenous infusion. In certain of such embodiments, from 0.1 mg to 500 mg of a composition of the present embodiments is administered per day.

In certain embodiments, a pharmaceutical agent of the present embodiments is administered for a period of continuous therapy. For example, a pharmaceutical agent of the present embodiments may be administered over a period of days, weeks, months, or years.

Dosage amount, interval between doses, and duration of treatment may be adjusted to achieve a desired effect. In certain embodiments, dosage amount and interval between doses are adjusted to maintain a desired concentration on compound in a patient. For example, in certain embodiments, dosage amount and interval between doses are adjusted to provide plasma concentration of a compound of the present embodiments at an amount sufficient to achieve a desired effect. In certain of such embodiments the plasma concentration is maintained above the minimal effective concentration (MEC). In certain embodiments, pharmaceutical agents of the present embodiments are administered with a dosage regimen designed to maintain a concentration above the MEC for 10-90% of the time, between 30-90% of the time, or between 50-90% of the time.

In certain embodiments in which a pharmaceutical agent is administered locally, the dosage regimen is adjusted to achieve a desired local concentration of a compound of the present embodiments.

In certain embodiments, a pharmaceutical agent may be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound of the present embodiments formulated in a compatible pharmaceutical carrier may also be prepared, placed in an appropriate container, and labeled for treatment of an indicated condition.

In certain embodiments, a pharmaceutical agent is in powder form for constitution with a suitable vehicle, e.g., sterile pyrogen-free water, before use.

Certain Combination Therapies

In certain embodiments, one or more pharmaceutical agents of the present embodiments are co-administered with one or more other pharmaceutical agents. In certain embodiments, such one or more other pharmaceutical agents are designed to treat the same disease or condition as the one or more pharmaceutical agents of the present embodiments. In certain embodiments, such one or more other pharmaceutical agents are designed to treat a different disease or condition as the one or more pharmaceutical agents of the present embodiments. In certain embodiments, such one or more other pharmaceutical agents are designed to treat an undesired effect of one or more pharmaceutical agents of the present embodiments. In certain embodiments, one or more pharmaceutical agents of the present embodiments are co-administered with another pharmaceutical agent to treat an undesired effect of that other pharmaceutical agent. In certain embodiments, one or more pharmaceutical agents of the present embodiments and one or more other pharmaceutical agents are administered at the same time. In certain embodiments, one or more pharmaceutical agents of the present embodiments and one or more other pharmaceutical agents are administered at the different times. In certain embodiments, one or more pharmaceutical agents of the present embodiments and one or more other pharmaceutical agents are prepared together in a single formulation. In certain embodiments, one or more pharmaceutical agents of the present embodiments and one or more other pharmaceutical agents are prepared separately.

Examples of pharmaceutical agents that may be co-administered with a pharmaceutical agent of the present embodiments include, but are not limited to, anti-cancer treatments, including, but not limited to, chemotherapy and radiation treatment; corticosteroids, including but not limited to prednisone; immunoglobulins, including, but not limited to intravenous immunoglobulin (IVIg); analgesics (e.g., acetaminophen); anti-inflammatory agents, including, but not limited to non-steroidal anti-inflammatory drugs (e.g., ibuprofen, COX-1 inhibitors, and COX-2, inhibitors); salicylates; antibiotics; antivirals; antifungal agents; antidiabetic agents (e.g., biguanides, glucosidase inhibitors, insulins, sulfonylureas, and thiazolidenediones); adrenergic modifiers; diuretics; hormones (e.g., anabolic steroids, androgen, estrogen, calcitonin, progestin, somatostan, and thyroid hormones); immunomodulators; muscle relaxants; antihistamines; osteoporosis agents (e.g., biphosphonates, calcitonin, and estrogens); prostaglandins, antineoplastic agents; psychotherapeutic agents; sedatives; poison oak or poison sumac products; antibodies; and vaccines.

In some embodiments, the compounds provided herein can be administered in combination with an additional therapeutic regimen. In some such embodiments, the additional therapeutic regimen can include chemotherapy, bone marrow transplantation, and radiation therapy. In certain embodiments, a compound provided herein can be administered to a subject in combination with harvesting peripheral blood progenitor cells and/or in conjunction with hematopietic stem cell transplantation. Such administration may be done before, during, and/or after such harvesting.

Certain Indications

Certain embodiments include methods of treating or ameliorating a disorder such as a hematopoietic or neurological disorder. Some such methods can include administering an effective amount of a compound provided herein to a subject in need thereof. Examples of disorders that may be treated with the compounds provided herein include granulocytopenia, neutropenia, amyotrophic lateral sclerosis, multiple sclerosis, multiple dystrophy, injury to the nervous system, such as spinal cord injury and injury resulting from trauma or from stroke. In certain embodiments, a disorder can include granulocytopenia. Granulocytopenia can result from chemotherapy, radiation treatment, failure of a bone marrow transplantation, and/or aplastic anemia.

In certain embodiments, the compounds provided herein can be useful to promote growth and/or development of glial cells. Such glial cells may repair nerve cells. In certain embodiments, compounds provided herein are useful to treat psychological disorders, including, but not limited to, cognitive disorders.

In certain embodiments, the compounds provided herein can be useful to treat disorders associated with abnormal function of hematopoiesis, erythropoiesis, granulopoiesis, thrombopoiesis, and myelopoiesis. Examples of such disorders include anemia, neutropenia, thrombocytopenia, cardiovascular disorders, immune/autoimmune disorders, cancers, infectious disorders or diseases, and neurologic disorders. In some embodiments, the compounds provided herein can be administered with additional agents useful to modulate hematopoiesis, erythropoiesis, granulopoiesis, thrombopoiesis, and myelopoiesis.

Certain Methods of Identifying Compounds

Some embodiments of the methods provided herein include identifying therapeutic compounds. Some such therapeutic compounds include compounds that stimulate granulopoiesis, such as GCSFR agonists. Some embodiments include identifying compounds that selectively modulate the activity of a GCSFR. In some embodiments, therapeutic compounds include compounds with reduced activity in the presence of a mutant GCSFR protein compared to a wild type GCSFR protein. In some such embodiments, the mutant GCSFR comprises a mutation in the transmembrane domain of the GCSFR protein, or a mutation proximal to the transmembrane domain of the GCSFR protein.

Some methods for identifying a therapeutic compound include contacting a target cell with a test compound comprising a GCSF receptor agonist, wherein the target cell comprises a mutant GCSF receptor protein; and determining whether the test compound significantly changes the level of activity of the mutant GCSF receptor in the target cell. Some embodiments also include comparing the level of activity of the mutant GCSF receptor in the target cell to the level of activity of a wild type GCSF receptor protein in a cell contacted with the test compound. Some embodiments also include determining whether the level of activity of the mutant GCSF receptor in the target cell contacted with the test compound is less than the level of activity of the wild type GCSF receptor protein in a cell contacted with the test compound. In some embodiments, the cell comprises a mammalian cell. In some embodiments, the cell comprises a human cell. In some embodiments, the cell is not a blood cell.

In some embodiments, the mutant GCSF receptor protein comprises a mutation in the transmembrane domain of the protein or a mutation proximal to the transmembrane domain of the protein. The mutation can include a substitution, deletion or insertion. In some such embodiments, the mutation can include a substitution at the residue corresponding to his-627 of the human GCSF receptor protein, and a substitution at the residue corresponding to Asp-602 of the mouse GCSF receptor protein. In some embodiments the mutant GCSFR includes a substitution at a residue corresponding to a residue proximal to the TM domain of the polypeptide, for example, the substituted residue can be no more than 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30 consecutive residues from the TM domain of the GCSFR polypeptide. In some embodiments, the mutant GCSF receptor comprises a mutant human GCSF receptor. An example polypeptide sequence (SEQ ID No:01) of a human GCSF receptor protein is shown in Table 1.

TABLE 1

| Granulocyte colony-stimulating factor isoform d precursor [Homo sapiens]. ACCESSION NP_001171618 |
| --- |
| 1 magpatqspm klmalqlllw hsalwtvqea tplgpasslp qsfllkcleq vrkiqgdgaa |
| 61 lqeklagcls qlhsglflyq gllqalegis pelgptldtl qldvadfatt iwqqmeelgm |
| 121 apalqptqga mpafasafqr raggvlvash lqsflevsyr vlrhlaqp |

In more methods of identifying a therapeutic compound, a cell is contacted with a test compound and the level of activity of the GCSFR is determined. In some embodiments, the level of activity of the GCSFR in a cell contacted with the test compound is compared to the level of activity of the GCSFR in a cell not contacted with the test compound. In some embodiments, an increase in the activity of the GCSFR in a cell contacted with a test compound compared to the activity in the GCSFR in a cell not contacted with the test compound is indicative that the test compound activates GCSFR. The level of activity of GCSFR can be measured by a variety of methods well know in the art.

Some embodiments for identifying compounds that selectively modulate the activity of a GCSFR can include identifying compounds that increase the activity of a wild type TPO receptor (TPOR) compared to a mutant TPOR. In some embodiments, the mutant TPOR includes a substitution at the residue corresponding to his-499 of the human TPOR polypeptide. In some embodiments, a compound increases the activity of a human TPOR but not a mouse TPOR or monkey TPOR.

In certain embodiments, methods of screening small molecule compound library using the luciferase reporter assays are employed to identify the binding-site selective hGCSFR activator compounds. In certain embodiments, the compound library includes small molecule compounds that activate TPOR by requiring histidine-499 of human TPOR (hTPOR) TM domain or that selectively activate hTPOR but not mouse and monkey TPO receptors. In certain embodiments, the [$^{125}$I]-rhGCSF competitive binding, cell proliferation, and bone marrow cell differential assays are used to characterize the small molecule binding-site selective hGCSFR activator compounds.

EXAMPLES

Example 1

4-Amino-4-oxobutyric Acid N'-(1-phenyl-1-(1-(3,5-dimethoxyphenyl)-2-oxo-6-trifluoromethyl-1,2-dihydroindol-3(Z)-ylidene)methyl)hydrazide (Compound 101)

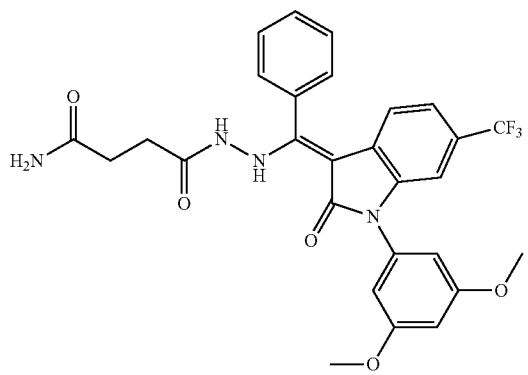 [SMILES: COc1cc(OC)cc(N2C(=O)/C(=C(\NNC(=O)CCC(N)=O)c3ccccc3)c3ccc(C(F)(F)F)cc32)c1]

Compound 101 was prepared according to the procedure described in Scheme I from 1-(3,5-dimethoxyphenyl)-6-trifluoromethyl-1,2-dihydroindol-2-one, triethyl orthobenzoate, and 4-amino-4-oxobutyric acid hydrazide. $^1$H NMR (400 MHz, MeOD) 7.62 (m, 3H), 7.44 (m, 2H), 6.92 (m, 2H), 6.62 (m, 3H), 5.98 (m, 1H), 3.82 (m, 6H), 2.28 (m, 2H), 2.20 (m, 2H). MW=554, LC-MS (M+1)=554.98.

Example 2

4-Amino-4-oxobutyric Acid N'-(1-(1-(3,5-dimethylphenyl)-2-oxo-6-trifluoromethyl-1,2-dihydroindol-3(Z)-ylidene)pentyl)hydrazide (Compound 102)

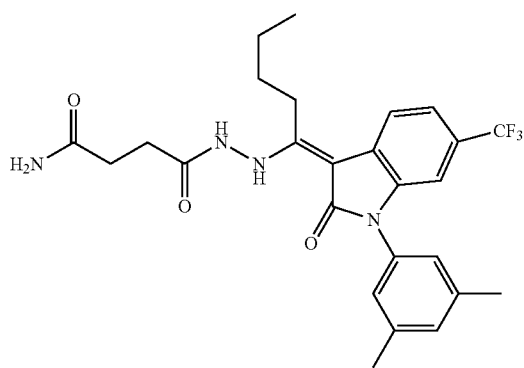 [SMILES: CCCC/C(NNC(=O)CCC(N)=O)=C1/C(=O)N(c2cc(C)cc(C)c2)c2cc(C(F)(F)F)ccc21]

Compound 102 was prepared according to the procedure described in Scheme I from 1-(3,5-dimethylphenyl)-6-trifluoromethyl-1,2-dihydroindol-2-one, triethyl orthovalerate, and 4-amino-4-oxobutyric acid hydrazide. $^1$H NMR (400 MHz, MeOD) 7.53 (d, J=7.5, 1H), 7.38 (d, J=7.5, 1H), 7.18 (s, 1H), 7.05 (s, 1H), 6.94 (s, 1H), 2.95 (m, 2H), 2.62 (s, 4H), 2.42 (m, 6H), 1.73 (m, 2H), 1.65 (m, 2H), 1.05 (t, J=8.0, 3H). MW=502, LC-MS (M+1)=502.99.

Example 3

4-Amino-4-oxobutyric Acid N'-(1-(1-(3,5-dimethylphenyl)-2-oxo-6-trifluoromethyl-1,2-dihydroindol-3(Z)-ylidene)butyl)hydrazide (Compound 103)

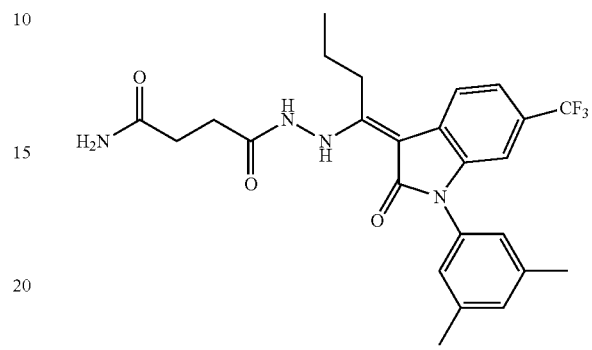

Compound 103 was prepared according to the procedure described in Scheme I from 1-(3,5-dimethylphenyl)-6-trifluoromethyl-1,2-dihydroindol-2-one, triethyl orthobutyrate, and 4-amino-4-oxobutyric acid hydrazide. $^1$H NMR (400 MHz, MeOD) 7.52 (d, J=7.5, 1H), 7.36 (d, J=7.5, 1H), 7.16 (s, 1H), 7.02 (s, 2H), 6.91 (s, 1H), 2.89 (m, 2H), 2.62 (s, 4H), 2.39 (s, 6H), 1.78 (m, 2H), 1.19 (t, J=7.0, 3H). MW=488, LC-MS (M+1)=488.95.

Example 4

Cyclopentanecarboxylic Acid N'-(1-phenyl-1-(1-(3,5-dimethylphenyl)-2-oxo-6-trifluoromethyl-1,2-dihydroindol-3(Z)-ylidene)methyl)hydrazide (Compound 104)

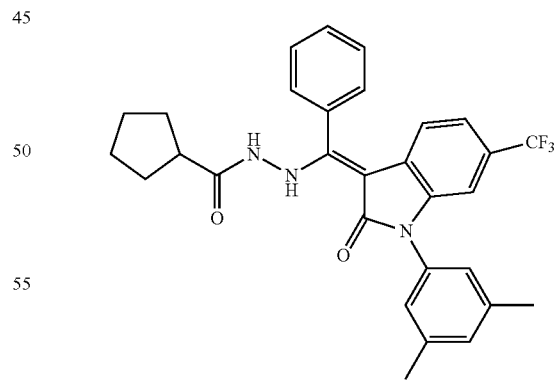

Compound 104 was prepared according to the procedure described in Scheme I from 1-(3,5-dimethylphenyl)-6-trifluoromethyl-1,2-dihydroindol-2-one, triethyl orthobenzoate, and cyclopentylcarboxylic acid hydrazide. MW=519, LC-MS (M+1)=519.98.

Example 5

3-Acetylaminopropionic Acid N'-(1-(1-(3,5-dimethylphenyl)-2-oxo-6-trifluoromethyl-1,2-dihydroindol-3(Z)-ylidene)ethyl)hydrazide (Compound 105)

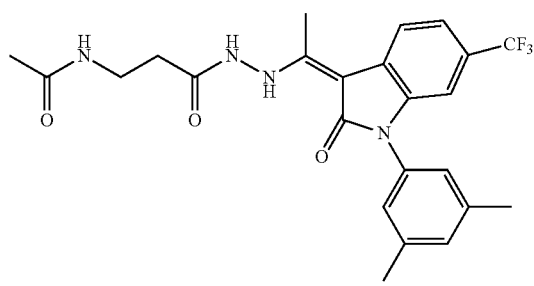 [SMILES: CC(=O)NCCC(=O)NN/C(C)=C1\C(=O)N(c2cc(C)cc(C)c2)c2cc(C(F)(F)F)ccc21]

Compound 105 was prepared according to the procedure described in Scheme I from 1-(3,5-dimethylphenyl)-6-trifluoromethyl-1,2-dihydroindol-2-one, triethyl orthoacetate, and 3-acetylaminopropionic acid hydrazide. $^1$H NMR (400 MHz, MeOD) 7.66 (d, J=7.5, 1H), 7.35 (d, J=7.5, 1H), 7.16 (s, 1H), 7.02 (s, 2H), 6.92 (s, 1H), 3.50 (m, 2H), 2.55 (s, 5H), 2.40 (s, 6H), 1.95 (s, 3H). MW=474, LC-MS (M+1)=475.01.

Example 6

4-Aminobutyric Acid N'-(1-(1-(3,5-dimethylphenyl)-2-oxo-6-trifluoromethyl-1,2-dihydroindol-3(Z)-ylidene)ethyl)hydrazide (Compound 106)

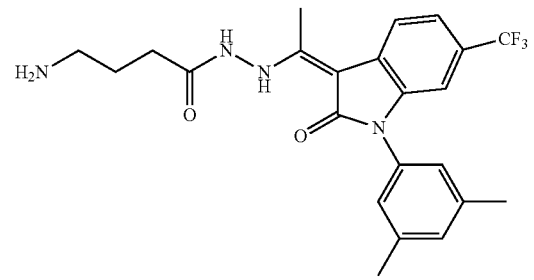 [SMILES: C/C(NNC(=O)CCCN)=C1/C(=O)N(c2cc(C)cc(C)c2)c2cc(C(F)(F)F)ccc21]

Compound 106 was prepared according to the procedure described in Scheme I from 1-(3,5-dimethylphenyl)-6-trifluoromethyl-1,2-dihydroindol-2-one, triethyl orthoacetate, and 4-aminobutyric acid hydrazide.

Example 7

(5-Amino-1-tetrazole)acetic Acid N'-(1-phenyl-1-(1-(3,5-dimethylphenyl)-2-oxo-6-trifluoromethyl-1,2-dihydroindol-3(Z)-ylidene)methyl)hydrazide (Compound 107)

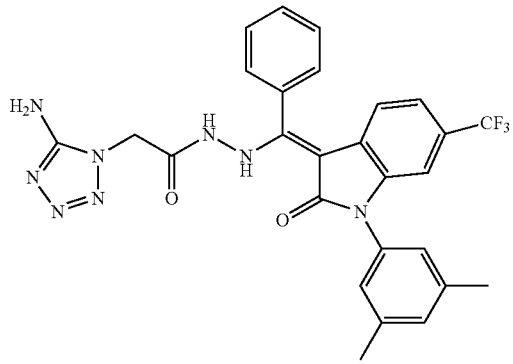 [SMILES: Cc1cc(C)cc(N2C(=O)/C(=C(\NNC(=O)Cn3nnnc3N)c3ccccc3)c3ccc(C(F)(F)F)cc32)c1]

Compound 107 was prepared according to the procedure described in Scheme I from 1-(3,5-dimethylphenyl)-6-trifluoromethyl-1,2-dihydroindol-2-one, triethyl orthobenzoate, and 2-(5-amino-1-tetrazole)acetic acid hydrazide. MW=548, LC-MS (M+1)=549.01.

Example 8

(1-Tetrazole)acetic Acid N'-(1-phenyl-1-(1-(3,5-dimethylphenyl)-2-oxo-6-trifluoromethyl-1,2-dihydroindol-3(Z)-ylidene)methyl)hydrazide (Compound 108)

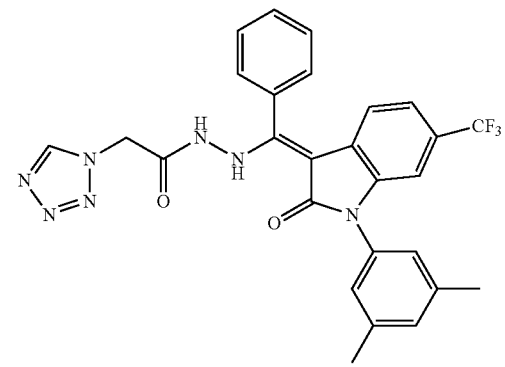 [SMILES: Cc1cc(C)cc(N2C(=O)/C(=C(\NNC(=O)Cn3cnnn3)c3ccccc3)c3ccc(C(F)(F)F)cc32)c1]

Compound 108 was prepared according to the procedure described in Scheme I from 1-(3,5-dimethylphenyl)-6-trifluoromethyl-1,2-dihydroindol-2-one, triethyl orthobenzoate, and 1-tetrazoleacetic acid hydrazide. MW=533, LC-MS (M+1)=533.96.

Example 9

(±)-(1-Benzyl-2-oxo-5-pyrrolidine)carboxylic Acid N'-(1-(1-(3,5-dimethylphenyl)-2-oxo-6-trifluoromethyl-1,2-dihydroindol-3(Z)-ylidene)ethyl)hydrazide (Compound 109)

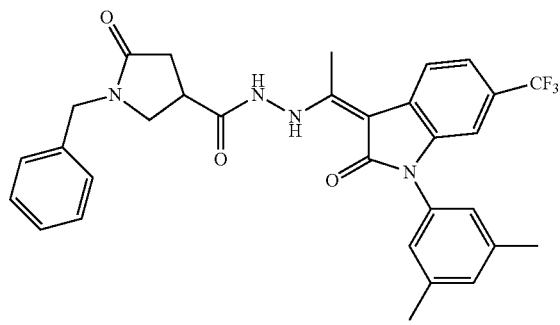 [SMILES: C/C(NNC(=O)C1CC(=O)N(Cc2ccccc2)C1)=C1/C(=O)N(c2cc(C)cc(C)c2)c2cc(C(F)(F)F)ccc21]

Compound 109 was prepared according to the procedure described in Scheme I from 1-(3,5-dimethylphenyl)-6-trifluoromethyl-1,2-dihydroindol-2-one, triethyl orthoacetate, and (1-benzyl-2-oxo-4-pyrrolidine)carboxylic acid hydrazide. MW=562, LC-MS (M+1)=563.05.

Example 10

4-Amino-4-oxobutyric Acid N'-(1-(1-(3-methoxyphenyl)-2-oxo-6-trifluoromethyl-1,2-dihydroindol-3(Z)-ylidene)ethyl)hydrazide (Compound 110)

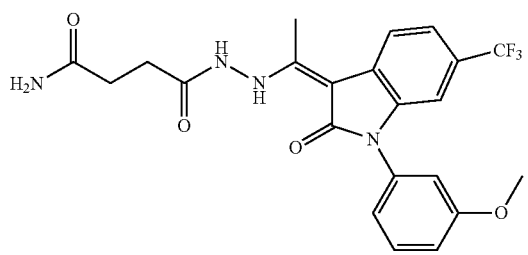 [SMILES: COc1cccc(N2C(=O)/C(=C(/C)NNC(=O)CCC(N)=O)c3ccc(C(F)(F)F)cc32)c1]

Compound 110 was prepared according to the procedure described in Scheme I from 1-(3-methoxyphenyl)-6-trifluoromethyl-1,2-dihydroindol-2-one, triethyl orthoacetate, and 4-amino-4-oxobutyric acid hydrazide. $^1$H NMR (400 MHz, MeOD) 7.67 (m, 1H), 7.50 (m, 1H), 7.35 (m, 1H), 7.06 (m, 1H), 6.98 (m, 3H), 3.85 (m, 3H), 2.60 (m, 7H). MW=462, LC-MS (M+1)=463.02.

Example 11

4-Amino-4-oxobutyric Acid N'-(1-(1-(3,5-dimethoxyphenyl)-2-oxo-6-trifluoromethyl-1,2-dihydroindol-3(Z)-ylidene)ethyl)hydrazide (Compound 111)

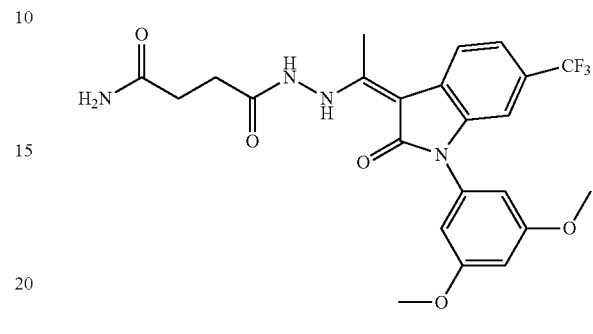

Compound 111 was prepared according to the procedure described in Scheme I from 1-(3,5-dimethoxyphenyl)-6-trifluoromethyl-1,2-dihydroindol-2-one, triethyl orthoacetate, and 4-amino-4-oxobutyric acid hydrazide. $^1$H NMR (400 MHz, MeOD) 7.59 (m, 1H), 7.35 (m, 1H), 7.03 (m, 1H), 6.60 (m, 3H), 3.83 (m, 3H), 2.62 (m, 7H). MW=492, LC-MS (M+1)=492.99.

Example 12

4-Dimethylamino-4-oxobutyric Acid N'-(1-(1-(3,5-dimethylphenyl)-2-oxo-6-trifluoromethyl-1,2-dihydroindol-3(Z)-ylidene)ethyl)hydrazide (Compound 112)

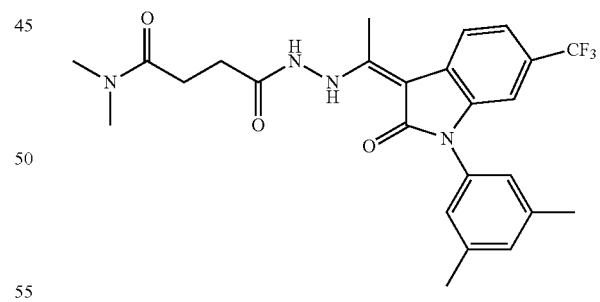

Compound 112 was prepared according to the procedure described in Scheme I from 1-(3,5-dimethylphenyl)-6-trifluoromethyl-1,2-dihydroindol-2-one, triethyl orthoacetate, and 4-dimethylamino-4-oxobutyric acid hydrazide. $^1$H NMR (400 MHz, MeOD) 7.65 (d, J=7.5, 1H), 7.34 (d, J=7.5, 1H), 7.14 (s, 1H), 7.01 (s, 2H), 6.92 (s, 1H), 3.08 (s, 3H), 2.95 (s, 3H), 2.77 (m, 2H), 2.63 (m, 2H), 2.57 (s, 3H), 2.39 (s, 6H). MW=488, LC-MS (M+1)=489.07.

Example 13

4-Hydroxycyclohexyl-1-carboxylic Acid N'-(1-(1-(3,5-dimethylphenyl)-2-oxo-6-trifluoromethyl-1,2-dihydroindol-3(Z)-ylidene)ethyl)hydrazide (Compound 113)

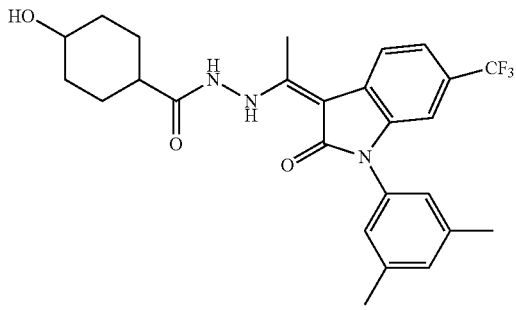 [SMILES: C/C(NNC(=O)C1CCC(O)CC1)=C1/C(=O)N(c2cc(C)cc(C)c2)c2cc(C(F)(F)F)ccc21]

Compound 113 was prepared according to the procedure described in Scheme I from 1-(3,5-dimethylphenyl)-6-trifluoromethyl-1,2-dihydroindol-2-one, triethyl orthoacetate, and 4-hydroxycyclohexylcarboxylic acid hydrazide. MW=487, LC-MS (M+1)=487.99.

Example 14

5-Hydroxy-5-oxopentanoic Acid N'-(1-(1-(3,5-dimethylphenyl)-2-oxo-6-trifluoromethyl-1,2-dihydroindol-3(Z)-ylidene)ethyl)hydrazide (Compound 114)

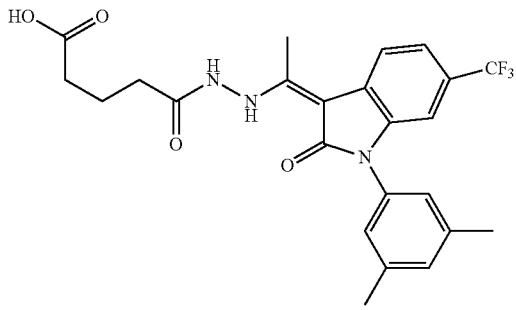 [SMILES: C/C(NNC(=O)CCCC(=O)O)=C1/C(=O)N(c2cc(C)cc(C)c2)c2cc(C(F)(F)F)ccc21]

Compound 114 was prepared according to the procedure described in Scheme I from 1-(3,5-dimethylphenyl)-6-trifluoromethyl-1,2-dihydroindol-2-one, triethyl orthoacetate, and 5-hydroxy-5-oxovaleric acid hydrazide. MW=475, LC-MS (M+1)=475.98.

Example 15

3-Amino-3-oxopropionic Acid N'-(1-(1-(3,5-dimethylphenyl)-2-oxo-6-trifluoromethyl-1,2-dihydroindol-3(Z)-ylidene)ethyl)hydrazide (Compound 115)

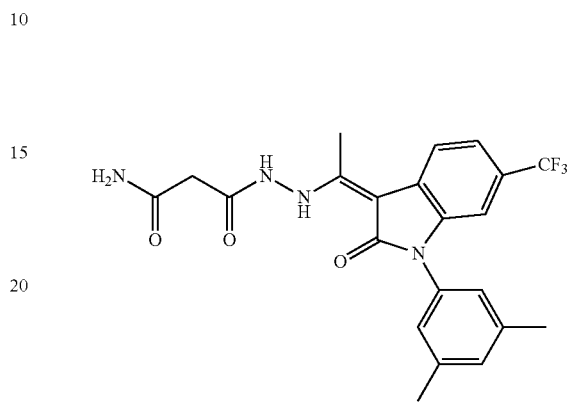

Compound 115 was prepared according to the procedure described in Scheme I from 1-(3,5-dimethylphenyl)-6-trifluoromethyl-1,2-dihydroindol-2-one, triethyl orthoacetate, and 3-amino-3-oxopropionic acid hydrazide. MW=446, LC-MS (M+1)=446.89.

Example 16

(±)-(2-Oxo-3-piperidine)carboxylic Acid N'-(1-(1-(3,5-dimethylphenyl)-2-oxo-6-trifluoromethyl-1,2-dihydroindol-3(Z)-ylidene)ethyl)hydrazide (Compound 116)

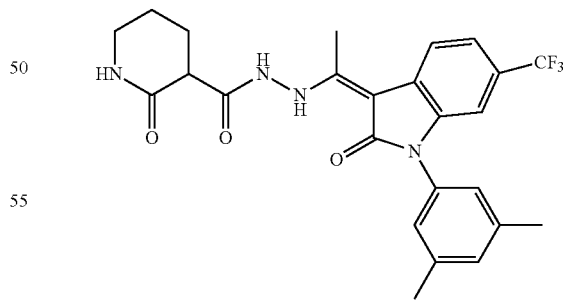

Compound 116 was prepared according to the procedure described in Scheme I from 1-(3,5-dimethylphenyl)-6-trifluoromethyl-1,2-dihydroindol-2-one, triethyl orthoacetate, and 2-oxopiperidinecarboxylic acid hydrazide. MW=486, LC-MS (M+1)=486.98.

Example 17

4-Amino-4-oxobutyric Acid N'-(1-phenyl-1-(1-(3,5-dimethylphenyl)-2-oxo-6-trifluoromethyl-1,2-dihydroindol-3(Z)-ylidene)methyl)hydrazide (Compound 117)

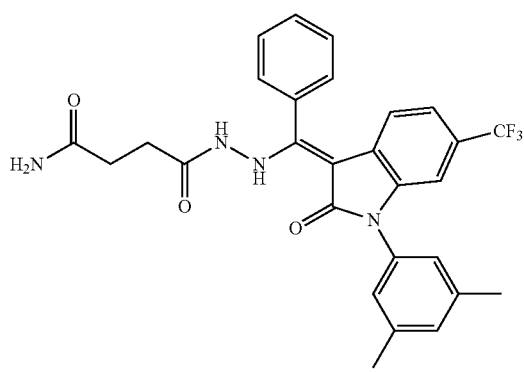 [SMILES: Cc1cc(C)cc(N2C(=O)/C(=C(\NNC(=O)CCC(N)=O)c3ccccc3)c3ccc(C(F)(F)F)cc32)c1]

Compound 117 was prepared according to the procedure described in Scheme I from 1-(3,5-dimethylphenyl)-6-trifluoromethyl-1,2-dihydroindol-2-one, triethyl orthobenzoate, and 4-amino-4-oxobutyric acid hydrazide. 1H NMR (400 MHz, MeOD) 7.63 (m, 3H), 7.45 (d, J=7.5), 7.17 (s, 1H), 7.05 (s, 1H), 6.90 (d, J=7.5, 1H), 6.84 (s, 1H), 5.98 (s, 1H), 2.41 (s, 6H), 2.27 (m, 2H), 2.21 (m, 2H). MW=522, LC-MS (M+1)=523.02.

Example 18

3-(1-Pyrazole)propionic Acid N'-(1-(1-(3,5-dimethylphenyl)-2-oxo-6-trifluoromethyl-1,2-dihydroindol-3(Z)-ylidene)ethyl)hydrazide (Compound 118)

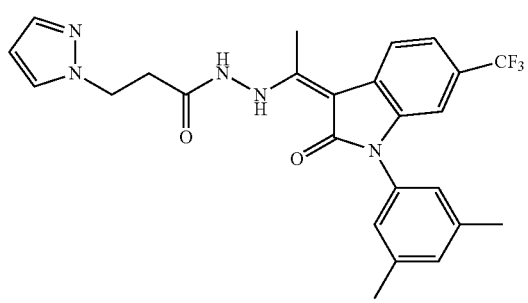 [SMILES: C/C(NNC(=O)CCn1cccn1)=C1/C(=O)N(c2cc(C)cc(C)c2)c2cc(C(F)(F)F)ccc21]

Compound 118 was prepared according to the procedure described in Scheme I from 1-(3,5-dimethylphenyl)-6-trifluoromethyl-1,2-dihydroindol-2-one, triethyl orthoacetate, and 3-(1-pyrazole)propionic acid hydrazide. MW=483, LC-MS (M+1)=484.01.

Example 19

4-Hydroxy-4-oxobutyric Acid N'-(1-(1-(4-methylphenyl)-2-oxo-6-trifluoromethyl-1,2-dihydroindol-3(Z)-ylidene)ethyl)hydrazide (Compound 119)

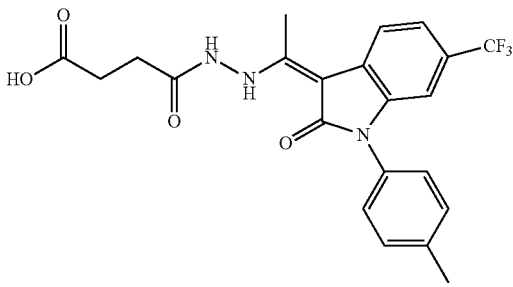 [SMILES: C/C(NNC(=O)CCC(=O)O)=C1/C(=O)N(c2ccc(C)cc2)c2cc(C(F)(F)F)ccc21]

Compound 119 was prepared according to the procedure described in Scheme I from 1-(4-methylphenyl)-6-trifluoromethyl-1,2-dihydroindol-2-one, triethyl orthoacetate, and succinic acid monohydrazide. $^1$H NMR (400 MHz, MeOD) 7.66 (m, 1H), 7.42 (m, 2H), 7.35 (m, 1H), 7.30 (m, 2H), 6.92 (m, 1H), 2.67 (m, 2H), 2.61 (m, 2H), 2.58 (m, 3H), 2.46 (m, 3H). MW=447, LC-MS (M+1)=447.97.

Example 20

4-Amino-4-oxobutyric Acid N'-(1-(3,5-dimethylphenyl)-2-oxo-6-trifluoromethyl-1,2-dihydroindol-3(Z)-ylidene)methylhydrazide (Compound 120)

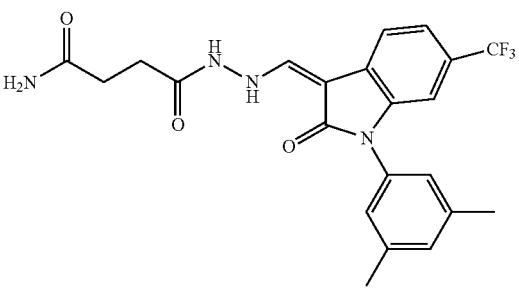 [SMILES: Cc1cc(C)cc(N2C(=O)/C(=C\NNC(=O)CCC(N)=O)c3ccc(C(F)(F)F)cc32)c1]

Compound 120 was prepared according to the procedure described in Scheme I from 1-(3,5-dimethylphenyl)-6-trifluoromethyl-1,2-dihydroindol-2-one, triethyl orthocarboxylate, and 4-amino-4-oxobutyric acid hydrazide. $^1$H NMR (400 MHz, MeOD) 7.58 (m, 1H), 7.31 (m. 1H), 7.15 (s, 1H), 7.04 (s, 2H), 6.90 (s, 1H), 2.61 (m, 4H), 2.41 (s, 6H). MW=446, LC-MS (M+1)=446.96.

Example 21

4-Amino-4-oxobutyric Acid N'-(1-(1-(4-methylphenyl)-2-oxo-6-trifluoromethyl-1,2-dihydroindol-3(Z)-ylidene)ethyl)hydrazide (Compound 121)

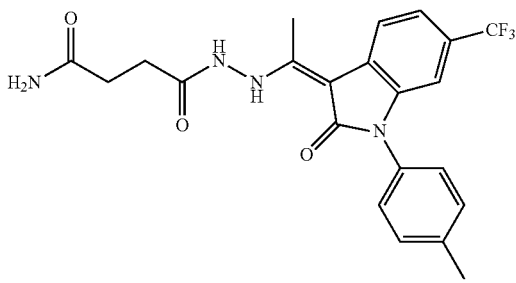 [SMILES: C/C(NNC(=O)CCC(N)=O)=C1/C(=O)N(c2ccc(C)cc2)c2cc(C(F)(F)F)ccc21]

Compound 121 was prepared according to the procedure described in Scheme I from 1-(4-methylphenyl)-6-trifluoromethyl-1,2-dihydroindol-2-one, triethyl orthoacetate, and 4-amino-4-oxobutyric acid hydrazide. $^1$H NMR (400 MHz, MeOD) 7.66 (d, J=7.5, 1H), 7.42 (d, J=7.5, 2H), 7.35 (d, J=7.5, 1H), 7.28 (d, J=7.5, 2H), 6.93 (s, 1H), 2.62 (m, 4H), 2.57 (s, 3H), 2.46 (s, 3H). MW=446, LC-MS (M+1)=446.96.

Example 22

Cyclopropylcarboxylic Acid N'-(1-(1-(3-methylphenyl)-2-oxo-6-trifluoromethyl-1,2-dihydroindol-3(Z)-ylidene)ethyl)hydrazide (Compound 122)

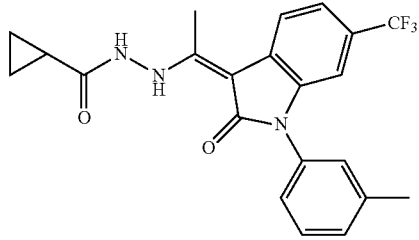 [SMILES: C/C(NNC(=O)C1CC1)=C1/C(=O)N(c2cccc(C)c2)c2cc(C(F)(F)F)ccc21]

Compound 122 was prepared according to the procedure described in Scheme I from 1-(3-methylphenyl)-6-trifluoromethyl-1,2-dihydroindol-2-one, triethyl orthoacetate, and cyclopropylcarboxlic acid hydrazide. $^1$H NMR (400 MHz, MeOD) 7.66 (m, 1H), 7.46 (m, 1H), 7.34 (m, 2H), 7.22 (m, 2H), 6.92 (s, 1H), 2.55 (s, 3H), 2.43 (s, 3H), 1.71 (m, 1H), 0.95 (m, 4H). MW=415, LC-MS (M+1)=415.99.

Example 23

4-Hydroxybutyric Acid N'-(1-phenyl-1-(1-(3,5-dimethylphenyl)-2-oxo-6-trifluoromethyl-1,2-dihydroindol-3(Z)-ylidene)methyl)hydrazide (Compound 123)

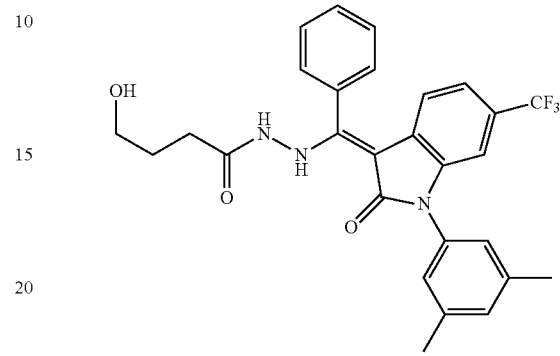

Compound 123 was prepared according to the procedure described in Scheme I from 1-(3,5-dimethylphenyl)-6-trifluoromethyl-1,2-dihydroindol-2-one, triethyl orthobenzoate, and 4-hydroxybutyric acid hydrazide. MW=509, LC-MS (M+1)=509.99.

Example 24

Cyclopropylcarboxylic Acid N'-(1-(1-(3,5-dimethylphenyl)-2-oxo-6-trifluoromethyl-1,2-dihydroindol-3(Z)-ylidene)-1-(2-furyl)methyl)hydrazide (Compound 124)

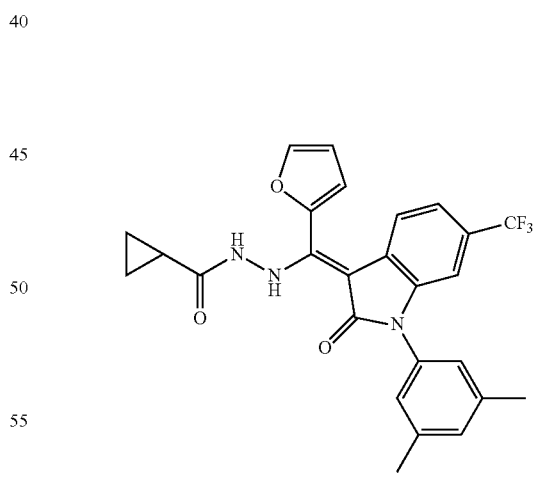

Compound 124 was prepared according to the procedure described in Scheme I from 1-(3,5-dimethylphenyl)-6-trifluoromethyl-1,2-dihydroindol-2-one, triethyl ortho-(2-furano)carboxylate, and cyclopropylcarboxylic acid hydrazide.

Example 25

Cyclopropylcarboxylic Acid N'-(1-(1-(4-methylphenyl)-2-oxo-6-trifluoromethyl-1,2-dihydroindol-3(Z)-ylidene)ethyl)hydrazide (Compound 125)

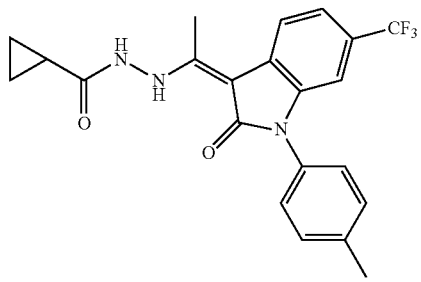 [SMILES: C/C(NNC(=O)C1CC1)=C1/C(=O)N(c2ccc(C)cc2)c2cc(C(F)(F)F)ccc21]

Compound 125 was prepared according to the procedure described in Scheme I from 1-(4-methylphenyl)-6-trifluoromethyl-1,2-dihydroindol-2-one, triethyl orthoacetate, and cyclopropylcarboxylic acid hydrazide. $^1$H NMR (400 MHz, MeOD) 7.65 (d, J=7.5, 1H), 7.42 (d, J=7.5, 2H), 7.35 (d, J=7.5, 1H), 7.28 (d, J=7.5, 2H), 6.92 (s, 1H), 2.55 (s, 3H), 2.45 (s, 3H), 1.71 (m, 1H), 0.95 (m, 4H). MW=415, LC-MS (M+1)=415.99.

Example 26

4-Hydroxybutyric Acid N'-(1-(1-(3-trifluoromethylphenyl)-2-oxo-6-trifluoromethyl-1,2-dihydroindol-3(Z)-ylidene)ethyl)hydrazide (Compound 126)

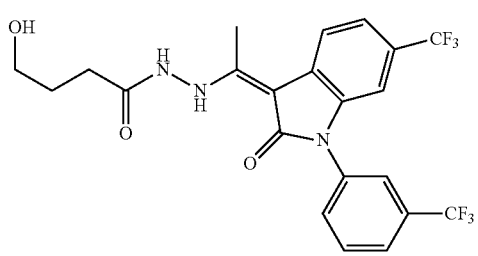 [SMILES: C/C(NNC(=O)CCCO)=C1/C(=O)N(c2cccc(C(F)(F)F)c2)c2cc(C(F)(F)F)ccc21]

Compound 126 was prepared according to the procedure described in Scheme I from 1-(3-trifluoromethylphenyl)-6-trifluoromethyl-1,2-dihydroindol-2-one, triethyl orthoacetate, and 4-hydroxybutyric acid hydrazide. MW=487, LC-MS (M+1)=487.99.

Example 27

Butyric Acid N'-(1-(1-(3,5-dimethylphenyl)-2-oxo-6-trifluoromethyl-1,2-dihydroindol-3(Z)-ylidene)ethyl)hydrazide (Compound 127)

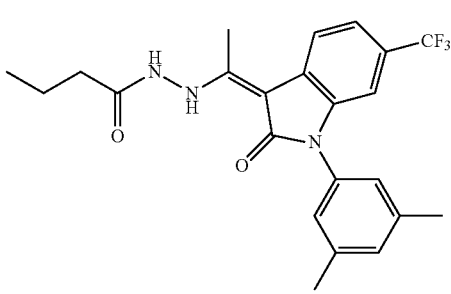 [SMILES: CCCC(=O)NN/C(C)=C1\C(=O)N(c2cc(C)cc(C)c2)c2cc(C(F)(F)F)ccc21]

Compound 127 was prepared according to the procedure described in Scheme I from 1-(3,5-dimethylphenyl)-6-trifluoromethyl-1,2-dihydroindol-2-one, triethyl orthoacetate, and butyric acid hydrazide. MW=431, LC-MS (M+1)=431.98.

Example 28

4-Amino-4-oxobutyric Acid N'-(1-(1-(3,5-dimethylphenyl)-2-oxo-6-trifluoromethyl-1,2-dihydroindol-3(Z)-ylidene)ethyl)hydrazide (Compound 128)

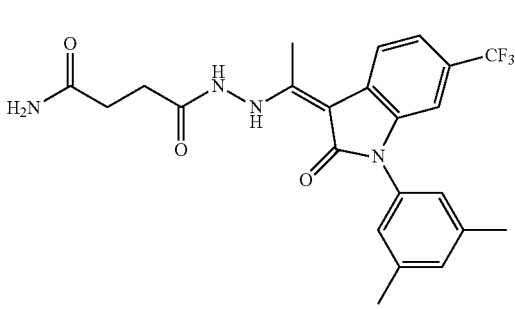 [SMILES: C/C(NNC(=O)CCC(N)=O)=C1/C(=O)N(c2cc(C)cc(C)c2)c2cc(C(F)(F)F)ccc21]

Compound 128 was prepared according to the procedure described in Scheme I from 1-(3,5-dimethylphenyl)-6-trifluoromethyl-1,2-dihydroindol-2-one, triethyl orthoacetate, and 4-amino-4-oxobutyric acid hydrazide. MW=460, LC-MS (M+1)=461.00.

Example 29

4-Phenylamino-4-oxobutyric Acid N'-(1-(1-(3,5-dimethylphenyl)-2-oxo-6-trifluoromethyl-1,2-dihydroindol-3(Z)-ylidene)ethyl)hydrazide (Compound 129)

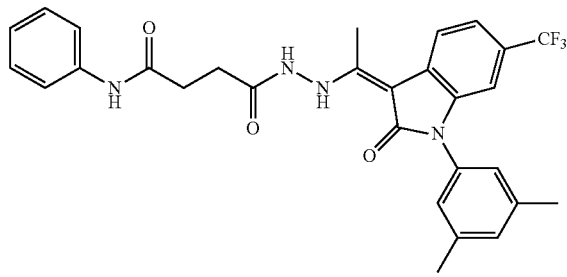 [SMILES: C/C(NNC(=O)CCC(=O)Nc1ccccc1)=C1/C(=O)N(c2cc(C)cc(C)c2)c2cc(C(F)(F)F)ccc21]

Compound 129 was prepared according to the procedure described in Scheme I from 1-(3,5-dimethylphenyl)-6-trifluoromethyl-1,2-dihydroindol-2-one, triethyl orthoacetate, and 4-phenylamino-4-oxobutyric acid hydrazide. MW=536, LC-MS (M+1)=537.06.

Example 30

4-Hydroxybutyric Acid N'-(1-(1-(4-methylphenyl)-2-oxo-6-trifluoromethyl-1,2-dihydroindol-3(Z)-ylidene)ethyl)hydrazide (Compound 130)

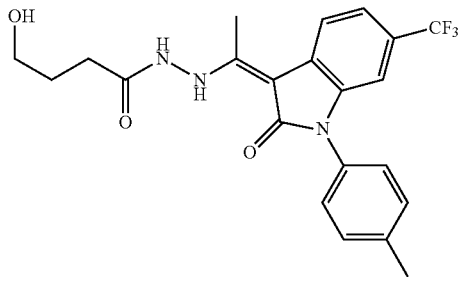 [SMILES: C/C(NNC(=O)CCCO)=C1/C(=O)N(c2ccc(C)cc2)c2cc(C(F)(F)F)ccc21]

Compound 130 was prepared according to the procedure described in Scheme I from 1-(4-methylphenyl)-6-trifluoromethyl-1,2-dihydroindol-2-one, triethyl orthoacetate, and 4-hydroxybutyric acid hydrazide. MW=433, LC-MS (M+1)=433.94.

Example 31

4-Hydroxybutyric Acid N'-(1-(1-(3-methylphenyl)-2-oxo-6-trifluoromethyl-1,2-dihydroindol-3(Z)-ylidene)ethyl)hydrazide (Compound 131)

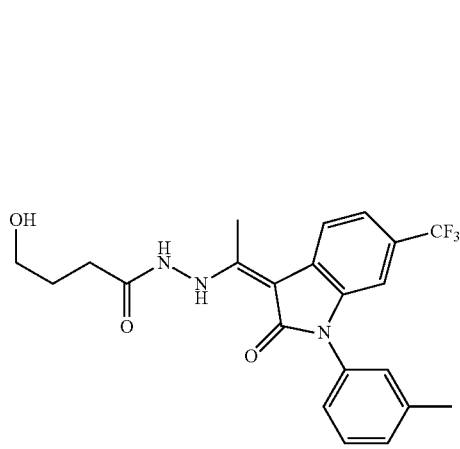 [SMILES: C/C(NNC(=O)CCCO)=C1/C(=O)N(c2cccc(C)c2)c2cc(C(F)(F)F)ccc21]

Compound 131 was prepared according to the procedure described in Scheme I from 1-(3-methylphenyl)-6-trifluoromethyl-1,2-dihydroindol-2-one, triethyl orthoacetate, and 4-hydroxybutyric acid hydrazide. MW=433, LC-MS (M+1)=433.94.

Example 32

Cyclopropylcarboxylic Acid N'-(1-(3,5-dimethylphenyl)-2-oxo-6-trifluoromethyl-1,2-dihydroindol-3(Z)-ylidene)methylhydrazide (Compound 132)

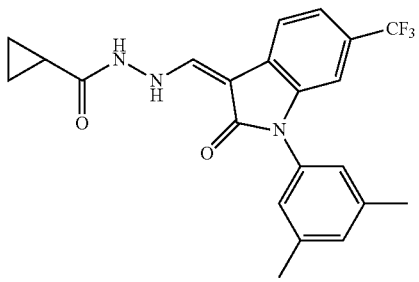 [SMILES: Cc1cc(C)cc(N2C(=O)/C(=C\NNC(=O)C3CC3)c3ccc(C(F)(F)F)cc32)c1]

Compound 132 was prepared according to the procedure described in Scheme I from 1-(3,5-dimethylphenyl)-6-trifluoromethyl-1,2-dihydroindol-2-one, triethyl orthocarboxylate, and cyclopropylcarboxylic acid hydrazide.

Example 33

3-Methoxypropionic Acid N'-(1-(1-(3,5-dimethylphenyl)-2-oxo-6-trifluoromethyl-1,2-dihydroindol-3(Z)-ylidene)ethyl)hydrazide (Compound 133)

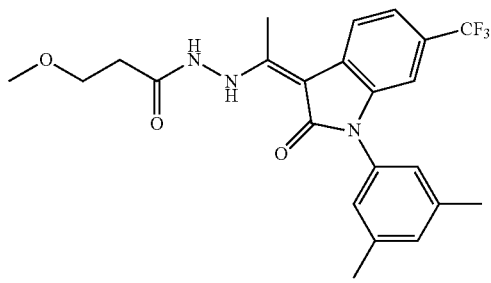

Compound 133 was prepared according to the procedure described in Scheme I from 1-(3,5-dimethylphenyl)-6-trifluoromethyl-1,2-dihydroindol-2-one, triethyl orthoacetate, and 3-methoxypropionic acid hydrazide. MW=447, LC-MS (M+1)=447.98.

Example 34

3-Indoleacetic Acid N'-(1-(1-(3,5-dimethylphenyl)-2-oxo-6-trifluoromethyl-1,2-dihydroindol-3(Z)-ylidene)ethyl)hydrazide (Compound 134)

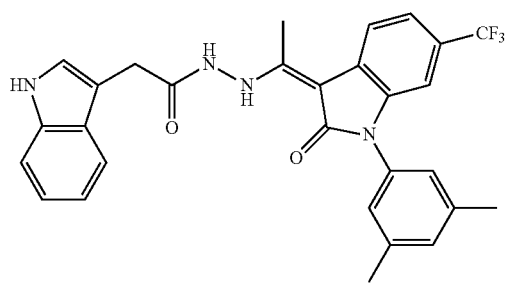 [SMILES: C/C(NNC(=O)Cc1c[nH]c2ccccc12)=C1/C(=O)N(c2cc(C)cc(C)c2)c2cc(C(F)(F)F)ccc21]

Compound 134 was prepared according to the procedure described in Scheme I from 1-(3,5-dimethylphenyl)-6-trifluoromethyl-1,2-dihydroindol-2-one, triethyl orthoacetate, and 3-indoleacetic acid hydrazide. MW=518, LC-MS (M+1)=519.04.

Example 35

4-Hydroxybutyric Acid N'-(1-(1-phenyl-2-oxo-6-methoxy-1,2-dihydroindol-3(Z)-ylidene)ethyl)hydrazide (Compound 135)

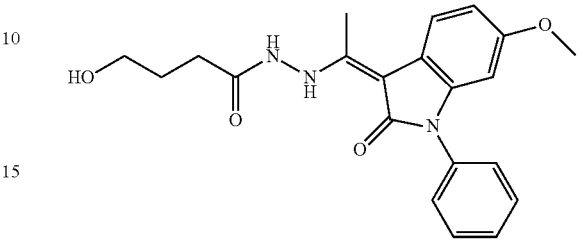

Compound 135 was prepared according to the procedure described in Scheme I from 1-phenyl-6-methoxy-1,2-dihydroindol-2-one, triethyl orthoacetate, and 4-hydroxybutyric acid hydrazide. MW=381, LC-MS (M+1)=382.00.

Example 36

4-Hydroxybutyric Acid N'-(1-(1-phenyl-2-oxo-6-methyl-1,2-dihydroindol-3(Z)-ylidene)ethyl)hydrazide (Compound 136)

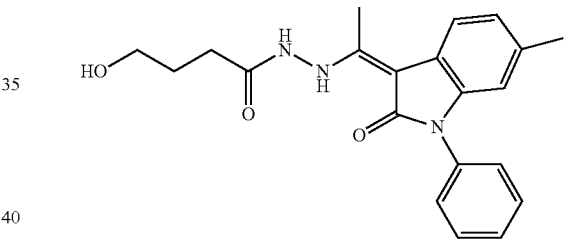

Compound 136 was prepared according to the procedure described in Scheme I from 1-phenyl-6-methyl-1,2-dihydroindol-2-one, triethyl orthoacetate, and 4-hydroxybutyric acid hydrazide. MW=365, LC-MS (M+1)=366.01.

Example 37

4-Hydroxyvaleric Acid N'-(1-(1-(3,5-dimethylphenyl)-2-oxo-6-trifluoromethyl-1,2-dihydroindol-3(Z)-ylidene)ethyl)hydrazide (Compound 137)

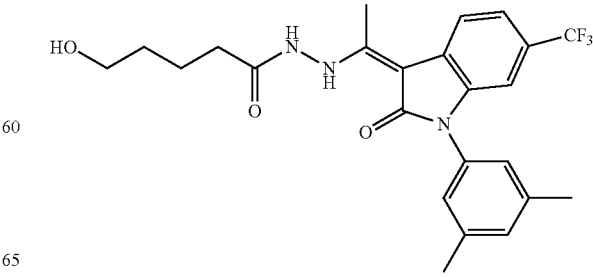

Compound 137 was prepared according to the procedure described in Scheme I from 1-(3,5-dimethylphenyl)-6-trifluoromethyl-1,2-dihydroindol-2-one, triethyl orthoacetate, and 4-hydroxyvaleric acid hydrazide. MW=461, LC-MS (M+1)=461.94.

Example 38

3-Hydroxypropionic Acid N'-(1-(1-(3,5-dimethylphenyl)-2-oxo-6-trifluoromethyl-1,2-dihydroindol-3(Z)-ylidene)ethyl)hydrazide (Compound 138)

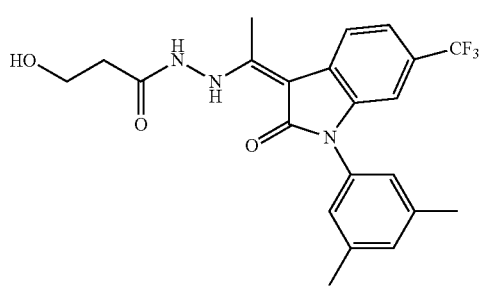 [SMILES: C/C(NNC(=O)CCO)=C1/C(=O)N(c2cc(C)cc(C)c2)c2cc(C(F)(F)F)ccc21]

Compound 138 was prepared according to the procedure described in Scheme I from 1-(3,5-dimethylphenyl)-6-trifluoromethyl-1,2-dihydroindol-2-one, triethyl orthoacetate, and 3-hydroxypropionic acid hydrazide. MW=433, LC-MS (M+1)=433.94.

Example 39

4-Hydroxybutyric Acid N'-(1-(1-phenyl-2-oxo-6-cyano-1,2-dihydroindol-3(Z)-ylidene)ethyl)hydrazide (Compound 139)

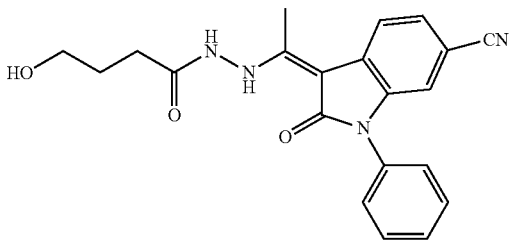 [SMILES: C/C(NNC(=O)CCCO)=C1/C(=O)N(c2ccccc2)c2cc(C#N)ccc21]

Compound 139 was prepared according to the procedure described in Scheme I from 1-phenyl-6-trifluoromethyl-1,2-dihydroindol-2-one, triethyl orthoacetate, and 4-hydroxybutyric acid hydrazide. MW=376, LC-MS (M+1)=377.01.

Example 40

4-Hydroxybutyric Acid N'-(1-(1-(3,5-dimethylphenyl)-2-oxo-6-trifluoromethyl-1,2-dihydroindol-3(Z)-ylidene)propyl)hydrazide (Compound 140)

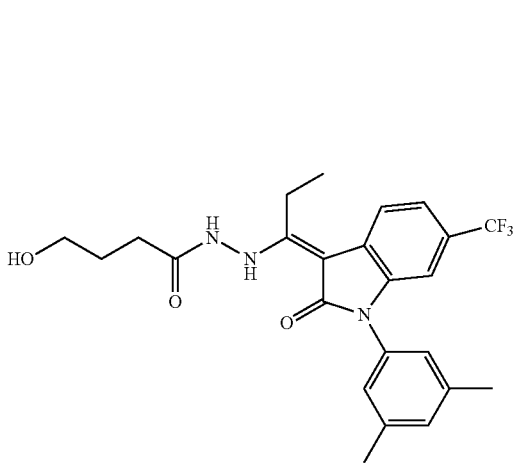 [SMILES: CC/C(NNC(=O)CCCO)=C1/C(=O)N(c2cc(C)cc(C)c2)c2cc(C(F)(F)F)ccc21]

Compound 140 was prepared according to the procedure described in Scheme I from 1-(3,5-dimethylphenyl)-6-trifluoromethyl-1,2-dihydroindol-2-one, triethyl orthopropionate, and 4-hydroxybutyric acid hydrazide. MW=461, LC-MS (M+1)=461.94.

Example 41

Aminocarboxylic Acid N'-(1-(1-(3,5-dimethylphenyl)-2-oxo-6-trifluoromethyl-1,2-dihydroindol-3(Z)-ylidene)propyl)hydrazide (Compound 141)

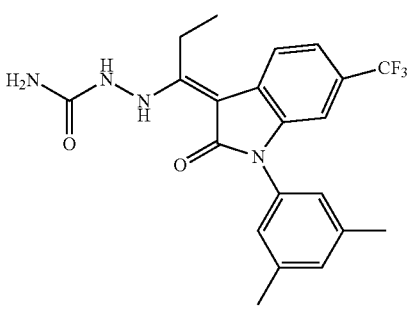 [SMILES: CC/C(NNC(N)=O)=C1/C(=O)N(c2cc(C)cc(C)c2)c2cc(C(F)(F)F)ccc21]

Compound 141 was prepared according to the procedure described in Scheme I from 1-(3,5-dimethylphenyl)-6-trifluoromethyl-1,2-dihydroindol-2-one, triethyl orthopropionate, and 1-aminocarboxylic acid hydrazide. MW=418, LC-MS (M+1)=418.96.

Example 42

4-Hydroxybutyric Acid N'-(1-(1-phenyl-2-oxo-6-chloro-1,2-dihydroindol-3(Z)-ylidene)ethyl)hydrazide (Compound 142)

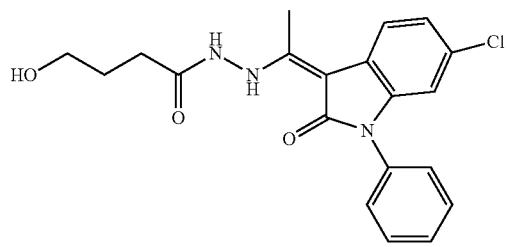 [SMILES: C/C(NNC(=O)CCCO)=C1/C(=O)N(c2ccccc2)c2cc(Cl)ccc21]

Compound 142 was prepared according to the procedure described in Scheme I from 1-phenyl-6-chloro-1,2-dihydroindol-2-one, triethyl orthoacetate, and 4-hydroxybutyric acid hydrazide.

Example 43

Aminocarboxylic Acid N'-(1-(3,5-dimethylphenyl)-2-oxo-6-trifluoromethyl-1,2-dihydroindol-3(Z)-ylidene)methylhydrazide (Compound 143)

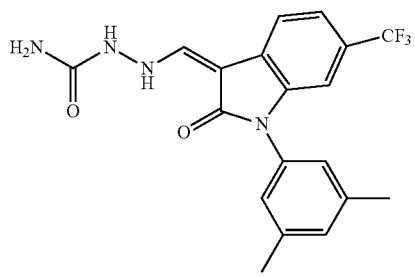 [SMILES: Cc1cc(C)cc(N2C(=O)/C(=C\NNC(N)=O)c3ccc(C(F)(F)F)cc32)c1]

Compound 143 was prepared according to the procedure described in Scheme I from 1-(3,5-dimethylphenyl)-6-trifluoromethyl-1,2-dihydroindol-2-one, triethyl orthocarboxylate, and 1-aminocarboxylic acid hydrazide. MW=390, LC-MS (M+1)=390.97.

Example 44

4-Hydroxybutyric Acid N'-(1-(1-(3,5-dimethylphenyl)-2-oxo-6-trifluoromethyl-1,2-dihydroindol-3(Z)-ylidene)ethyl)hydrazide (Compound 144)

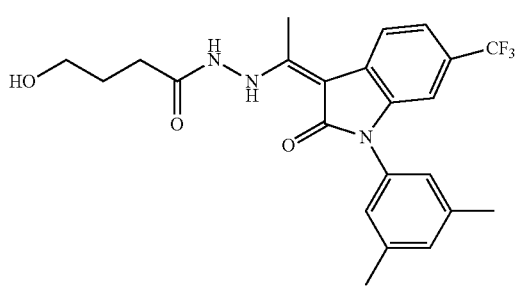 [SMILES: C/C(NNC(=O)CCCO)=C1/C(=O)N(c2cc(C)cc(C)c2)c2cc(C(F)(F)F)ccc21]

Compound 144 was prepared according to the procedure described in Scheme I from 1-(3,5-dimethylphenyl)-6-trifluoromethyl-1,2-dihydroindol-2-one, triethyl orthoacetate, and 4-hydroxybutyric acid hydrazide. MW=447, LC-MS (M+1)=447.91.

Example 45

3-Dimethylaminopropionic Acid N'-(1-(1-(3,5-dimethylphenyl)-2-oxo-6-trifluoromethyl-1,2-dihydroindol-3(Z)-ylidene)ethyl)hydrazide (Compound 145)

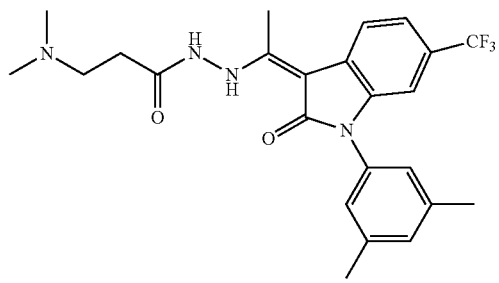

Compound 145 was prepared according to the procedure described in Scheme I from 1-(3,5-dimethylphenyl)-6-trifluoromethyl-1,2-dihydroindol-2-one, triethyl orthoacetate, and 3-dimethylaminopropionic acid hydrazide. MW=460, LC-MS (M+1)=461.00.

Example 46

2-Cyanoacetic Acid N'-(1-(1-(3,5-dimethylphenyl)-2-oxo-6-trifluoromethyl-1,2-dihydroindol-3(Z)-ylidene)ethyl)hydrazide (Compound 146)

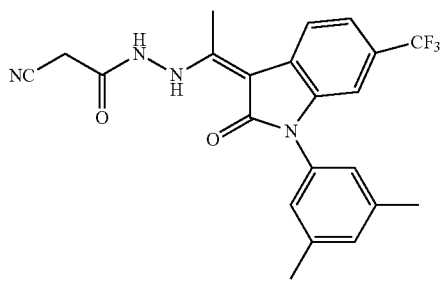 [SMILES: C/C(NNC(=O)CC#N)=C1/C(=O)N(c2cc(C)cc(C)c2)c2cc(C(F)(F)F)ccc21]

Compound 146 was prepared according to the procedure described in Scheme I from 1-(3,5-dimethylphenyl)-6-trifluoromethyl-1,2-dihydroindol-2-one, triethyl orthoacetate, and cyanoacetic acid hydrazide. MW=428, LC-MS (M+1)=428.95.

Example 47

(±)-3-Hydroxybutyric Acid N'-(1-(1-(3,5-dimethylphenyl)-2-oxo-6-trifluoromethyl-1,2-dihydroindol-3(Z)-ylidene)ethyl)hydrazide (Compound 147)

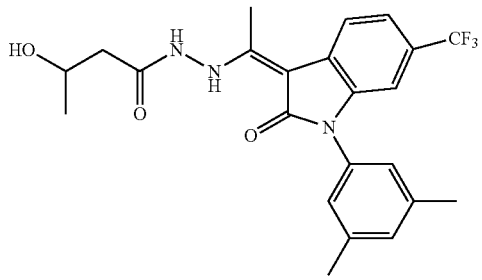 [SMILES: C/C(NNC(=O)CC(C)O)=C1/C(=O)N(c2cc(C)cc(C)c2)c2cc(C(F)(F)F)ccc21]

Compound 147 was prepared according to the procedure described in Scheme I from 1-(3,5-dimethylphenyl)-6-trifluoromethyl-1,2-dihydroindol-2-one, triethyl orthoacetate, and 3-hydroxybutyric acid hydrazide. 1H NMR (400 MHz, DMSO-$d_6$) 11.55 (s, 1H), 10.56 (s, 1H), 7.70 (d, J=8.0, 1H), 7.38 (d, J=8.0, 1H), 7.12 (s, 1H), 7.06 (s, 1H), 6.89 (s, 1H), 4.88 (d, J=8.0, 1H), 4.39 (t, J=5.0 and 8.0, 1H), 4.05 (m, 2H), 2.58 (s, 3H), 2.49 (s, 6H), 2.32 (d, J=8.0, 3H).

Example 48

Cyclopropylcarboxylic Acid N'-(1-(1-(3,5-dimethylphenyl)-2-oxo-6-trifluoromethyl-1,2-dihydroindol-3(Z)-ylidene)ethyl)hydrazide (Compound 148)

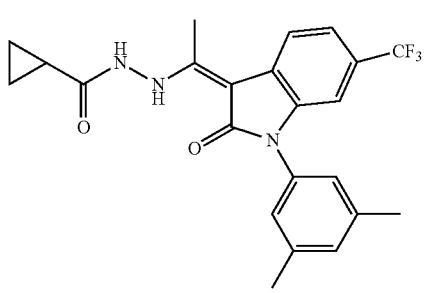 [SMILES: C/C(NNC(=O)C1CC1)=C1/C(=O)N(c2cc(C)cc(C)c2)c2cc(C(F)(F)F)ccc21]

Compound 148 was prepared according to the procedure described in Scheme I from 1-(3,5-dimethylphenyl)-6-trifluoromethyl-1,2-dihydroindol-2-one, triethyl orthoacetate, and cyclopropylcarboxylic acid hydrazide. MW=429, LC-MS (M+1)=429.89.

Example 49

Aminothiocarboxylic Acid N'-(1-(3,5-dimethylphenyl)-2-oxo-6-trifluoromethyl-1,2-dihydroindol-3(Z)-ylidene)methylhydrazide (Compound 149)

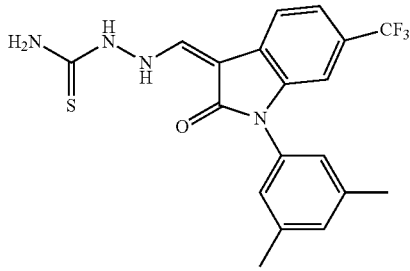 [SMILES: Cc1cc(C)cc(N2C(=O)/C(=C\NNC(N)=S)c3ccc(C(F)(F)F)cc32)c1]

Compound 149 was prepared according to the procedure described in Scheme I from 1-(3,5-dimethylphenyl)-6-trifluoromethyl-1,2-dihydroindol-2-one, triethyl orthocarboxylate, and 1-aminothiocarboxylic acid hydrazide. MW=420, LC-MS (M+1)=420.92.

Example 50

Acetic Acid N'-(1-(1-phenyl-2-oxo-6-trifluoromethyl-1,2-dihydroindol-3(Z)-ylidene)ethyl)hydrazide (Compound 150)

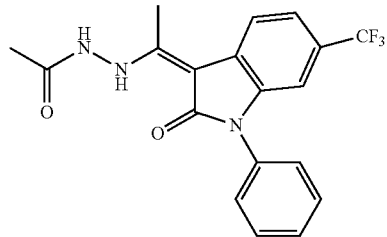 [SMILES: CC(=O)NN/C(C)=C1\C(=O)N(c2ccccc2)c2cc(C(F)(F)F)ccc21]

Compound 150 was prepared according to the procedure described in Scheme I from 1-phenyl-6-trifluoromethyl-1,2-dihydroindol-2-one, triethyl orthoacetate, and acetic acid hydrazide.

Example 51

(±)-2-Hydroxypropionic Acid N'-(1-(1-(3,5-dimethylphenyl)-2-oxo-6-trifluoromethyl-1,2-dihydroindol-3(Z)-ylidene)ethyl)hydrazide (Compound 151)

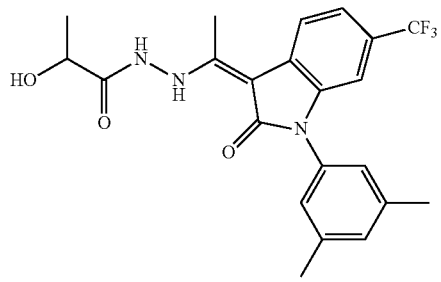 [SMILES: C/C(NNC(=O)C(C)O)=C1/C(=O)N(c2cc(C)cc(C)c2)c2cc(C(F)(F)F)ccc21]

Compound 151 was prepared according to the procedure described in Scheme I from 1-(3,5-dimethylphenyl)-6-trifluoromethyl-1,2-dihydroindol-2-one, triethyl orthoacetate, and 2-hydroxypropionic acid hydrazide. MW=433, LC-MS (M+1)=433.94.

Example 52

2-Hydroxyacetic Acid N'-(1-(1-(3,5-dimethylphenyl)-2-oxo-6-trifluoromethyl-1,2-dihydroindol-3(Z)-ylidene)ethyl)hydrazide (Compound 152)

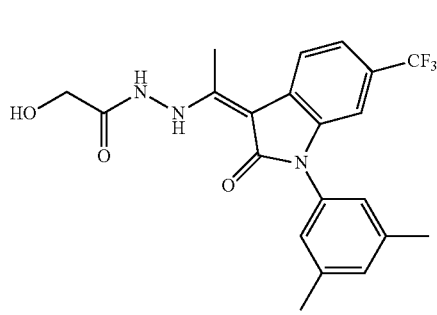 [SMILES: C/C(NNC(=O)CO)=C1/C(=O)N(c2cc(C)cc(C)c2)c2cc(C(F)(F)F)ccc21]

Compound 152 was prepared according to the procedure described in Scheme I from 1-(3,5-dimethylphenyl)-6-trifluoromethyl-1,2-dihydroindol-2-one, triethyl orthoacetate, and 2-hydroxyacetic acid hydrazide. MW=419, LC-MS (M+1)=419.97.

Example 53

3-Ethoxy-3-oxopropionic Acid N'-(1-(1-(3,5-dimethylphenyl)-2-oxo-6-trifluoromethyl-1,2-dihydroindol-3(Z)-ylidene)ethyl)hydrazide (Compound 153)

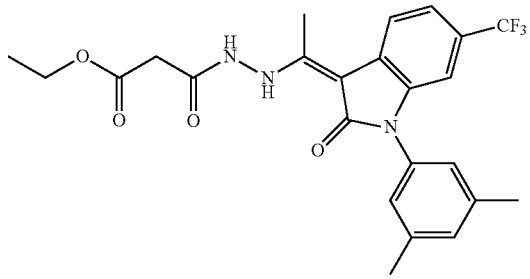 [SMILES: CCOC(=O)CC(=O)NN/C(C)=C1\C(=O)N(c2cc(C)cc(C)c2)c2cc(C(F)(F)F)ccc21]

Compound 153 was prepared according to the procedure described in Scheme I from 1-(3,5-dimethylphenyl)-6-trifluoromethyl-1,2-dihydroindol-2-one, triethyl orthoacetate, and 3-ethoxy-3-oxopropionic acid hydrazide. MW=475, LC-MS (M+1)=475.91.

Example 54

Aminocarboxylic Acid N'-(1-(1-(3,5-dimethylphenyl)-2-oxo-6-trifluoromethyl-1,2-dihydroindol-3(Z)-ylidene)ethyl)hydrazide (Compound 154)

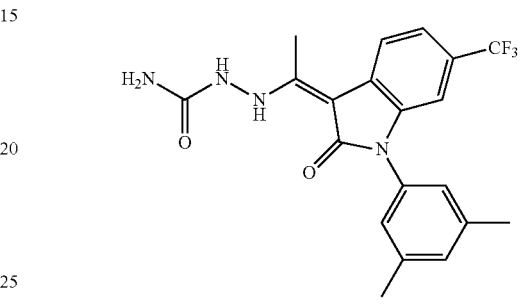

Compound 154 was prepared according to the procedure described in Scheme I from 1-(3,5-dimethylphenyl)-6-trifluoromethyl-1,2-dihydroindol-2-one, triethyl orthoacetate, and 1-aminocarboxylic acid hydrazide. MW=404, LC-MS (M+1)=404.93.

Example 55

Acetic Acid N'-(1-(1-(3,5-dimethylphenyl)-2-oxo-6-phenyl-1,2-dihydroindol-3(Z)-ylidene)ethyl)hydrazide (Compound 155)

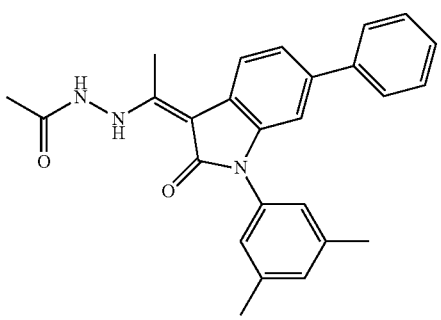 [SMILES: CC(=O)NN/C(C)=C1\C(=O)N(c2cc(C)cc(C)c2)c2cc(-c3ccccc3)ccc21]

Compound 155 was prepared according to the procedure described in Scheme I from 1-(3,5-dimethylphenyl)-6-phenyl-1,2-dihydroindol-2-one, triethyl orthoacetate, and acetic acid hydrazide.

Example 56

2-(4-Hydroxyphenyl)acetic Acid N'-(1-(1-(3,5-dimethylphenyl)-2-oxo-6-trifluoromethyl-1,2-dihydroindol-3(Z)-ylidene)ethyl)hydrazide (Compound 156)

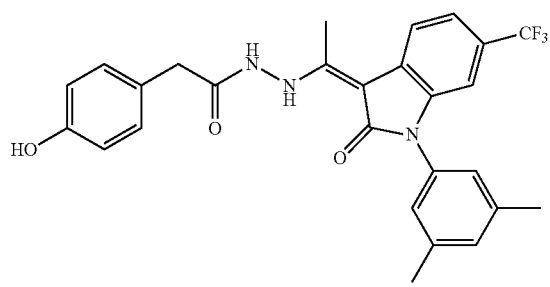 [SMILES: C/C(NNC(=O)Cc1ccc(O)cc1)=C1/C(=O)N(c2cc(C)cc(C)c2)c2cc(C(F)(F)F)ccc21]

Compound 156 was prepared according to the procedure described in Scheme I from 1-(3,5-dimethylphenyl)-6-trifluoromethyl-1,2-dihydroindol-2-one, triethyl orthoacetate, and 4-hydroxyphenylacetic acid hydrazide. $^1$H NMR (400 MHz, DMSO-$d_6$) 11.55 (s, 1H), 10.69 (s, 1H), 9.30 (s, 1H), 7.64 (d, J=8.0, 1H), 7.33 (d, J=8.0, 5H), 7.13 (s, 1H), 7.11 (s, 1H), 7.02 (s, 2H), 6.88 (s, 1H), 6.72 (d, J=8.0, 2H), 3.45 (s, 2H), 2.44 (s, 3H), 2.34 (s, 6H).

Example 57

Propionic Acid N'-(1-(1-(3,5-dimethylphenyl)-2-oxo-6-trifluoromethyl-1,2-dihydroindol-3(Z)-ylidene)ethyl)hydrazide (Compound 157)

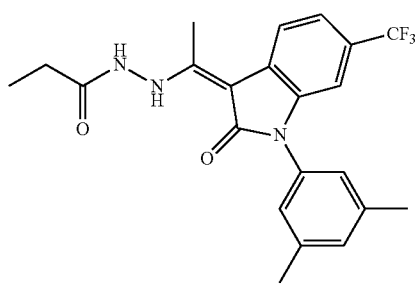 [SMILES: CCC(=O)NN/C(C)=C1\C(=O)N(c2cc(C)cc(C)c2)c2cc(C(F)(F)F)ccc21]

Compound 157 was prepared according to the procedure described in Scheme I from 1-(3,5-dimethylphenyl)-6-trifluoromethyl-1,2-dihydroindol-2-one, triethyl orthoacetate, and propionic acid hydrazide. $^1$H NMR (400 MHz, DMSO-$d_6$) 11.50 (s, 1H), 10.49 (s, 1H), 7.68 (d, J=8.0, 1H), 7.36 (d, J=8.0, 3H), 7.13 (s, 1H), 7.04 (s, 2H), 6.89 (s, 1H), 2.45 (s, 3H), 2.34 (s, 6H), 2.25 (dd, J=5.0 and 8.0, 2H), 1.10 (dd, J=5.0 and 8.0, 3H).

Example 58

Acetic Acid N'-(1-(1-(3,5-dimethylphenyl)-2-oxo-6-trifluoromethyl-1,2-dihydroindol-3(Z)-ylidene)ethyl)hydrazide (Compound 158)

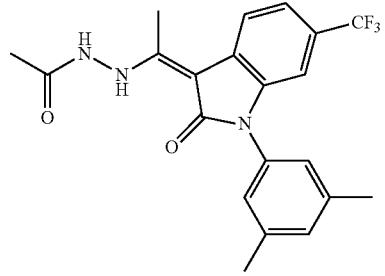 [SMILES: CC(=O)NN/C(C)=C1\C(=O)N(c2cc(C)cc(C)c2)c2cc(C(F)(F)F)ccc21]

Compound 158 was prepared according to the procedure described in Scheme I from 1-(3,5-dimethylphenyl)-6-trifluoromethyl-1,2-dihydroindol-2-one, triethyl orthoacetate, and acetic acid hydrazide. $^1$H NMR (400 MHz, DMSO-$d_6$) 11.50 (s, 1H), 10.51 (s, 1H), 7.68 (d, J=8.0, 1H), 7.38 (d, J=8.0, 3H), 7.12 (s, 1H), 7.04 (s, 2H), 6.89 (s, 1H), 2.44 (s, 3H), 2.34 (s, 6H), 1.99 (s, 3H).

Example 59

Ureidoacetic Acid N'-(1-(1-(3,5-dimethylphenyl)-2-oxo-6-trifluoromethyl-1,2-dihydroindol-3(Z)-ylidene)-1-phenylmethyl)hydrazide (Compound 159)

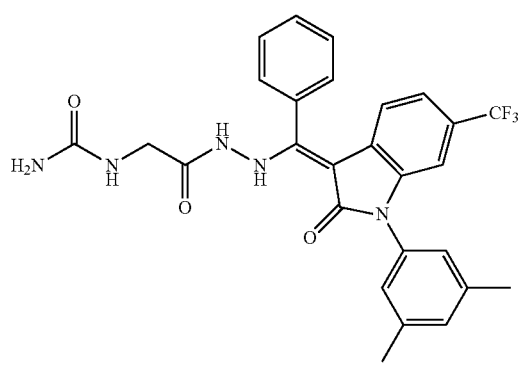 [SMILES: Cc1cc(C)cc(N2C(=O)/C(=C(\NNC(=O)CNC(N)=O)c3ccccc3)c3ccc(C(F)(F)F)cc32)c1]

Compound 159 was prepared according to the procedure described in Scheme I from 1-(3,5-dimethylphenyl)-6-trifluoromethyl-1,2-dihydroindol-2-one, triethyl orthobenzoate, and 2-(aminoacetylamino)acetic acid hydrazide. MW=523, LC-MS (M+1)=523.97.

Example 60

1-(2-Cyanoethyl)-3-methyl-5-oxo-4,5-dihydro-4-(2-hydroxy-3-(2-(2,6-dimethylphenyl)-ethyl)phenylhydrazono)pyrazole (Compound 160)

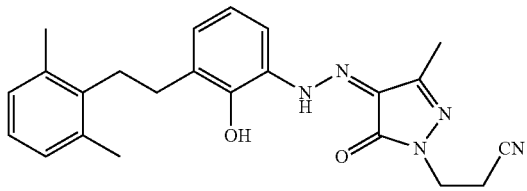 [SMILES: CC1=NN(CCC#N)C(=O)/C1=N\Nc1cccc(CCc2c(C)cccc2C)c1O]

Compound 160 was prepared according to the procedure described in Scheme II from 2-hydroxy-3-(2-(2,6-dimethylphenyl)ethyl)aniline, ethyl acetoacetate, and 2-cyanoethylhydrazine.

Example 61

1-(3-Hydroxypropyl)-3-methyl-5-oxo-4,5-dihydro-4-(2-hydroxy-3-(2-(2,6-dimethylphenyl)-ethyl)phenylhydrazono)pyrazole (Compound 161)

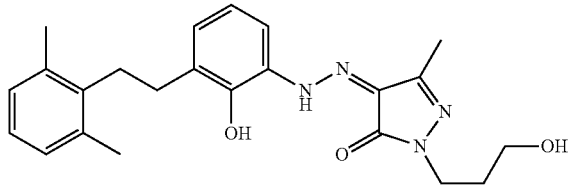 [SMILES: CC1=NN(CCCO)C(=O)/C1=N\Nc1cccc(CCc2c(C)cccc2C)c1O]

Compound 161 was prepared according to the procedure described in Scheme II from 2-hydroxy-3-(2-(2,6-dimethylphenyl)ethyl)aniline, ethyl acetoacetate, and 3-hydroxypropyl-1-hydrazine.

Example 62

1-(2-Hydroxyethyl)-3-methyl-5-oxo-4,5-dihydro-4-(2-hydroxy-3-(2-(2,5-dimethylphenyl)-ethyl)phenylhydrazono)pyrazole (Compound 162)

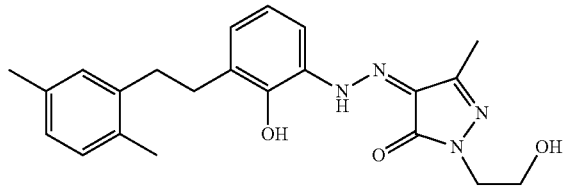 [SMILES: CC1=NN(CCO)C(=O)/C1=N\Nc1cccc(CCc2cc(C)ccc2C)c1O]

Compound 162 was prepared according to the procedure described in Scheme II from 2-hydroxy-3-(2-(2,5-dimethylphenyl)ethyl)aniline, ethyl acetoacetate, and 2-hydroxyethyl-1-hydrazine.

Example 63

1-(4-Hydroxybutyl)-3-methyl-5-oxo-4,5-dihydro-4-(2-hydroxy-3-(2(E)-(2-methylphenyl)-ethenyl)phenylhydrazono)pyrazole (Compound 163)

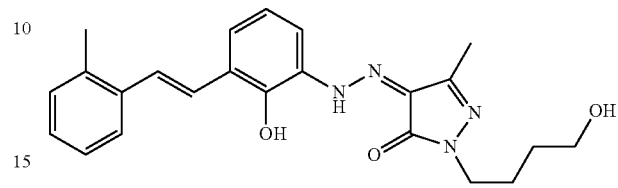

Compound 163 was prepared according to the procedure described in Scheme II from 2-hydroxy-3-(2(E)-(2-methylphenyl)ethenyl)aniline, ethyl acetoacetate, and 4-hydroxybutylhydrazine. MW=406, LC-MS (M+1)=407.02.

Example 64

1-(3-Hydroxypropyl)-3-methyl-5-oxo-4,5-dihydro-4-(2-hydroxy-3-(2-(2,5-dimethylphenyl)-ethyl)phenylhydrazono)pyrazole (Compound 164)

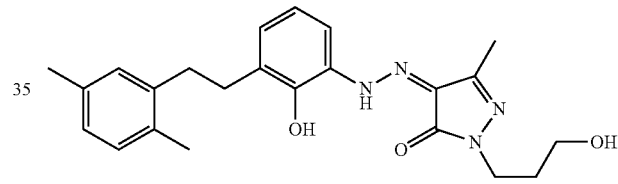

Compound 164 was prepared according to the procedure described in Scheme II from 2-hydroxy-3-(2-(2,5-dimethylphenyl)ethyl)aniline, ethyl acetoacetate, and 3-hydroxypropyl-1-hydrazine.

Example 65

1-(4-Hydroxybutyl)-3-methyl-5-oxo-4,5-dihydro-4-(2-hydroxy-3-(2-(2,6-dimethylphenyl)-ethynyl)phenylhydrazono)pyrazole (Compound 165)

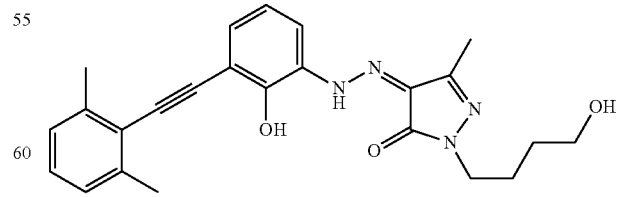

Compound 165 was prepared according to the procedure described in Scheme II from 2-hydroxy-3-(2-(2,6-dimethylphenyl)ethynyl)aniline, ethyl acetoacetate, and 4-hydroxybutyl-1-hydrazine.

Example 66

1-(2-Cyanoethyl)-3-methyl-5-oxo-4,5-dihydro-4-(2-hydroxy-3-(2-(2,5-dimethylphenyl)-ethyl)phenylhydrazono)pyrazole (Compound 166)

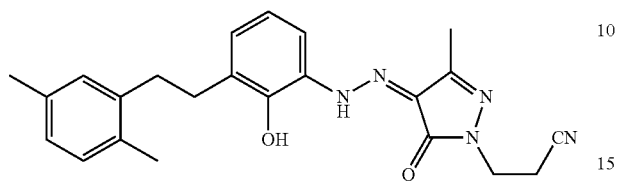

Compound 166 was prepared according to the procedure described in Scheme II from 2-hydroxy-3-(2-(2,5-dimethylphenyl)ethyl)aniline, ethyl acetoacetate, and 2-cyanoethyl-1-hydrazine.

Example 67

1-(4-Hydroxybutyl)-3-methyl-5-oxo-4,5-dihydro-4-(2-hydroxy-3-(2-(2-methylphenyl)-ethyl)phenylhydrazono)pyrazole (Compound 167)

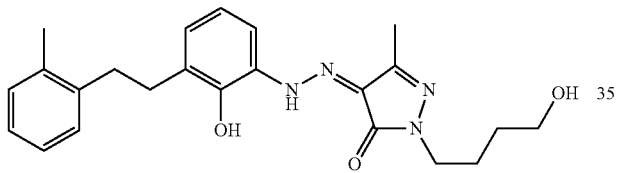

Compound 167 was prepared according to the procedure described in Scheme II from 2-hydroxy-3-(2-(2-methylphenyl)ethyl)aniline, ethyl acetoacetate, and 4-hydroxybutyl-1-hydrazine.

Example 68

1-Benzyl-3-methyl-5-oxo-4,5-dihydro-4-(2-hydroxy-3-(2-(2,6-dimethylphenyl)-ethyl)phenylhydrazono)pyrazole (Compound 168)

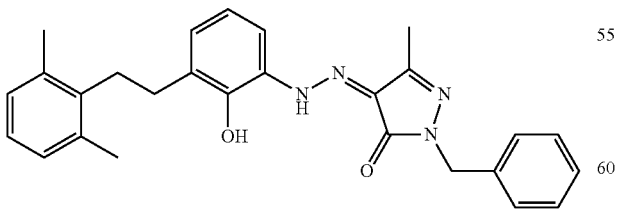

Compound 168 was prepared according to the procedure described in Scheme II from 2-hydroxy-3-(2-(2,6-dimethylphenyl)ethyl)aniline, ethyl acetoacetate, and benzylhydrazine.

Example 69

1-(3,5-Dimethylphenyl)-2-oxo-2,3-dihydro-3-(2-hydroxy-4-hydroxymethylphenylhydrazono)-6-trifluoromethylindole (Compound 169)

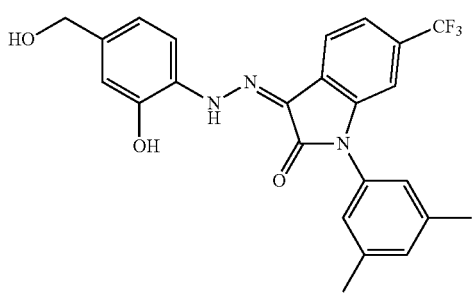 [SMILES: Cc1cc(C)cc(N2C(=O)/C(=N\Nc3ccc(CO)cc3O)c3ccc(C(F)(F)F)cc32)c1]

Compound 169 was prepared according to the procedure similar as described in Scheme II from 2-hydroxy-4-hydroxymethylaniline and 1-(3,5-dimethylphenyl)-6-trifluoromethyl-1,2-dihydroindol-2-one.

Example 70

1-(3,5-Dimethylphenyl)-2-oxo-2,3-dihydro-3-(2-hydroxy-3-hydroxymethylphenylhydrazono)-6-trifluoromethylindole (Compound 170)

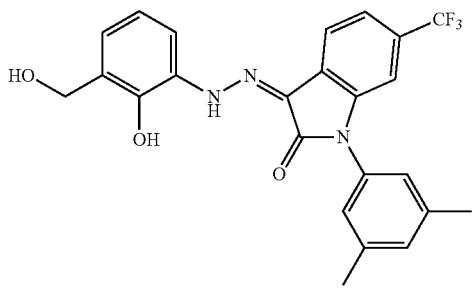 [SMILES: Cc1cc(C)cc(N2C(=O)/C(=N\Nc3cccc(CO)c3O)c3ccc(C(F)(F)F)cc32)c1]

Compound 170 was prepared according to the procedure similar as described in Scheme II from 2-hydroxy-3-hydroxymethylaniline and 1-(3,5-dimethylphenyl)-6-trifluoromethyl-1,2-dihydroindol-2-one.

Example 71

4-(4,5-Dihydro-4-(1-hydroxy-2-naphthylhydrazono)-3-methy-5-oxo-pyrazole)benzoic Acid (Compound 171)

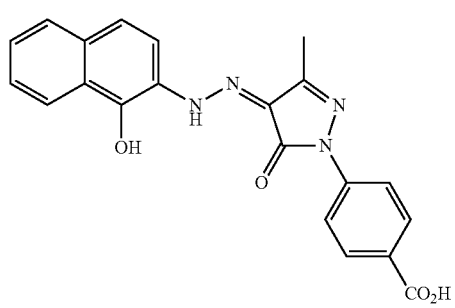 [SMILES: CC1=NN(c2ccc(C(=O)O)cc2)C(=O)/C1=N\Nc1ccc2ccccc2c1O]

Compound 171 was prepared according to the procedure described in Scheme II from 1-hydroxy-2-aminonaphthalene, ethyl acetoacetate, and 4-hydroxycarbonylphenylhydrazine.

Example 72

4,5-Dihydro-1-(4-hydroxymethylphenyl)-4-(1-hydroxy-2-naphthylhydrazono)-3-methypyrazol-5-one (Compound 172)

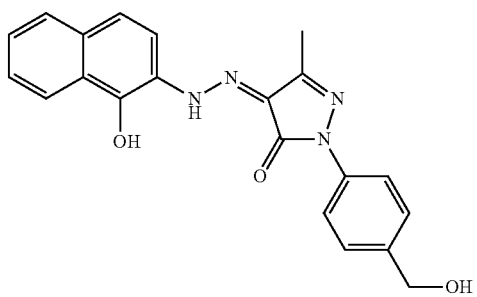 [SMILES: CC1=NN(c2ccc(CO)cc2)C(=O)/C1=N\Nc1ccc2ccccc2c1O]

Compound 172 was prepared according to the procedure described in Scheme II from 1-hydroxy-2-aminonaphthalene, ethyl acetoacetate, and 4-hydroxymethylphenylhydrazine.

Example 73

4,5-Dihydro-1-(4-(2-cyanoethyl)phenyl)-4-(1-hydroxy-2-naphthylhydrazono)-3-methypyrazol-5-one (Compound 173)

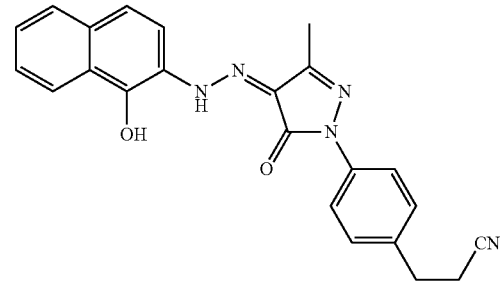 [SMILES: CC1=NN(c2ccc(CCC#N)cc2)C(=O)/C1=N\Nc1ccc2ccccc2c1O]

Compound 173 was prepared according to the procedure described in Scheme II from 1-hydroxy-2-aminonaphthalene, ethyl acetoacetate, and 4-(2-cyanoethyl)phenylhydrazine.

Example 74

4-Hydroxybutyric Acid N'-(1-(5-chloro-1-phenyl-2-oxo-1,2-dihydroindol-3(Z)-ylidene)ethyl)hydrazide (Compound 174)

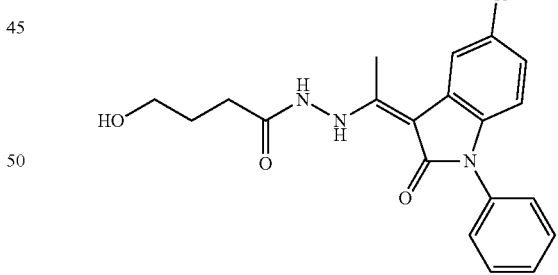

Compound 174 was prepared according to the procedure described in Scheme I from 1-phenyl-5-chloro-1,2-dihydroindol-2-one, triethyl orthoacetate, and 4-hydroxybutyric acid hydrazide.

Example 75

Methyl 2-(1-(1-(3,5-dimethylphenyl)-2-oxo-6-trifluoromethyl-1,2-dihydroindol-3(Z)-ylidene)ethyl)aminoacetate (Compound 175)

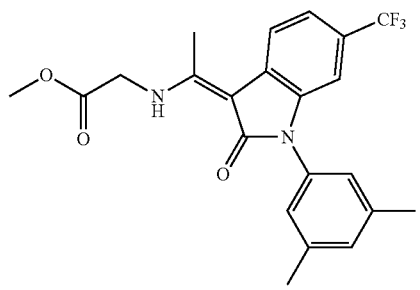

Compound 175 was prepared according to the procedure described in Scheme I from 1-(3,5-dimethylphenyl)-6-trifluoromethyl-1,2-dihydroindol-2-one, triethyl orthoacetate, and methyl aminoacetate. MW=418, LC-MS (M+1)=418.96.

Example 76

Acetic Acid N'-(1-(1-(3,5-dimethylphenyl)-5-oxo-3-methyl-4,5-dihydropyrazol-4(Z)-ylidene)ethyl)hydrazide (Compound 176)

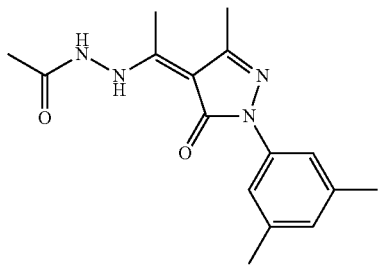 [SMILES: CC(=O)NN/C(C)=C1\C(=O)N(c2cc(C)cc(C)c2)N=C1C]

Compound 176 was prepared according to the procedure similar as described in Scheme I from 1-(3,5-dimethylphenyl)-3-methylpyrazol-5-one, triethyl orthoacetate, and acetic acid hydrazide.

Example 77—Certain Assays

In certain embodiments, assays may be used to determine the level of GCSFR modulating activity of the compounds of the present embodiments. In certain embodiments, assays containing selectively mutated GCSFR may be used to determine the interaction of the compounds with the TM domain. In certain embodiments, assays containing GCSFR from species different than human may be used to measure the activity of the compounds (e.g. mouse or monkey).

Cell Proliferation Assay

In some embodiments, compounds are tested in an in vitro proliferation assay using the cell lines that express GCSFR either endogenously or by stable or transient transfection, and may be dependant upon GCSF for their growth. Activity of the compounds on cell proliferation is determined by counting the cells or by use of an assay that measures the production of ATP as a marker of cell growth.

Reporter Assay

In some embodiments, compounds are tested in a reporter assay using the cell lines that express GCSFR endogenously or by stable or transient transfection. These cells are transfected, stably or transiently, with the GCSF-responsive reporter (such as luciferase) and the activity of the compounds is determined by measuring the amount of reporter in the cell.

Differentiation Assay

In some embodiments, compounds are tested in purified human CD34+ bone marrow cells. After addition of the compounds to the cells, the number of cells expressing markers of hematopoiesis, erythropoiesis, granulopoiesis, thrombopoiesis, or myelopoiesis is measured by flow cytometry, by analyzing expression of genes associated with these pathways, or by measuring the formation of colonies of cells specific for these pathways (e.g. erythrocytes or granulocytes). In some embodiments, compounds are tested in bone marrow cells from other species besides human (e.g. mouse or monkey).

Example 78—Luciferase Reporter Assays

Human GCSF Receptor (hGCSFR) Assay

A luciferase reporter assay was used to identify compounds that activate hGCSFR. A human cell line (e.g. MCF-7 breast cancer cells, HepG2 hepatoma cells or HEK293 kidney cells) was transiently transfected with an hGCSFR expression plasmid, containing the hGCSFR cDNA downstream of the CMV promoter, and a luciferase reporter plasmid, containing a GCSF-responsive element upstream of a minimal thymidine kinase promoter. For the luciferase reporter assay, cells were plated into 96-well microtiter plates in Eagle's Minimal Essential Media (EMEM) containing 10% fetal bovine serum (FBS). The following day, the hGCSFR expression plasmid and the luciferase reporter plasmid were transiently transfected into the cells using FuGene6 transfection reagent (Roche, Indianapolis, Ind.), according to manufacturer's specifications. The next day, the media was replaced with media containing 1% FBS and 10 µM zinc chloride. On the fourth day, media containing recombinant hGCSF (rhGCSF) (at a maximal concentration of 200 ng/ml) or test compound (at a maximal concentration of 10 µM) were added to the cells in duplicate. After six hours, the medium was removed from the cells, and the cells were lysed with a detergent-containing buffer. Luciferase activity was measured in cell extracts to determine the level of transcriptional activation. Luciferin-containing buffer was added to each well of the 96-well plate and luciferase activity was measured using a luminometer.

Mutant hGCSFR or Mouse GCSFR (mGCSFR) Assays

A luciferase reporter assay was used to determine the ability of compounds to activate mutated hGCSFR, mGCSFR, or mutated mGCSFR. A human cell line (e.g. MCF-7 breast cancer cells, HepG2 hepatoma cells or HEK293 kidney cells) was transiently transfected with one of three GCSFR expression plasmids: 1) an hGCSFR expression plasmid containing the hGCSFR cDNA in which the nucleotides coding for histidine-627 in the hGCSFR TM domain were changed to code for asparagine that exists as asparagine-602 of the mouse GCSFR TM in a similar position of histidine-627; 2) a mGCSFR expression plasmid, containing the mGCSFR cDNA downstream of the CMV promoter; 3) a mGCSFR expression plasmid containing the mGCSFR cDNA in which the nucleotides coding for asparagine-602 in the mGCSFR TM domain were changed to code for hisitidine. For the luciferase reporter assay, cells were plated into 96-well microtiter plates in Eagle's Minimal Essential Media (EMEM) containing 10% fetal bovine serum (FBS). The following day, one of the three GCSFR expression plasmids and the luciferase reporter plasmid were transiently transfected into the cells using FuGene6 transfection reagent (Roche, Indianapolis, Ind.), according to manufacturer's specifications. The next day, the media was replaced with media containing 1% FBS and 10 M zinc chloride. On the fourth day, media containing rhGCSF (at a maximal concentration of 200 ng/ml) or test compound (at a maximal concentration of 10 M) were added to the cells in duplicate. After six hours, the medium was removed from the cells, and the cells were lysed with a detergent-containing buffer. Luciferase activity was measured in cell extracts to determine the level of transcriptional activation. Luciferin-containing buffer was added to each well of the 96-well plate and luciferase activity was measured using a luminometer.

Example 79—Cell Proliferation Assay

A proliferation assay, using the ViaLight™ Plus kit (Cambrex) or the ATPlite kit (Roche), has been used to establish the activity of compounds on the growth of the cells. The UT-7 human leukemia cell line (Komatsu N, Nakauchi H, Miwa A, Ishihara T, Eguchi M, Moroi M, Okada M, Sat0 Y, Wada H, Yawata Y, Suda T, Miura Y: Establishment and characterization of a human leukemic cell line with megakaryocytic features: Dependency on granulocyte-macrophage colony-stimulating factor, interleukin 3, or erythropoietin for growth and survival. Cancer Res 51:341, 1991) was stably transfected with an hGCSFR expression plasmid. Stable clones expressing the hGCSFR (UT7-hPG cells) were identified and grown and maintained in media containing 10% FBS, rhGM-CSF and G418. For the assay, UT7-hPG cells were starved of rhGM-CSF overnight, and plated in 96-well plates in media containing 10% FBS and 10 μM zinc. Media containing rhGCSF (at a maximal concentration of 200 ng/ml) or test compound (at a maximal concentration of 10 μM) were added to the cells in duplicate. After 48 hours, the proliferation of the cells was measured using the ViaLight™ Plus kit according to the manufacturer's protocol. The cells were lysed with a detergent-containing buffer for 10 minutes, and then the ATP monitoring reagent was added to generate luminescent signal. The signal was measured as relative light units in cell extracts to determine the level of proliferation of the cells.

Example 80—[$^{125}$I]-rhGCSF Competitive Binding Assay

A competitive binding assay was used to determine the activity of compounds on the binding of recombinant human GCSF (rhGCSF) to the hGCSFR. For the assay, UT7-hPG cells were starved of rhGM-CSF for 4 hours in media containing 2% FBS, and plated in 96-well v-bottom plates in media containing 2% FBS, 10 μM zinc and 0.1% sodium azide. Media containing rhGCSF (at a maximal concentration of 200 ng/ml) or test compound (at a maximal concentration of 10 μM) were added to the cells in duplicate. After 1 hour at room temperature, media containing [125I]-labeled rhGCSF (NEX-426, Perkin Elmer) to a final concentration of 0.05 nM was added to the cells, and the cells were incubated for 2 hours at room temperature on a rocking platform. The cells were washed twice with cold phosphate buffered saline, and the cells were lysed with a triton X-100 containing-buffer. The lysates were transferred to scintiallation vials, scintiallation fluid added, and the amount of radiation in the vials (count per minute) measured in a scintillation counter.

Example 81—Bone Marrow Cell Differentiation Assay

A human bone marrow granulocyte differentiation assay was used to determine the capacity of rhGCSF or test compounds to induce the differentiation of human bone marrow CD34$^+$ cells to CD15-positive (CD15$^+$) granulocytes. Purified normal human bone marrow CD34$^+$ cells from Cambrex were used in this assay. The cells were cultured with media containing 10% fetal bovine serum (FBS), 0.5 ng/mL stem cell factor (SCF) with or without 0.1 ng/ml rhGCSF for three days. Cells were washed and plated in 12-well plates in media containing 10% FBS and 0.5 ng/ml SCF. rhGCSF (at a maximal concentration of 100 ng/ml) and test compounds (at a maximal concentration of 1 μM) were added in triplicate, and cells were cultured an additional 7 days. The cells were stained with anti-CD15 antibody or isotype controls and analyzed by flow cytometry. The activity was measured as percent CD15$^+$ cells and presented as the percentage of maximal rhGCSF response. The EC$_{50}$ was determined from the dose-response curve of the compound, and efficacy was calculated by comparison with 100 ng/ml rhGCSF. In addition, the effect of rhGCSF or test compound on the growth of CD34$^+$ cells was measured using the ATPlite™ kit after 7 days of incubation with rhGCSF or compound.

Example 82—A Human GCSFR Agonist

GCSF is a cytokine that regulates neutrophilic granulocytes. GCSF acts on the homodimeric receptor (GCSFR) to stimulate proliferation of granulocytic progenitor cells and induce their survival and differentiation into neutrophils. Recombinant human GCSF (rhGCSF) is used successfully to alleviate severe chronic neutropenia and neutropenia induced by chemotherapy or associated with hematopoietic stem cell transplantation. A small molecule oral GCSFR agonist may offer a safer and more convenient alternative to the current injectable rhGCSF therapy. A series of novel non-peptidyl small molecules, exemplified by the lead Compound X, that selectively activate human GCSFR (hGCSFR) function, and may provide a significant innovation in the treatment of neutropenia have been discovered.

Methods

Luciferase Reporter Assays: HepG2 or HEK293 cells were transiently transfected with an expression vector for hGCSFR, hTPOR, hEPOR, mouse GCSFR or mutated receptors and either a STAT3-responsive or a STAT5-responsive luciferase reporter. Cells were treated with vehicle, rhGCSF (Neupogen®), rhTPO (R&D Systems), rhEPO (Epogen®) or Compound X for 6 hours prior to lysis and luciferase measurement.

Generation of hGCSFR Stable Cell Line UTP-hGCSFR: UT7 parental cells were transfected with an hGCSFR expression vector containing a neomycin resistance gene, and clones were identified by resistance to G418. A subclone (UTP-hGCSFR) responsive to hGCSF was identified.

Viability Assays: UT7-TPO, UT7-EPO or UTP-hGCSFR cells were treated with vehicle, rhGCSF, rhTPO, rhEPO or Compound X for 48 hours. Viability was assayed by ATP-light® (PerkinElmer).

Granulocyte Differentiation Assay: CD34-positive human bone marrow cells were cultured in media supplemented with human stem cell factor (hSCF, R&D Systems), and with vehicle, rhGCSF, or Compound X for 7 days. The cells were stained with anti-CD15 (BD Biosciences) and analyzed by FACS.

Detection of phospho-STAT3 and phospho-STAT5: Cells cultured with vehicle, rhGCSF or Compound X for various times and phospho-STAT3 and phospho-STAT5 were measured using AlphaScreen® SureFire® assay kits (PerkinElmer).

Radioligand-binding Experiments: UTP-hGCSFR cells were incubated with [125I]rhGCSF (PerkinElmer) in the presence or absence of rhGCSF or Compound X for 2 h at room temperature. Cells were washed twice and the amount of radioactivity measured in a scintillation counter.

Results

Figure 1B:
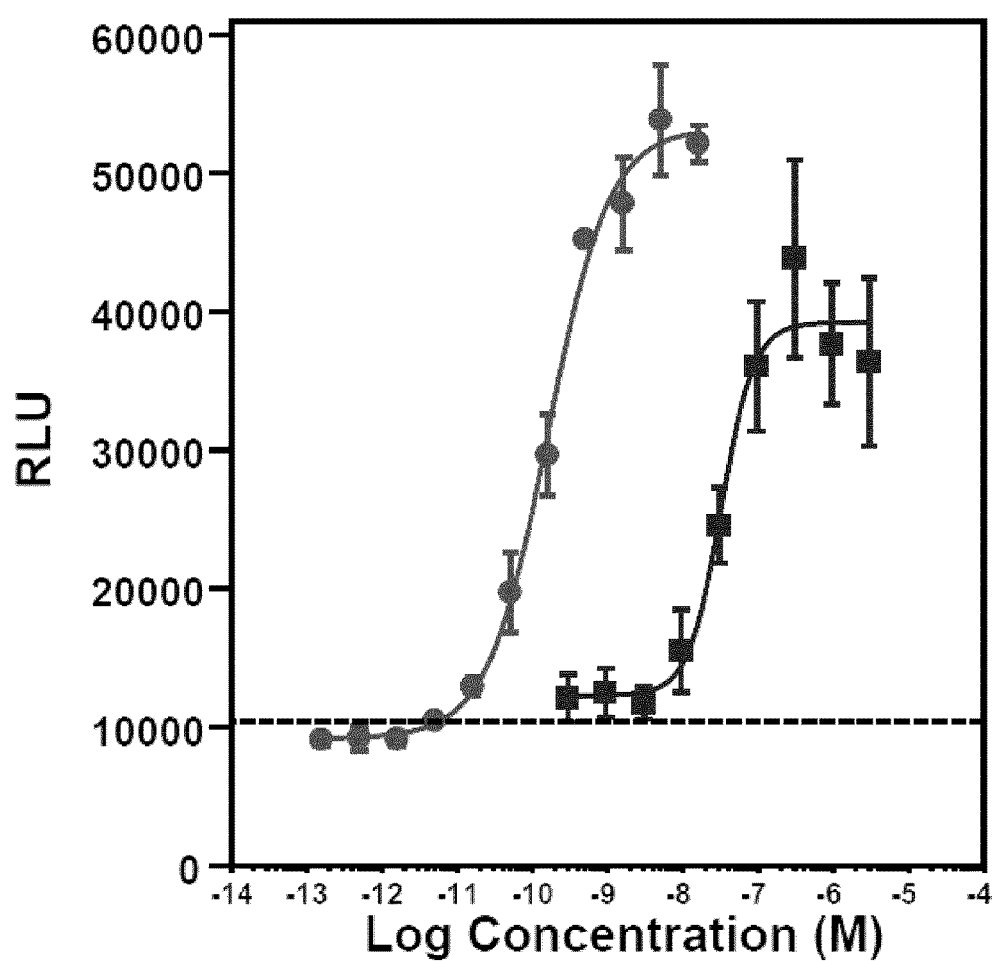
FIG. 1B is a graph of luciferase activity in HEK293 cells transfected with a STAT5-responsive reporter construct and treated with various concentrations of rhGCSF, Compound X, or control. Mean RLU (duplicates) ±SD.
Figure 2A:
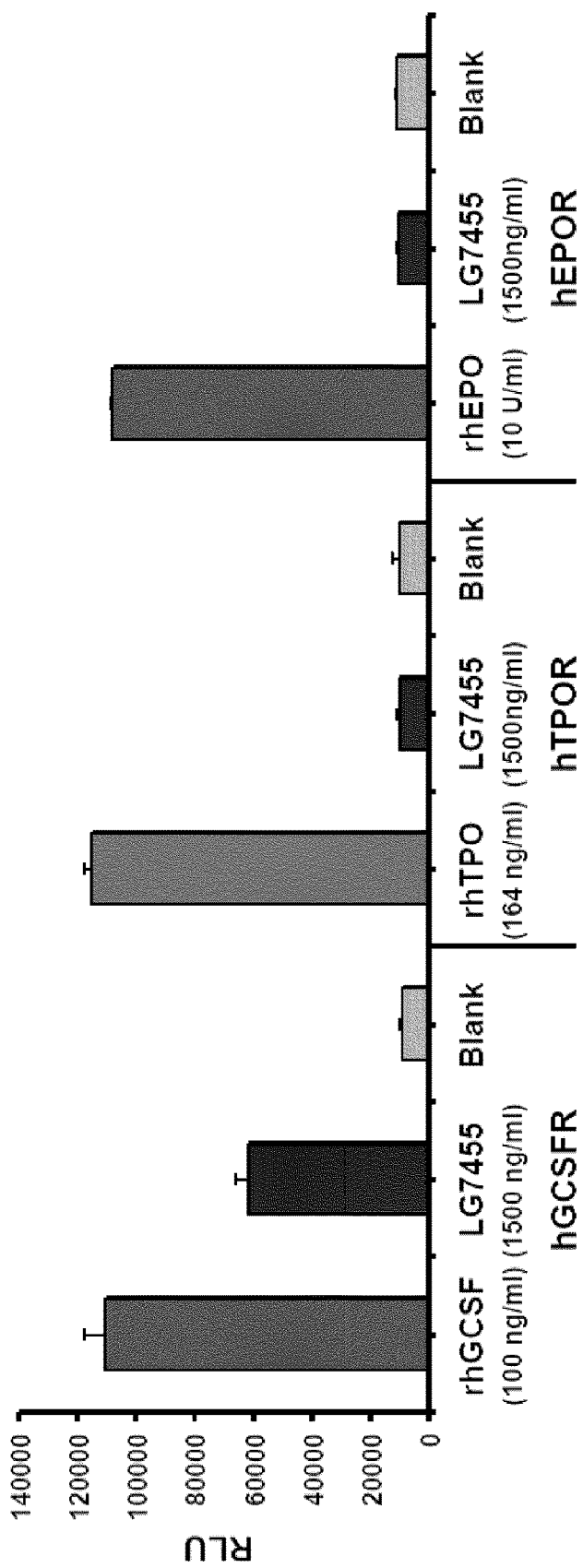
FIG. 2A and FIG. 2B are graphs of relative luciferase activity in HEK293 cells transfected with a STAT5-responsive reporter construct and a hGCSFR, hTPOR, or hEPOR expression vector, and treated with rhGCSF, Compound X, or control. Mean (triplicates)±SD
Figure 2B:
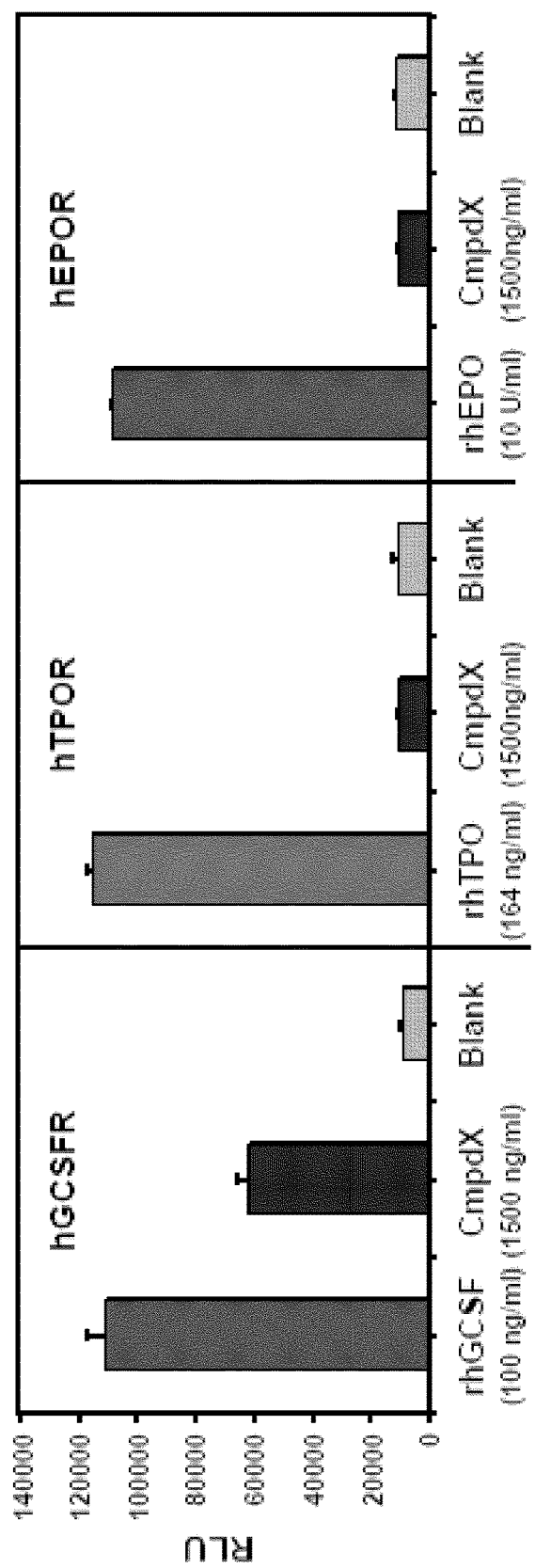

Compound X activated STAT3 and STAT5 responsive luciferase reporters in cells co-transfected with an hGCSFR expression vector (FIG. 1A and FIG. 1B). Compound X did not activate either reporter in the absence of transfected hGCSFR (not shown). Compound X did not activate a STAT5-responsive luciferase reporter in HEK293 cells transfected with hTPOR or hEPOR expression vectors (FIG. 2A and FIG. 2B).

Figure 3A:
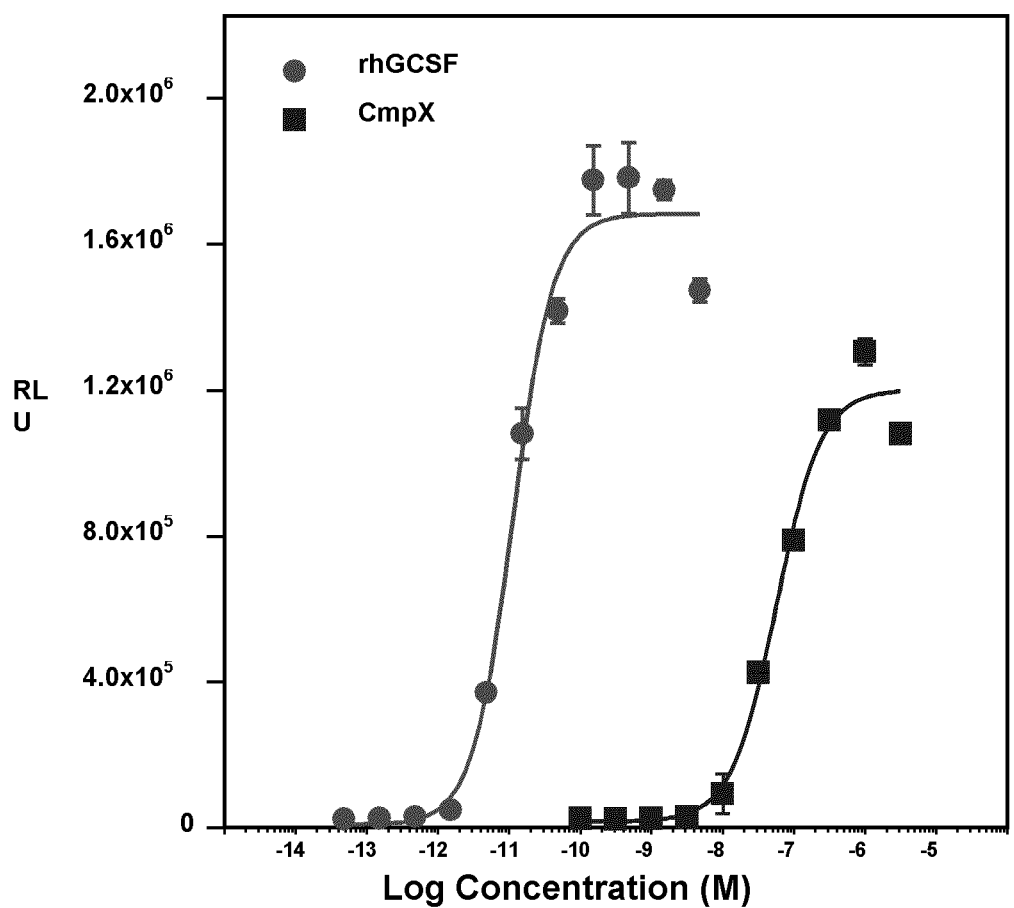
FIG. 3A is a graph of relative luciferase activity of viability of UTP-hGCSFR stable cells treated with rhGCSF or Compound X.
Figure 3B:
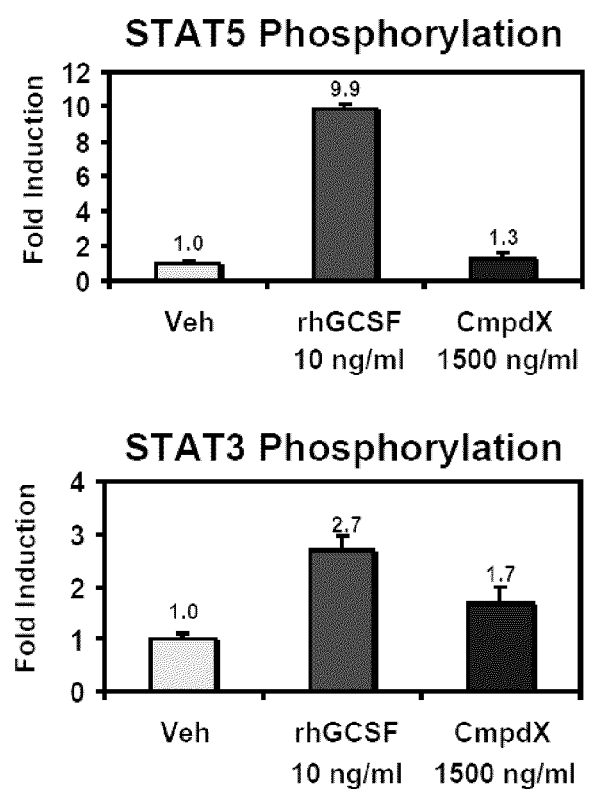
FIG. 3B and FIG. 3C depict graphs of fold induction of STAT5 phosphorylation (upper panel) or STAT3 phosphorylation (lower panel) in UTP-hGCSFR stable cells treated with rhGCSF or Compound X. Mean (duplicates)±SD.
Figure 3C:
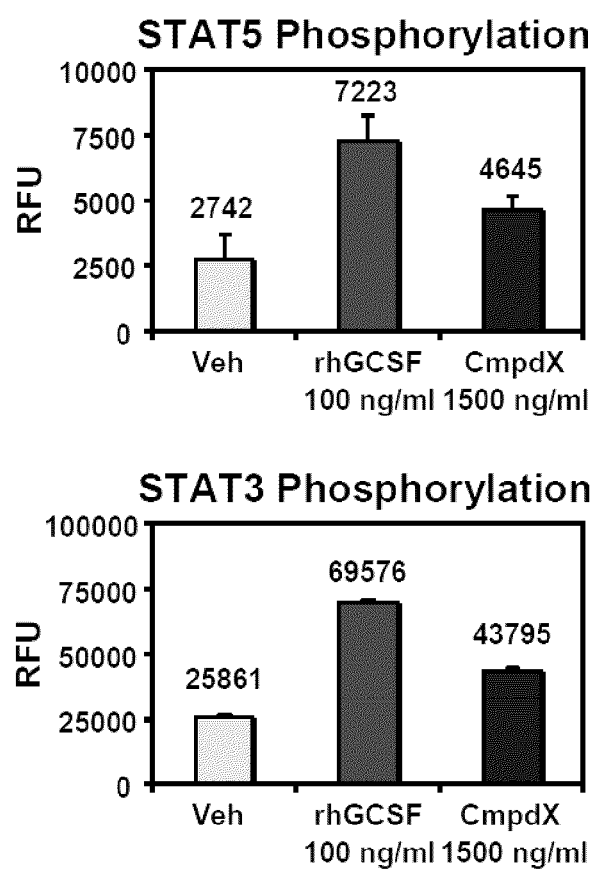

Compound X increased the viability of UTP-hGCSFR stable cells (FIG. 3) but did not increase growth of TPO- or EPO-responsive UT-7 cells (data not shown). Compound X increased the phosphorylation of STAT3 and STAT5 in UTP-hGCSFR stable cells (FIG. 3B and FIG. 3C).

Figure 4:
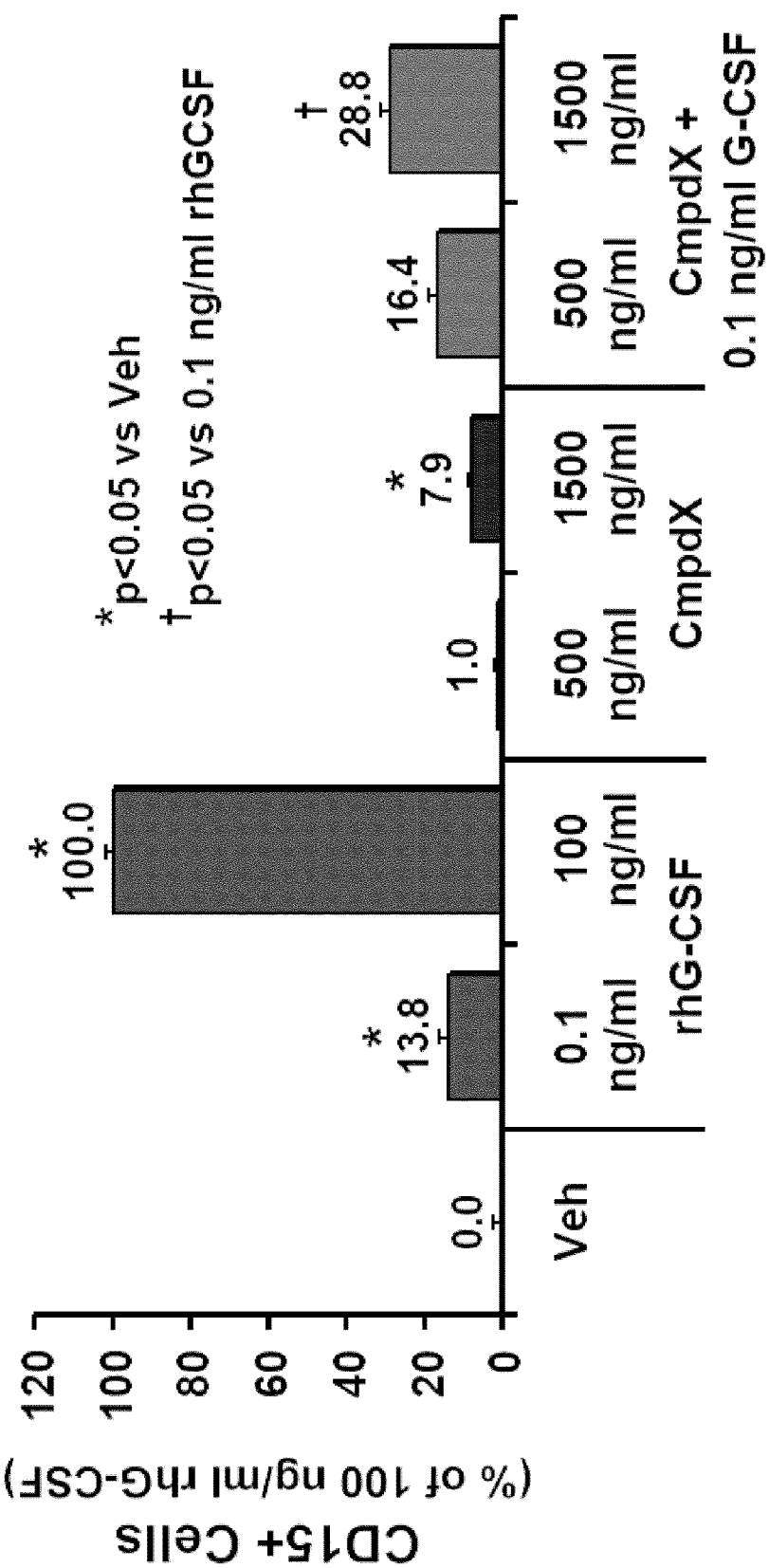
FIG. 4 is a graph showing the relative expression of CD15 in CD34+ human bone marrow cells treated with various concentrations of rhGCSF, Compound X, or rhGCSF and Compound X.

Compound X induces the expression of the granulocyte-specific marker CD15 (FUT4) in CD34-positive, human bone marrow cells (BM-HCs) (FIG. 4). Compound X was additive to the effect of 0.1 ng/ml rhGCSF, comparable to a normal serum concentration of GCSF.

The amino acid sequences of the transmembrane domain of GCSFR from various species were compared (FIG. 5). Compound X is active in cells expressing monkey, but not mouse, guinea pig or rabbit GCSFR (data not shown). SEQ ID NO.:01 is transmembrane domain of GCSFR from human; SEQ ID NO.:02 is transmembrane domain of GCSFR from monkey; SEQ ID NO.:03 is transmembrane domain of GCSFR from rabbit; SEQ ID NO.:04 is transmembrane domain of GCSFR from guinea pig; SEQ ID NO.:05 is transmembrane domain of GCSFR from mouse.

Figure 6A:
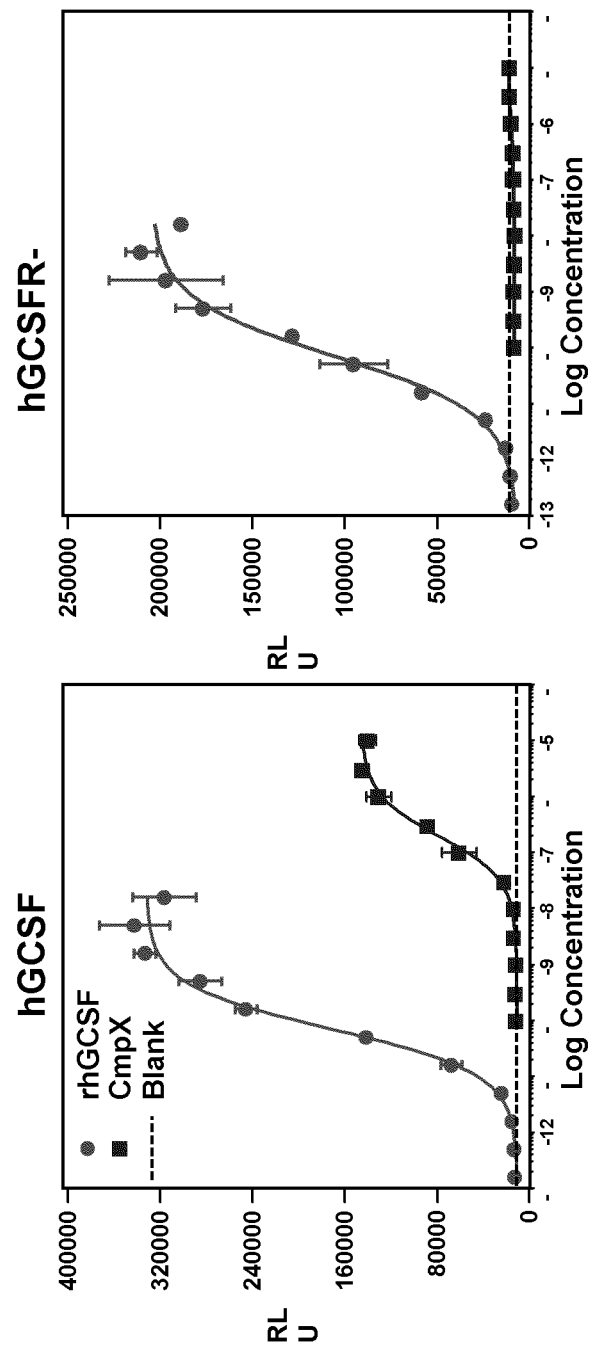
FIGS. 6A and 6B are graphs of relative STAT3-responsive luciferase reporter activity in cells treated with various concentrations of rhGCSF, Compound X, or control, and transfected with various expression vectors.
Figure 6B:
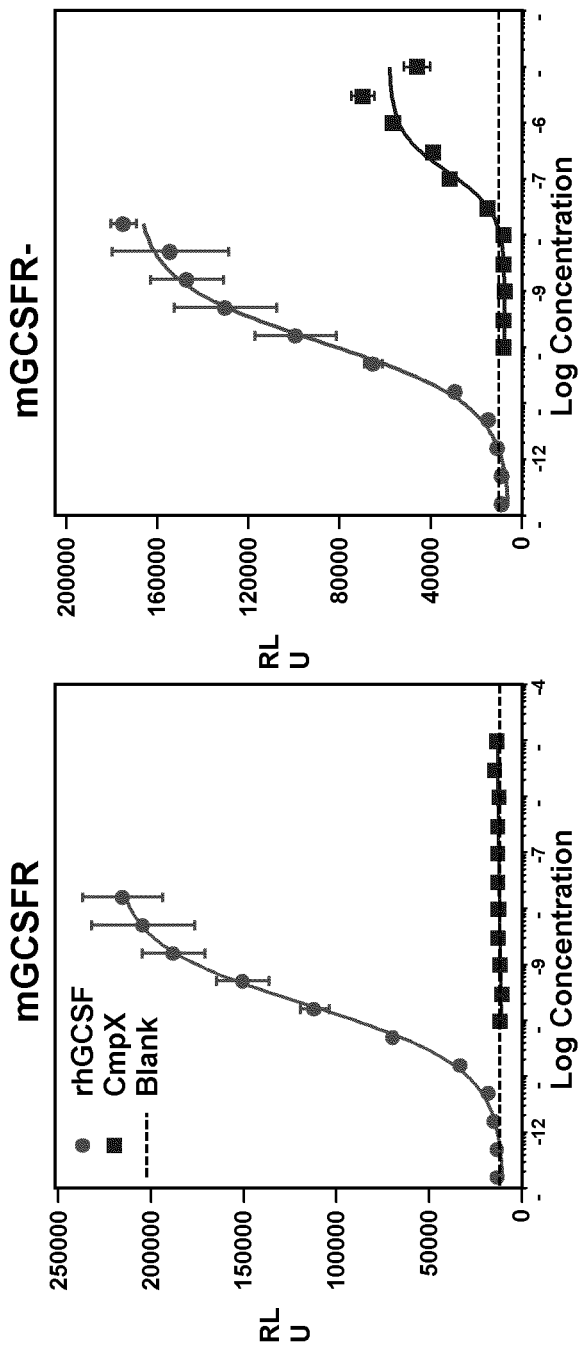
Figure 7:
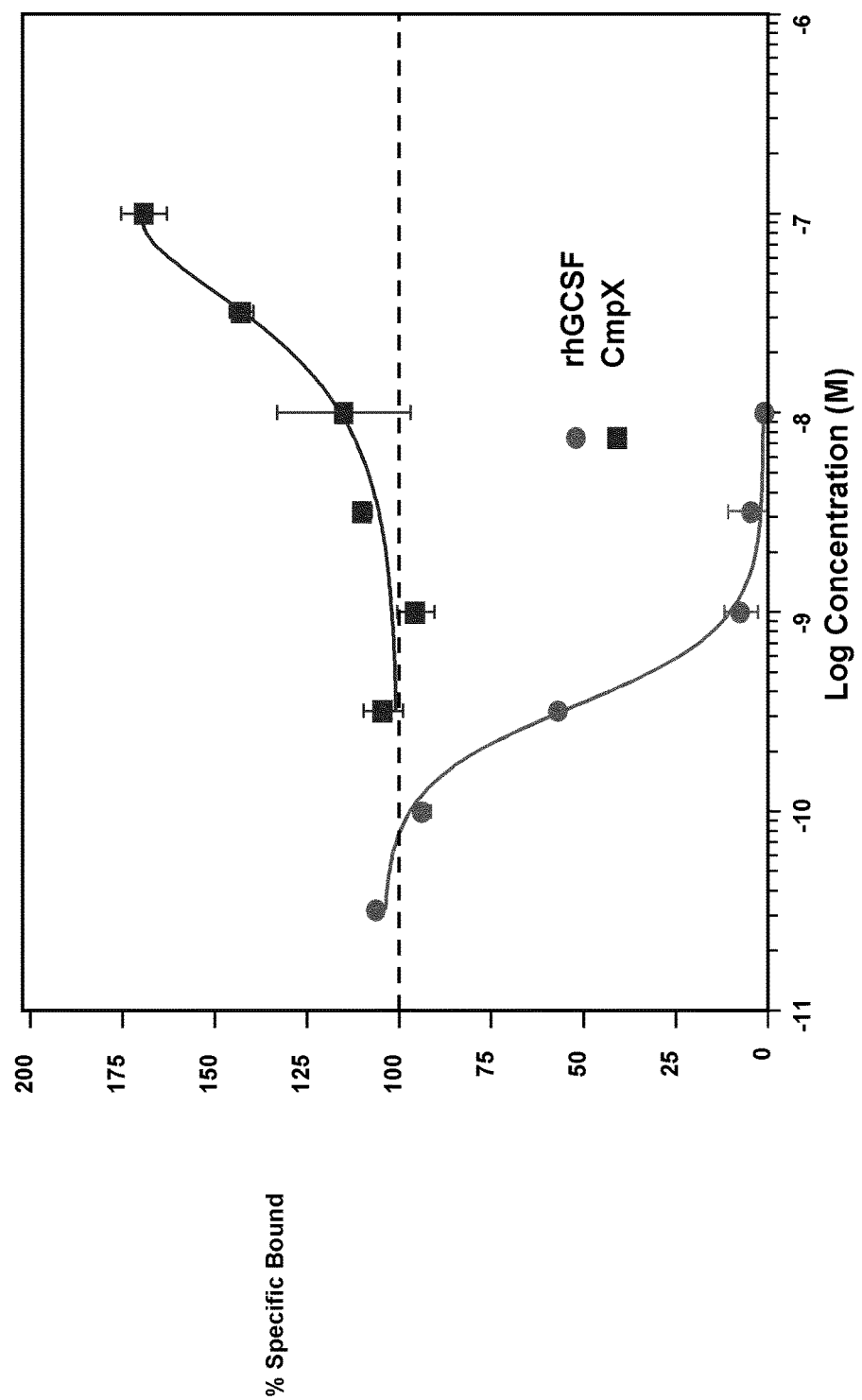
FIG. 7 is a graph showing allosteric binding of Compound X to hGCSFR in UTP-hGCSFR cells. Compound X did not displace [$^{125}$I]rhGCSF and binding of [$^{125}$I]rhGCSF was augmented in a concentration dependent manner.

Mutant receptors were created by replacing H627 in hGCSFR with N present at a similar location in the mouse GCSFR (N602), and by replacing N602 in the mouse GCSFR with H. Compound X is not active in cells expressing the mGCSFR or hGCSFR-H627N (FIG. 6A). Compound X is active, however, on mGCSFR-N602H (FIG. 6B). Mean (triplicates)±SD Compound X did not displace [125I]rhGCSF binding to UTP-hGCSFR cells, however binding of [125I]rhGCSF was augmented in a concentration-dependent manner (FIG. 7).

Discussion

A novel small molecule human GCSFR agonist that activates GCSFR function was discovered. Compound X was found to activate the GCSFR/JAK/STAT signal transduction pathway and increased the viability of cells containing hGCSFR. Compound X promoted the differentiation of bone marrow cells into granulocytes, increasing expression of CD15. Compound X is dependent on the expression of hGCSFR and a histidine in the receptor transmembrane domain was needed for activity, similar to what has been found for small-molecule human TPOR agonists. Compound X increased the binding of GCSF in a manner consistent with allosteric receptor modulation.

These data demonstrate that Compound X is a novel small-molecule selective hGCSFR agonist that activates the receptor in a manner distinct from GCSF and similar to the mechanism of small-molecule hTPOR agonists. Further optimization of the Compound X chemical series should yield a new generation of orally-available molecules to treat neutropenia with improved safety and convenience compared to current injectable rhGCSF.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

SEQUENCE LISTING

```
<160> NUMBER OF SEQ ID NOS: 5

<210> SEQ ID NO 1
<211> LENGTH: 31
<212> TYPE: PRT
<213> ORGANISM: homo sapiens
```

```
<400> SEQUENCE: 1

Glu Gly Ser Glu Leu His Ile Ile Leu Gly Leu Phe Gly Leu Leu Leu
1               5                   10                  15

Leu Leu Thr Cys Leu Cys Gly Thr Ala Trp Leu Cys Cys Ser Pro
            20                  25                  30

<210> SEQ ID NO 2
<211> LENGTH: 31
<212> TYPE: PRT
<213> ORGANISM: Monkey

<400> SEQUENCE: 2

Glu Gly Ser Glu Leu His Ile Leu Leu Gly Leu Phe Gly Leu Leu Leu
1               5                   10                  15

Leu Leu Thr Cys Leu Cys Gly Thr Ala Trp Leu Cys Cys Ser Pro
            20                  25                  30

<210> SEQ ID NO 3
<211> LENGTH: 31
<212> TYPE: PRT
<213> ORGANISM: Oryctolagus cuniculus

<400> SEQUENCE: 3

Glu Glu Ser Val Leu His Ile Ile Leu Gly Leu Ser Gly Ser Leu Phe
1               5                   10                  15

Leu Leu Leu Cys Leu Cys Gly Thr Thr Trp Leu Cys Cys Ser Pro
            20                  25                  30

<210> SEQ ID NO 4
<211> LENGTH: 31
<212> TYPE: PRT
<213> ORGANISM: Cavia porcellus

<400> SEQUENCE: 4

Gly Glu Ser Glu Ile His Ile Phe Val Ala Val Phe Gly Ile Leu Ile
1               5                   10                  15

Leu Leu Ile Cys Leu Cys Gly Thr Thr Trp Leu Cys Cys His Pro
            20                  25                  30

<210> SEQ ID NO 5
<211> LENGTH: 30
<212> TYPE: PRT
<213> ORGANISM: Mus musculus

<400> SEQUENCE: 5

Asp Pro Ser Asp Leu Asn Ile Phe Leu Gly Ile Leu Cys Leu Val Leu
1               5                   10                  15

Leu Ser Thr Thr Cys Val Val Thr Trp Leu Cys Cys Lys Arg
            20                  25                  30
```

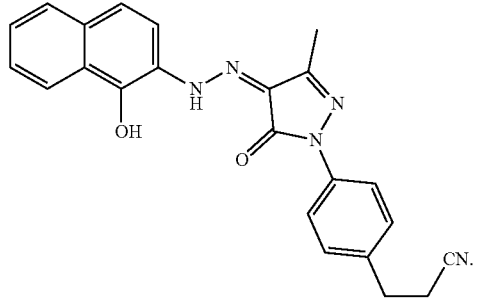

8. The method of claim 1, wherein the compound is:
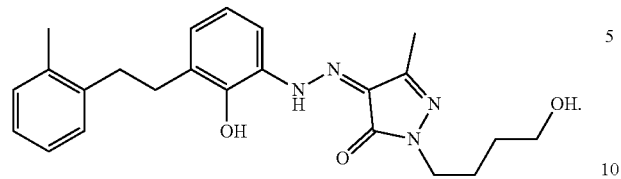

What is claimed is:

1. A method of treating a hematopoietic or neurological disorder selected from the group consisting of granulocytopenia, neutropenia, amyotrophic lateral sclerosis, multiple sclerosis, multiple dystrophy, and spinal cord injury, the method comprising administering an effective amount of a compound of Formula (II) wherein the compound of Formula (II) has the following structure:

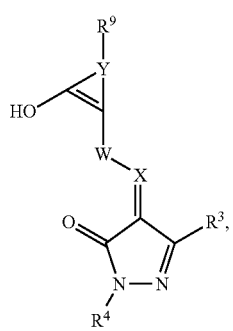

(II)

a tautomer thereof, or a pharmaceutically acceptable salt thereof, wherein:

$R^3$ is selected from hydrogen, an optionally substituted $C_1$-$C_6$ alkyl, an optionally substituted $C_2$-$C_6$ alkenyl, an optionally substituted $C_2$-$C_6$ alkynyl, an optionally substituted $C_1$-$C_6$ heteroalkyl, an optionally substituted $C_3$-$C_8$ cycloalkyl, an optionally substituted $C_3$-$C_8$ cycloalkenyl, an optionally substituted $C_1$-$C_6$ heterocycle, an optionally substituted aryl, and an optionally substituted heteroaryl;

$R^4$ is selected from hydrogen, an optionally substituted $C_1$-$C_6$ alkyl, an optionally substituted $C_2$-$C_6$ alkenyl, an optionally substituted $C_2$-$C_6$ alkynyl, an optionally substituted $C_1$-$C_6$ heteroalkyl, an optionally substituted $C_3$-$C_8$ cycloalkyl, an optionally substituted $C_3$-$C_8$ cycloalkenyl, an optionally substituted $C_1$-$C_6$ heterocycle, an optionally substituted heteroaryl, and an optionally substituted heteroarylalkyl;

$R^9$ is selected from hydrogen, an optionally substituted $C_1$-$C_6$ alkyl, an optionally substituted $C_2$-$C_6$ alkenyl, an optionally substituted $C_2$-$C_6$ alkynyl, an optionally substituted $C_1$-$C_6$ heteroalkyl, an optionally substituted $C_3$-$C_8$ cycloalkyl, an optionally substituted $C_3$-$C_8$ cycloalkenyl, an optionally substituted $C_1$-$C_6$ heterocycle, an optionally substituted heteroaryl, an optionally substituted arylalkyl, an optionally substituted arylalkenyl, an optionally substituted arylalkynyl, an optionally substituted heteroarylalkyl, an optionally substituted heteroarylalkenyl, and an optionally substituted heteroarylalkynyl;

W is selected from O (oxygen) and NH;

X is N (nitrogen) or $CR^2$; and

Y is selected from an optionally substituted $C_1$-$C_6$ alkyl, $C_2$-$C_6$ alkenyl, an optionally substituted $C_1$-$C_6$ heteroalkyl, an optionally substituted $C_1$-$C_6$ heteroalkenyl, an optionally substituted phenylalkenyl, and an optionally substituted heterocyclealkenyl.

2. The method of claim 1, wherein the compound has the structure of Formula (IIa) or (IIb):

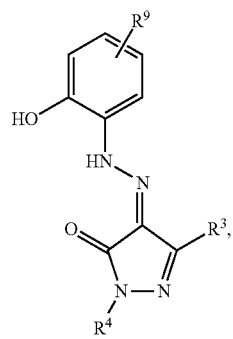

(IIa)

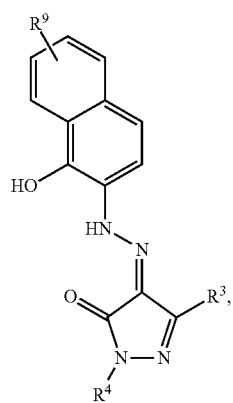

(IIb)

a tautomer thereof, or a pharmaceutically acceptable salt thereof, wherein:

$R^3$ is selected from hydrogen, an optionally substituted $C_1$-$C_6$ alkyl, an optionally substituted $C_3$-$C_8$ cycloalkyl, an optionally substituted $C_1$-$C_6$ heterocycle, an optionally substituted aryl, and an optionally substituted heteroaryl;

$R^4$ is selected from an optionally substituted $C_1$-$C_6$ alkyl, an optionally substituted $C_3$-$C_8$ cycloalkyl, an optionally substituted $C_1$-$C_6$ heterocyclyl; and $R^9$ is selected from hydrogen, an optionally substituted $C_1$-$C_6$ alkyl, an optionally substituted $C_3$-$C_8$ cycloalkyl, an optionally substituted $C_1$-$C_6$ heterocyclyl, an optionally substituted heteroaryl, an optionally substituted arylalkyl, and an optionally substituted heteroarylalkyl.

3. The method of claim 2, wherein:

$R^3$ is selected from hydrogen, and an optionally substituted $C_1$-$C_3$ alkyl;

$R^4$ is selected from an optionally substituted $C_1$-$C_6$ alkyl, an optionally substituted $C_3$-$C_8$ cycloalkyl; and $R^9$ is selected from an optionally substituted $C_1$-$C_6$ alkyl, an optionally substituted arylalkyl, an optionally substituted arylalkenyl, an optionally substituted arylalkynyl, and an optionally substituted heteroarylalkyl.

4. The method of claim 3, wherein:

$R^3$ is an optionally substituted $C_1$-$C_3$ alkyl;

$R^4$ is an optionally substituted $C_1$-$C_4$ alkyl; and $R^9$ is selected from an optionally substituted $C_1$-$C_3$ alkyl, an optionally substituted arylalkyl, an optionally substituted arylalkenyl, and an optionally substituted arylalkynyl.

5. The method of claim 1, wherein the compound is administered in combination with an additional therapeutic regimen selected from the group consisting of chemotherapy, bone marrow transplantation, and radiation therapy.

6. The method of claim 1, wherein the compound is selected from the group consisting of:

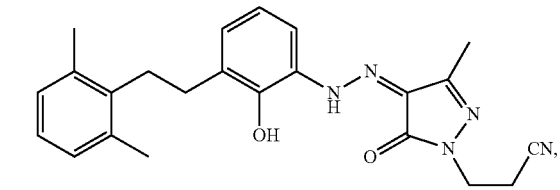

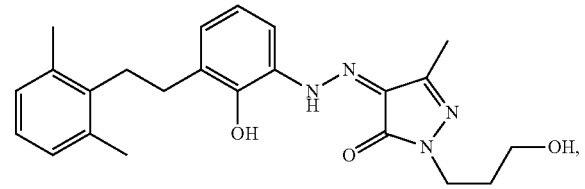

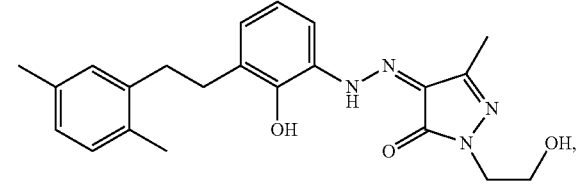

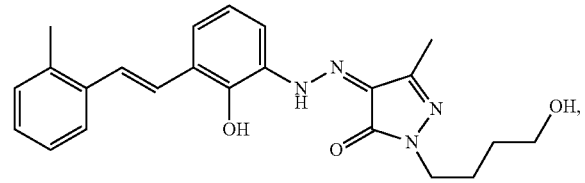

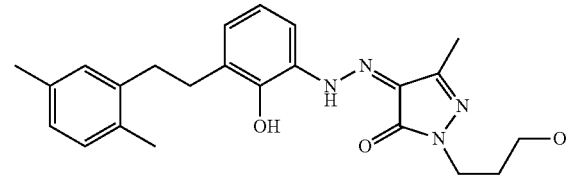

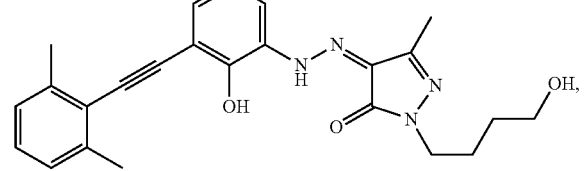

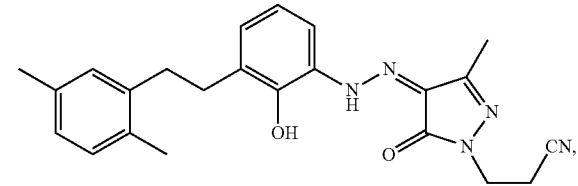

and

-continued

a tautomer thereof, or pharmaceutically acceptable salt thereof.

7. A method of treating a hematopoietic or neurological disorder selected from the group consisting of granulocytopenia, neutropenia, amyotrophic lateral sclerosis, multiple sclerosis, multiple dystrophy, and spinal cord injury, the method comprising administering an effective amount of a compound, wherein the compound is selected from the group consisting:

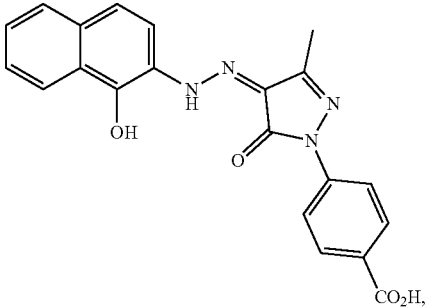

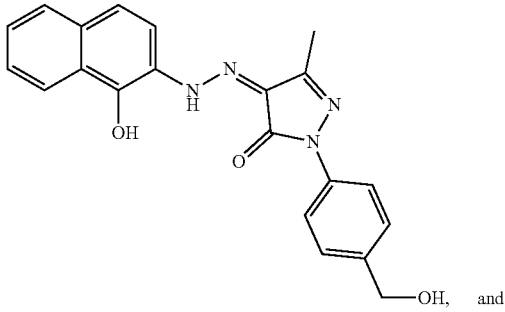

and